US008258266B2

(12) United States Patent
Deshpande et al.

(10) Patent No.: US 8,258,266 B2
(45) Date of Patent: Sep. 4, 2012

(54) IP-10 ANTIBODIES AND THEIR USES

(75) Inventors: Shrikant Deshpande, Fremont, CA (US); Haichun Huang, Fremont, CA (US); Mohan Srinivasan, Cupertino, CA (US); Josephine M. Cardarelli, San Carlos, CA (US); Changyu Wang, Fremont, CA (US); David B. Passmore, San Carlos, CA (US); Vangipuram Rangan, Pleasant Hill, CA (US); Thomas E. Lane, Irvine, CA (US); Hans S. Keirstead, Irvine, CA (US); Michael T. Liu, Irvine, CA (US)

(73) Assignee: Medarex, Inc., Princeton, NJ (US)

( * ) Notice: Subject to any disclaimer, the term of this patent is extended or adjusted under 35 U.S.C. 154(b) by 428 days.

(21) Appl. No.: 12/472,877

(22) Filed: May 27, 2009

(65) Prior Publication Data
US 2010/0077497 A1      Mar. 25, 2010

Related U.S. Application Data

(63) Continuation of application No. 11/009,731, filed on Dec. 10, 2004.

(60) Provisional application No. 60/529,180, filed on Dec. 10, 2003.

(51) Int. Cl.
| | |
|---|---|
| C07K 16/00 | (2006.01) |
| C12P 21/08 | (2006.01) |
| A61K 39/395 | (2006.01) |
| A61K 39/40 | (2006.01) |
| C12N 5/02 | (2006.01) |
| C12N 5/16 | (2006.01) |
| C07K 1/00 | (2006.01) |

(52) U.S. Cl. ............... 530/387.1; 530/387.3; 530/387.9; 530/388.1; 530/388.15; 530/388.2; 530/388.23; 530/391.1; 424/130.1; 424/132.1; 424/134.1; 424/136.1; 424/139.1; 424/141.1; 424/142.1; 424/158.1; 424/178.1; 435/325; 435/326; 435/328; 435/331; 435/335

(58) Field of Classification Search .................. None
See application file for complete search history.

(56) References Cited

U.S. PATENT DOCUMENTS

| | | | |
|---|---|---|---|
| 6,652,854 | B2 | 11/2003 | Mohler et al. |
| 7,084,260 | B1 * | 8/2006 | Lonberg et al. .......... 530/388.75 |
| 7,786,268 | B2 | 8/2010 | Fischer et al. |
| 7,935,793 | B2 | 5/2011 | Balasa et al. |
| 7,964,194 | B2 | 6/2011 | Lillard, Jr. et al. |
| 2003/0166589 | A1 | 9/2003 | Karin |
| 2005/0191293 | A1 | 9/2005 | Deshpande et al. |

FOREIGN PATENT DOCUMENTS

| | | |
|---|---|---|
| WO | WO-01/09187 A2 | 2/2001 |
| WO | WO-02/15932 A1 | 2/2002 |
| WO | WO-2004/101511 A2 | 11/2004 |

OTHER PUBLICATIONS

Sequence alignment, Aug. 15, 2011, pp. 1-4.*
Carr, Daniel J.J. et al., "Effect of Anti-CXCL10 Monoclonal Antibody on Herpes Simplex Virus Type 1 Keratitis and Retinal Infection," *Journal of Virology*, vol. 77(18):10037-10046 (2003).
Carr, D.J. et al., "Neutralizing Antibody to the Chemokine CXCL10 Reduces Ocular Inflammation and Delays Viral Spread Following Cornea HSV-1 Infection," *Invest. Ophthalmol.*, Abstract No. 4183 (2003).
Fishwild, Dianne M. et al., "High-avidity human IgGκ monoclonal antibodies from a novel strain of minilocus transgenic mice," *Nature Biotechnology*, vol. 14:845-851 (1996).
Foung, S.K., et al., "Generation of human monoclonal antibodies by fusion of EBV-activated B cells to a human-mouse hybridoma," *Methods Enzymol.*, vol. 121:168-174 (1986).
Kolb, et al., "Identification of a T cell chemotactic factor in the cerebrospinal fluid of HIV-1-infected individuals as interferon-γ inducible protein 10," *Journal of Neuroimmunology*, vol. 93:172-188 (1999).
Kraan, M.C., et al., "The development of clinical signs of rheumatoid synovial inflammation is associated with increased synthesis of the chemokine CXCL8 (interleukin-8)," *Arthritis Res.*, vol. 3(1):65-71 (2001).
Liu, Michael T. et al., "Neutralization of the Chemokine CXCL10 Reduces Inflammatory Cell Invasion and Demyelination and Improves Neurological Function in a Viral Model of Multiple Sclerosis," *The Journal of Immunology*, vol. 167:4091-4097 (2001).
Marks, James D. et al., "By-passing Immunization: Building High Affinity Human Antibodies by Chain Shuffling," *Nature Biotechnology*, vol. 10:779-783 (1992).
Pandya, Deepal, "Generation of a high affinity humanized anti-IP-10 monoclonal antibody by protein engineering," *The Midwinter Conference of Immunologists*, Poster Abstract (2005).
Patel, D.D., et al., "CXCR3 and CCR5 ligands in rheumatoid arthritis synovium," *Clin. Immunol.*, vol. 98(1):39-45 (2001).
Rader, Christoph et al., "A phage display approach for rapid antibody humanization: Designed combinatorial V gene libraries," *Proc. Natl. Acad. Sci. USA*, vol. 95:8910-8915 (1998).
Reff, et al., "A review of modifications to recombinant antibodies: attempt to increase efficacy in oncology applications," *Critical Reviews in Oncology/Hematology*, vol. 40:25-35 (2001).

(Continued)

*Primary Examiner* — Chun Dahle
(74) *Attorney, Agent, or Firm* — Nelson Mullins Riley & Scarborough LLP; Jane E. Remillard, Esq.; Jeanne M. DiGiorgio, Esq.

(57) ABSTRACT

The present invention provides isolated monoclonal antibodies, particularly human antibodies, that bind to IP-10 with high affinity, inhibit the binding of IP-10 to its receptor, inhibit IP-10-induced calcium flux and inhibit IP-10-induced cell migration. Nucleic acid molecules encoding the antibodies of the invention, expression vectors, host cells and methods for expressing the antibodies of the invention are also provided. Immunoconjugates, bispecific molecules and pharmaceutical compositions comprising the antibodies of the invention are also provided. The invention also provides methods for inhibiting IP-10 activity using the antibodies of the invention, including methods for treating various inflammatory and autoimmune diseases.

17 Claims, 30 Drawing Sheets

OTHER PUBLICATIONS

Rudikoff, Stuart et al., "Single amino acid substitution altering antigen-binding specificity," *Proc. Natl. Acad. Sci. USA*, vol. 79:1979-1983 (1982).

Ruschpler, P., et al., "High CXCR3 expression in synovial mast cells associated with CXCL9 and CXCL10 expression in inflammatory synovial tissues of patients with rheumatoid arthritis," *Arthritis Res. Ther.*, vol. 5(5):R241-R252 (2003).

Salomon, I., et al., "Targeting the Function of IFN-γ-Inducible Protein 10 Suppresses Ongoing Adjuvant Arthritis," *The Journal of Immunology*, vol. 169:2685-2693 (2002).

Söderlind, Eskil et al., "Complementarity-determining region (CDR) implantation: a theme of recombination," *Immunotechnology*, vol. 4:279-285 (1999).

Swaminathan, G. Jawahar et al., "Crystal Structures of Oligomeric Forms of the IP-10/CXCL10 Chemokine," *Structure*, vol. 11:521-532 (2003).

Vajdos, Felix F. et al., "Comprehensive Functional Maps of the Antigen-binding Site of an Anti-ErbB2 Antibody Obtained with Shotgun Scanning Mutagenesis," *J. Mol. Biol.*, vol. 320:415-428 (2002).

European Office Action for Application No. 04813771.5, dated Jan. 13, 2009.

International Search Report for Application No. PCT/US04/29373, Jan. 2004, pp. 1-2.

Written Opinion for Application No. PCT/US04/29373, Jan. 2004, pp. 1-3.

International Search report for Application No. PCT/US04/41506, Apr. 2005, pp. 1-4.

Brown, McKay et al., "Tolerance to Single, but Not Multiple, Amino Acid Replacements in Antibody VH CDR2," The Journal of Immunology, vol. 156:3285-3291 (1996).

Klein, Robyn S. et al., "IFN-Inducible Protein 10/CXC Chemokine Ligand 10-Independent Induction of Experimental Autoimmune Encephalomyelitis," The Journal of Immunology, vol. 172:550-559 (2004).

European Office Action for Application No. 11166104.7, dated Sep. 30, 2011.

* cited by examiner

FIGURE 1A

Anti-IP10 1D4 VH

V segment: 3-33
    D segment: 3-10
    J segment: JH6b

```
         Q   V   Q   L   V   E   S   G   G   G   V   V   Q   P   G   R   S   L
    1    CAG GTG CAG TTG GTG GAG TCT GGG GGA GGC GTG GTC CAG CCT GGG AGG TCC CTG

CDR1
                                                         ~~~~~~~~~~~~~~~~~~~~~
         R   L   S   C   A   A   S   G   F   T   F   S   S   Y   G   M   H   W
    55   AGA CTC TCC TGT GCA GCG TCT GGA TTC ACC TTC AGT AGC TAT GGC ATG CAC TGG

CDR2
                                                         ~~~~~~~~~~~~~~~~~~~~~
         V   R   Q   A   P   G   K   G   L   E   W   V   A   V   I   W   F   E
    109  GTC CGC CAG GCT CCA GGC AAG GGG CTG GAG TGG GTG GCA GTT ATA TGG TTT GAA

CDR2
         ~~~~~~~~~~~~~~~~~~~~~~~~~~~~~~~~~~~~~~~~~~~~~~~
         G   S   I   K   Y   Y   A   D   S   V   K   G   R   F   T   I   S   R
    163  GGA AGT ATT AAA TAC TAT GCA GAC TCC GTG AAG GGC CGA TTC ACC ATC TCC AGA

D   N   S   K   N   T   L   Y   L   Q   M   N   S   L   R   A   E   D
    217  GAC AAT TCC AAG AAT ACG CTG TAT CTG CAA ATG AAC AGC CTG AGA GCC GAG GAC

CDR3
                                                         ~~~~~~~~~~~~~~~~~~~~~~~~~~~~~~
         T   A   V   Y   Y   C   A   R   E   G   A   G   S   S   L   Y   Y   Y
    271  ACG GCT GTG TAT TAT TGT GCG AGA GAG GGT GCG GGG AGT TCT CTC TAC TAC TAC
                                                                     |

CDR3
         ~~~~~~~~~~~~~~~~~~~
         Y   G   M   D   V   W   G   Q   G   T   T   V   T   V   S   S
    325  TAC GGT ATG GAC GTC TGG GGC CAA GGG ACC ACG GTC ACC GTC TCC TCA
```

FIGURE 1B

Anti-IP10 1D4 VK

V segment:    A27
    J segment:    JK2

```
       E   I   V   L   T   Q   S   P   G   T   L   S   L   S   P   G   E   R
  1   GAA ATT GTG TTG ACG CAG TCT CCA GGC ACC CTG TCT TTG TCT CCA GGG GAA AGA

CDR1
                       ~~~~~~~~~~~~~~~~~~~~~~~~~~~~~~~~~~~~~~~~~~~~~~~~~~~~~~
       A   T   L   S   C   R   A   S   Q   S   V   S   S   G   H   L   A   W
 55   GCC ACC CTC TCC TGC AGG GCC AGT CAG AGT GTT AGC AGC GGA CAC TTA GCC TGG

CDR2
                                                                ~~~~~~~~~~~~~
       Y   Q   Q   K   P   G   Q   A   P   R   L   L   I   Y   G   A   S   S
109   TAC CAG CAG AAA CCT GGC CAG GCT CCC AGG CTC CTC ATC TAT GGT GCA TCC AGC

CDR2
      ~~~~~~~~~~~
       R   A   T   G   I   P   G   R   F   S   G   S   G   S   G   T   D   F
163   AGG GCC ACT GGC ATC CCA GGC AGG TTC AGT GGC AGT GGG TCT GGG ACA GAC TTC

~~~
       T   L   T   I   S   R   L   E   P   E   D   F   A   V   Y   Y   C   Q
217   ACT CTC ACC ATC AGC AGA CTG GAG CCT GAA GAT TTT GCA GTG TAT TAC TGT CAG

CDR3
      ~~~~~~~~~~~~~~~~~~~~~~~~~~~~~~~~~~
       Q   Y   G   S   S   P   Y   T   F   G   Q   G   T   K   L   E   I   K
271   CAG TAT GGT AGC TCA CCG TAC ACT TTT GGC CAG GGG ACC AAG CTG GAG ATC AAA
```

FIGURE 2A

Anti-IP10 1E1 VH

V segment:    VH3-33
    D segment:    undetermined
    J segment:    JH3a

```
         Q   E   Q   L   V   E   S   G   G   N   V   V   Q   P   G   R   S   L
  1    CAG GAG CAG CTG GTG GAG TCT GGG GGA AAC GTG GTC CAG CCT GGG AGG TCC CTG

CDR1
                                                              ~~~~~~~~~~~~~~~~~~~
         R   L   S   C   A   A   S   G   F   T   F   S   T   Y   G   M   H   W
 55    AGA CTC TCC TGT GCA GCG TCT GGA TTC ACC TTT AGT ACT TAT GGC ATG CAC TGG

CDR2
                                                                  ~~~~~~~~~~~~~~~
         V   R   Q   A   P   G   K   G   L   E   W   V   A   V   I   W   Y   D
109    GTC CGC CAG GCT CCA GGC AAG GGG CTG GAG TGG GTG GCA GTT ATA TGG TAT GAT

CDR2
       ~~~~~~~~~~~~~~~~~~~~~~~~~~~~~~~~~~~~~~~~~~~~~~~~~~~~~
         G   S   D   K   Y   Y   A   D   S   V   K   D   R   F   T   V   S   K
163    GGA AGT GAT AAA TAC TAT GCA GAC TCC GTG AAG GAC CGA TTC ACG GTC TCC AAA

D   N   S   K   N   T   L   Y   L   Q   M   N   S   L   R   A   E   D
217    GAC AAT TCC AAG AAC ACG CTG TAT CTG CAA ATG AAC AGC CTG AGA GCC GAG GAC

CDR3
                                                              ~~~~~~~~~~~~~~~~~~~~~~~~~~~~~
         T   A   V   Y   Y   C   A   R   N   I   A   V   A   D   V   A   F   D
271    ACG GCT GTG TAT TAC TGT GCG AGA AAT ATA GCA GTG GCT GAC GTT GCT TTT GAT
                                                                    |
       CDR3                                                         ──────▶
       ~~~
         L   W   G   Q   G   T   M   V   T   V   S   S
325    CTC TGG GGC CAG GGG ACA ATG GTC ACC GTC TCT TCA
```

FIGURE 2B

Anti-IP10 1E1 VK

V segment:    L6
    J segment:    JK4

```
         E   I   V   L   T   Q   S   P   A   I   L   S   L   S   P   G   E   R
  1     GAA ATT GTG TTG ACA CAG TCT CCA GCC ATC CTG TCT TTG TCT CCA GGG AAA AGA
                                                CDR1
                                         ~~~~~~~~~~~~~~~~~~~~~~~~~~~~~~~~~~~~~~~
         A   T   L   S   C   R   A   S   Q   S   V   S   S   Y   L   A   W   Y
 55     GCC ACC CTC TCC TGC AGG GCC AGT CAG AGT GTT AGC AGC TAC TTA GCC TGG TAC
                                                                        CDR2
                                                                 ~~~~~~~~~~~~~~~~~~~~
         Q   Q   K   P   G   Q   A   P   R   L   L   I   Y   D   A   S   N   R
109     CAA CAG AAA CCT GGC CAG GCT CCC AGG CTC CTC ATC TAT GAT GCA TCC AAC AGG

CDR2
        ~~~~~~~
         A   T   G   I   P   A   R   F   S   G   S   G   S   G   T   D   F   T
163     GCC ACT GGC ATC CCA GCC AGG TTC AGT GGC AGT GGG TCT GGG ACA GAC TTC ACT
                                                                        CDR3
                                                                       ~~~~~~~~
         L   T   I   S   S   L   E   P   E   D   F   A   V   Y   Y   C   Q   Q
217     CTC ACC ATC AGC AGC CTG GAG CCT GAA GAT TTT GCA GTT TAT TAC TGT CAG CAG

CDR3
        ~~~~~~~~~~~~~~~~~~~~~~~~~~~~~~~~~~~
         R   S   N   W   P   P   L   T   F   G   G   G   T   K   V   E   I   K
271     CGT AGC AAC TGG CCT CCA CTC ACT TTC GGC GGA GGG ACC AAG GTG GAG ATC AAA
```

FIGURE 3A

Anti-IP10 2G1 VH

V segment:   3-33
    D segment:   undetermined
    J segment:   JH6b

```
       Q   V   Q   L   V   E   S   G   G   G   V   V   Q   P   G   R   S   L
  1    CAG GTG CAG CTG GTG GAG TCT GGG GGA GGC GTG GTC CAG CCT GGG AGG TCC CTG
                                                                 CDR1
                                                                 ~~~~~~~~~~~~~~~~~
       R   L   S   C   A   A   S   G   F   T   F   S   N   C   G   M   H   W
 55    AGA CTC TCC TGT GCA GCG TCT GGA TTC ACC TTC AGT AAC TGT GGC ATG CAC TGG
                                                                 CDR2
                                                                 ~~~~~~~~~~~~~~~~~
       V   R   Q   A   P   G   K   G   L   E   W   V   A   L   I   G   Y   D
109    GTC CGC CAG GCT CCA GGC AAG GGG CTG GAG TGG GTG GCA CTT ATA GGG TAT GAT
                       CDR2
       ~~~~~~~~~~~~~~~~~~~~~~~~~~~~~~~~~~~~~~~~~~~~~~~~~~~~
       G   I   N   E   Y   Y   A   D   S   V   K   G   R   F   T   I   S   R
163    GGA ATT AAT GAA TAC TAT GCA GAC TCC GTG AAG GGC CGA TTC ACC ATC TCC AGA

D   N   S   K   N   T   L   Y   L   Q   M   N   S   L   R   A   E   D
217    GAC AAT TCC AAG AAC ACG CTG TAT CTG CAA ATG AAC AGC CTG AGA GCC GAG GAC
                                                         CDR3
                                                         ~~~~~~~~~~~~~~~~~~~~~~~~~~~~~
       T   A   V   F   Y   C   A   R   D   W   P   E   G   Y   Y   N   G   M
271    ACG GCT GTG TTT TAC TGT GCG AGA GAC TGG CCT GAG GGC TAC TAC AAC GGC ATG
       CDR3
       ~~~~~~~
       D   V   W   G   Q   G   T   T   V   T   V   S   S
325    GAC GTC TGG GGC CAA GGG ACC ACG GTC ACC GTC TCC TCA
```

FIGURE 3B

Anti-IP10 2G1 VK

V segment:   A27
    J segment:   JK3

```
        E   I   V   L   T   Q   S   P   G   T   L   S   L   S   P   G   E   R
  1    GAA ATT GTG TTG ACG CAG TCT CCA GGC ACC CTG TCT TTG TCT CCA GGG AAA AGA
                                                 CDR1
                        ~~~~~~~~~~~~~~~~~~~~~~~~~~~~~~~~~~~~~~~~~~~~~~~~
        A   T   L   S   C   R   A   S   Q   S   V   S   S   S   Y   L   A   W
 55    GCC ACC CTC TCC TGC AGG GCC AGT CAG AGT GTT AGC AGC AGC TAC TTA GCC TGG
                                                                     CDR2
                                                                 ~~~~~~~~~~~~~~~~
        Y   Q   Q   K   P   G   Q   A   P   R   L   L   I   Y   G   A   S   S
109    TAC CAG CAG AAA CCT GGC CAG GCT CCC AGG CTC CTC ATC TAT GGT GCA TCC AGC

CDR2
        ~~~~~~~~~~~~
        R   A   T   G   I   P   D   R   F   S   G   S   G   S   G   T   D   F
163    AGG GCC ACT GGC ATC CCA GAC AGG TTC AGT GGC AGT GGG TCT GGG ACA GAC TTC
                                                                         CDR3
                                                                         ~~~
        T   L   T   I   S   R   L   E   P   E   D   F   A   V   Y   Y   C   Q
217    ACT CTC ACC ATC AGC AGA CTG GAG CCT GAA GAT TTT GCA GTG TAT TAC TGT CAG

CDR3
        ~~~~~~~~~~~~~~~~~~~~~~~~~~~~~~~~~~~~~~
        Q   Y   G   S   S   P   P   F   T   F   G   P   G   T   K   V   D   I
271    CAG TAT GGT AGC TCA CCT CCA TTC ACT TTC GGC CCT GGG ACC AAA GTG GAT ATC

K
325    AAA
```

FIGURE 4A

Anti-IP10 3C4 VH

V segment: 5-51
    D segment: D2-15
    J segment: JH1

```
       E   V   Q   L   V   Q   S   G   A   E   V   K   K   P   G   E   S   L
  1    GAG GTG CAG CTG GTG CAG TCT GGA GCA GAG GTG AAA AAG CCC GGG GAG TCT CTG

CDR1
                                                            ~~~~~~~~~~~~~~~~~~~
       K   I   S   C   K   G   S   G   Y   N   F   P   S   Y   W   I   G   W
 55    AAG ATC TCC TGT AAG GGT TCT GGA TAC AAC TTT CCC AGC TAC TGG ATC GGC TGG

CDR2
                                                            ~~~~~~~~~~~~~~~~~~~
       V   R   Q   M   P   G   K   G   L   E   W   M   G   V   I   S   P   G
109    GTG CGC CAG ATG CCC GGG AAA GGC CTG GAG TGG ATG GGG GTC ATC TCT CCT GGT

CDR2
       ~~~~~~~~~~~~~~~~~~~~~~~~~~~~~~~~~~~~~~~~~~~~~~~~~~~
       D   S   D   T   R   Y   S   P   S   F   Q   G   Q   V   T   I   S   A
163    GAC TCT GAT ACC AGA TAC AGC CCG TCC TTC CAA GGC CAA GTC ACC ATC TCA GCC

D   K   S   I   S   T   A   Y   L   Q   W   S   S   L   K   A   S   D
217    GAC AAG TCC ATC AGC ACC GCC TAC CTG CAG TGG AGC AGC CTG AAG GCC TCG GAC

CDR3
                                            ~~~~~~~~~~~~~~~~~~~~~~~~~~~~~~~~~~~
       T   A   M   Y   Y   C   A   R   G   Y   C   S   G   G   S   C   Y   P
271    ACC GCC ATG TAT TAC TGT GCG AGA GGA TAT TGT AGT GGT GGT AGC TGC TAC CCA

CDR3
       ~~~~~~~~~~~~~~~~
       F   F   Q   Y   W   G   Q   G   T   L   V   T   V   S   S
325    TTC TTC CAG TAC TGG GGC CAG GGC ACC CTG GTC ACC GTC TCC TCC
```

FIGURE 4B

Anti-IP10 3C4 VK

V segment: L18
    J segment: JK4

```
        A   I   Q   L   T   Q   S   P   S   S   L   S   A   S   V   G   D   R
  1     GCC ATC CAG TTG ACC CAG TCT CCA TCC TCC CTG TCT GCA TCT GTA GGA GAC AGA
                                            CDR1
                            ~~~~~~~~~~~~~~~~~~~~~~~~~~~~~~~~~~~~~~~~~~~~
        V   T   I   T   C   R   A   S   Q   G   I   S   S   A   L   A   W   Y
 55     GTC ACC ATC ACT TGC CGG GCA AGT CAG GGC ATT AGC AGT GCT TTA GCC TGG TAT
                                                                    CDR2
                                                            ~~~~~~~~~~~~~~~~~~~
        Q   Q   K   P   G   K   A   P   K   L   L   I   Y   D   A   S   S   L
109     CAG CAG AAA CCA GGG AAA GCT CCT AAG CTC CTG ATC TAT GAT GCC TCC AGT TTG

CDR2
        ~~~~~~~
        E   S   G   V   P   S   R   F   S   G   S   G   S   G   T   D   F   T
163     GAA AGT GGG GTC CCA TCA AGG TTC AGC GGC AGT GGA TCT GGG ACA GAT TTC ACT
                                                                        CDR3
                                                                        ~~~~~~~
        L   T   I   S   S   L   Q   P   E   D   F   A   T   Y   Y   C   Q   Q
217     CTC ACC ATC AGC AGC CTG CAG CCT GAA GAT TTT GCA ACT TAT TAC TGT CAA CAG

CDR3
        ~~~~~~~~~~~~~~~~~~~~~~~~~~~~
        F   D   S   F   P   H   T   F   G   G   G   T   K   V   E   I   K
271     TTT GAT AGT TTC CCT CAC ACT TTC GGC GGA GGG ACC AAG GTG GAG ATC AAA
```

FIGURE 5A

Anti-IP10 6A5 VH

V segment:    3-33
    D segment:    3-10
    J segment:    JH6b

```
         Q   M   Q   L   V   E   S   G   G   G   V   V   Q   P   G   R   S   L
   1     CAA ATG CAG CTG GTG GAG TCT GGG GGA GGC GTG GTC CAG CCT GGG AGG TCC CTG

CDR1
                                                              ~~~~~~~~~~~~~~~~
         R   L   S   C   T   A   S   G   F   T   F   S   N   N   G   M   H   W
  55     AGA CTC TCC TGT ACA GCG TCT GGA TTC ACC TTC AGT AAC AAT GGC ATG CAC TGG

CDR2
                                                              ~~~~~~~~~~~~~~~~~~
         V   R   Q   A   P   G   K   G   L   E   W   V   A   V   I   W   F   D
 109     GTC CGC CAG GCT CCA GGC AAG GGG CTG GAG TGG GTG GCA GTT ATA TGG TTT GAT

CDR2
         ~~~~~~~~~~~~~~~~~~~~~~~~~~~~~~~~~~~~~~~~~~~~~~~~
         G   M   N   K   F   Y   V   D   S   V   K   G   R   F   T   I   S   R
 163     GGA ATG AAT AAA TTC TAT GTA GAC TCC GTG AAG GGC CGA TTC ACC ATC TCC AGA

D   N   S   K   N   T   L   Y   L   E   M   N   S   L   R   A   E   D
 217     GAC AAT TCC AAG AAC ACG CTG TAT CTG GAA ATG AAC AGC CTG AGA GCC GAG GAC

CDR3
                                                    ~~~~~~~~~~~~~~~~~~~~~~~~~~~~
         T   A   I   Y   Y   C   A   R   E   G   D   G   S   G   I   Y   Y   Y
 271     ACG GCT ATA TAT TAC TGT GCG AGA GAA GGG GAT GGT TCG GGA ATT TAT TAC TAC

CDR3
         ~~~~~~~~~~~~~~~~~~
         Y   G   M   D   V   W   G   Q   G   T   T   V   T   V   S   S
 325     TAC GGT ATG GAC GTC TGG GGC CAA GGG ACC ACG GTC ACC GTC TCC TCA
```

FIGURE 5B

Anti-IP10 6A5 VK

V segment:  A27
    J segment:  JK3

```
          E   I   V   L   T   Q   S   P   G   T   L   S   L   S   P   G   E   R
  1      GAA ATT GTG TTG ACG CAG TCT CCA GGC ACC CTG TCT TTG TCT CCA GGG GAA AGA
                                                  CDR1
                                         ~~~~~~~~~~~~~~~~~~~~~~~~~~~~~~~~~~~~~~~
          A   T   L   S   C   R   A   S   Q   S   V   S   S   S   Y   L   A   W
  55     GCC ACC CTC TCC TGC AGG GCC AGT CAG AGT GTT AGC AGC AGC TAT TTA GCC TGG
                                                                       CDR2
                                                              ~~~~~~~~~~~~~~~~~~
          Y   Q   Q   K   P   G   Q   A   P   R   L   L   I   Y   G   A   S   S
  109    TAC CAG CAG AAA CCT GGC CAG GCT CCC AGG CTC CTC ATC TAT GGT GCA TCC AGC

CDR2
         ~~~~~~~~~~~~
          R   A   T   G   I   P   D   R   F   S   G   S   G   S   G   T   D   F
  163    AGG GCC ACT GGC ATC CCA GAC AGG TTC AGT GGC AGT GGG TCT GGG ACA GAC TTC
                                                                           CDR 3
                                                                           ~~~
          T   L   T   I   S   R   L   E   P   E   D   F   A   V   Y   Y   C   Q
  217    ACT CTC ACC ATC AGC AGA CTG GAG CCT GAA GAT TTT GCA GTG TAT TAC TGT CAG
                     CDR3
         ~~~~~~~~~~~~~~~~~~~~~~~~~~~~~~~~~~~~~
          Q   Y   G   S   S   P   I   F   T   F   G   P   G   T   K   V   D   I
  271    CAG TAT GGT AGC TCA CCT ATA TTC ACT TTC GGC CCT GGG ACC AAA GTG GAT ATC

K
  325    AAA
```

FIGURE 6A

Anti-IP10 6A8 VH

V segment:    3-33
    D segment:    undetermined
    J segment:    JH6b

```
         Q   V   Q   L   V   E   S   G   G   G   V   V   Q   P   G   R   S   L
  1    CAG GTG CAG CTG GTG GAG TCT GGG GGA GGC GTG GTC CAG CCT GGG AGG TCC CTG

CDR1
                                                           ~~~~~~~~~~~~~~~~~~~
         R   L   S   C   T   A   S   G   F   T   F   S   T   Y   G   M   H   W
 55    AGA CTC TCC TGT ACA GCG TCT GGA TTC ACC TTC AGT ACC TAT GGC ATG CAC TGG

CDR2
                                                           ~~~~~~~~~~~~~~~~~~~
         V   R   Q   A   P   G   K   G   L   E   W   V   A   I   I   W   F   D
109    GTC CGC CAG GCT CCA GGC AAG GGG CTG GAG TGG GTG GCA ATT ATA TGG TTC GAT

CDR2
       ~~~~~~~~~~~~~~~~~~~~~~~~~~~~~~~~~~~~~~~~~~~~~~~~
         G   S   N   E   D   Y   A   A   S   V   K   G   R   F   T   I   S   R
163    GGA AGT AAT GAA GAT TAT GCA GCC TCC GTG AAG GGC CGA TTC ACC ATC TCC AGA

D   N   S   K   N   T   L   Y   L   Q   M   N   S   L   R   A   E   D
217    GAC AAT TCC AAG AAC ACG CTG TAT CTG CAA ATG AAC AGC CTG AGA GCC GAG GAC

CDR3
                                           ~~~~~~~~~~~~~~~~~~~~~~~~~~~~~~~~~~~
         T   A   V   Y   Y   C   A   R   E   G   D   G   S   S   L   Y   Y   Y
271    ACG GCT GTG TAT TAC TGT GCG AGA GAG GGG GAT GGG AGC TCC TTA TAC TAC TAC

CDR3
       ~~~~~~~~~~~~~~~~~~~
         Y   G   M   D   V   W   G   Q   G   T   T   V   T   V   S   S
325    TAC GGT ATG GAC GTC TGG GGC CAA GGG ACC ACG GTC ACC GTC TCC TCA
```

FIGURE 6B

Anti-IP10 6A8 VK

V segment: A27
J segment: JK4

```
      E   V   V   L   T   Q   S   P   G   T   L   S   L   S   P   G   E   R
  1  GAA GTT GTG TTG ACG CAG TCT CCA GGC ACC CTG TCT TTG TCT CCA GGG GAA AGA
                                              CDR1
                         ~~~~~~~~~~~~~~~~~~~~~~~~~~~~~~~~~~~~~~~~~~~~~~~~~~~
      A   T   L   S   C   R   A   S   Q   S   I   S   S   G   Y   L   A   W
 55  GCC ACC CTC TCC TGC AGG GCC AGT CAG AGT ATT AGC AGC GGC TAC TTA GCC TGG
                                                                      CDR2
                                                                  ~~~~~~~~~~~~
      Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC

CDR2
     ~~~~~~~~~~~~
      R   A   T   G   I   P   D   R   F   S   G   S   G   S   G   T   D   F
163  AGG GCC ACT GGC ATC CCA GAC AGG TTC AGT GGC AGT GGG TCT GGG ACA GAC TTC

CDR3
                                                                       ~~~
      T   L   T   I   S   R   L   E   P   E   D   F   A   V   Y   Y   C   Q
217  ACT CTC ACC ATC AGC AGA CTG GAG CCT GAA GAT TTT GCA GTG TAT TAC TGT CAG
             CDR3
     ~~~~~~~~~~~~~~~~~~~~~~~~~~~~
      Q   Y   G   S   S   P   T   F   G   G   G   T   K   V   E   I   K
271  CAG TAT GGT AGC TCA CCC ACT TTC GGC GGA GGG ACC AAG GTG GAG ATC AAA
```

FIGURE 7A

Anti-IP10 6B10 VH

V segment:       3-30.3
    D segment:       5-12
    J segment:       JH4b

```
      Q   V   Q   L   V   E   S   G   G   V   V   Q   P   G   R   S   L
  1   CAG GTG CAG CTG GTG GAG TCT GGG GGA GGC GTG GTC CAG CCT GGG AGG TCC CTG

CDR1
                                                      ~~~~~~~~~~~~~~~~~~~~
      R   L   S   C   A   A   S   G   F   T   F   S   N   S   A   M   H   W
 55   AGA CTC TCC TGT GCA GCC TCT GGA TTC ACC TTC AGT AAC TCT GCT ATG CAC TGG

CDR2
                                                      ~~~~~~~~~~~~~~~~~~~~
      V   R   Q   A   P   G   K   G   L   E   W   V   A   L   I   P   F   D
109   GTC CGC CAG GCT CCA GGC AAG GGG CTG GAG TGG GTG GCA CTT ATA CCA TTT GAT

CDR2
~~~~~~~~~~~~~~~~~~~~~~~~~~~~~~~~~~~~~~~~~~~~~~~~
      G   Y   N   K   Y   Y   A   D   S   V   K   G   R   F   T   I   S   R
163   GGA TAC AAT AAA TAC TAC GCA GAC TCC GTG AAG GGC CGA TTC ACC ATC TCC AGA

D   N   S   K   N   T   L   Y   L   Q   M   N   S   L   R   A   E   D
217   GAC AAT TCC AAG AAC ACG CTG TAT CTG CAA ATG AAC AGC CTG AGA GCT GAG GAC

CDR3
                                                  ~~~~~~~~~~~~~~~~~~~~~~~~~~~~~~~~~~~
      T   A   V   Y   Y   C   A   R   E   G   G   Y   T   G   Y   D   G   G
271   ACG GCT GTG TAT TAC TGC GCG AGA GAA GGT GGA TAT ACT GGC TAC GAT GGG GGA

CDR3
      ~~~~~~~~~~~~
      F   D   Y   W   G   Q   G   I   L   V   T   V   S   S
325   TTT GAC TAT TGG GGC CAG GGA ATC CTG GTC ACC GTC TCC TCA
```

FIGURE 7B

Anti-IP10 6B10 VK

V segment:    L6
    J segment:    JK2

```
            E   I   V   L   T   Q   S   P   A   T   L   S   L   S   P   G   E   R
    1   GAA ATT GTG TTG ACA CAG TCT CCA GCC ACC CTG TCT TTG TCT CCA GGG GAA AGA
                                              CDR1
                                ~~~~~~~~~~~~~~~~~~~~~~~~~~~~~~~~~~~~~~~~
            A   T   L   S   C   R   A   S   Q   S   V   S   S   Y   L   A   W   Y
   55   GCC ACC CTC TCC TGC AGG GCC AGT CAG AGT GTT AGC AGC TAC TTA GCC TGG TAC
                                                                          CDR2
                                                                  ~~~~~~~~~~~~~~~~~~~~
            Q   Q   K   P   G   Q   A   P   R   L   L   I   Y   D   A   S   N   R
  109   CAA CAG AAA CCT GGC CAG GCT CCC ACG CTC CTC ATC TAT GAT GCA TCC AAC AGG

CDR2
        ~~~~~~~
            A   T   G   I   P   A   R   F   S   G   S   G   S   G   T   D   F   T
  163   GCC ACT GGC ATC CCA GCC AGG TTC AGT GGC AGT GGG TCT GGG ACA GAC TTC ACT
                                                                          CDR3
                                                                          ~~~~~~~
            L   T   I   S   S   L   E   P   E   D   F   A   V   Y   Y   C   Q   Q
  217   CTC ACC ATC AGC AGC CTA GAG CCT GAA GAT TTT GCA GTT TAT TAC TGT CAG CAG

CDR3
        ~~~~~~~~~~~~~~~~~~~~~~~~~~~~~~~~~
            R   S   N   W   P   P   Y   T   F   G   Q   G   T   K   L   E   I   K
  271   CGT AGC AAC TGG CCT CCG TAC ACT TTT GGC CAG GGG ACC AAG CTG GAG ATC AAA
```

FIGURE 8A

Anti-IP10 7C10 VH

```
V segment: 3-33
D segment: 3-10
J segment: JH4b
```

```
        Q   V   Q   L   V   E   S   G   G   G   V   V   Q   P   G   R   S   L
  1    CAG GTG CAA CTG GTG GAG TCT GGG GGA GGC GTG GTC CAG CCT GGG AGG TCC CTG
                                                                    CDR1
                                                                    ~~~~~~~~~~~~~~~~~~~
        R   L   S   C   A   A   S   G   F   T   F   S   N   S   G   M   H   W
 55    AGA CTC TCC TGT GCA GCG TCT GGA TTC ACC TTC AGT AAC TCT GGC ATG CAC TGG
                                                                    CDR2
                                                                    ~~~~~~~~~~~~~~~~~~~
        V   R   Q   A   P   G   K   G   L   E   W   V   A   V   I   D   Y   D
109    GTC CGC CAG GCT CCA GGC AAG GGG CTG GAG TGG GTG GCA GTT ATA GAC TAT GAT
                        CDR2
       ~~~~~~~~~~~~~~~~~~~~~~~~~~~~~~~~~~~~~~~~~~~~~~~~
        G   I   I   Q   Y   Y   A   D   S   V   K   G   R   F   T   I   S   R
163    GGA ATT ATT CAA TAC TAT GCC GAC TCC GTG AAG GGC CGA TTC ACC ATC TCC AGA

D   N   S   K   N   T   L   Y   L   Q   I   N   S   L   R   A   E   D
217    GAC AAT TCC AAG AAC ACG CTG TAT CTG CAA ATA AAC AGC CTG AGA GCC GAG GAC
                                                            CDR3
                                                            ~~~~~~~~~~~~~~~~~~~~~~~~~~~~~~~~~~~~~
        T   A   V   Y   Y   C   A   T   E   R   G   T   H   Y   Y   G   S   G
271    ACG GCT GTG TAT TAC TGT GCG ACA GAG AGG GGC ACG CAT TAC TAT GGT TCG GGG
            CDR3
       ~~~~~~~~~~~~~~~~~
        S   F   D   Y   W   G   Q   G   T   L   V   T   V   S   S
325    AGT TTT GAC TAC TGG GGC CAG GGA ACC CTG GTC ACC GTC TCC TCA
```

FIGURE 8B

Anti-IP10 7C10 VK

V segment:    L15
    J segment:    JK4

```
          D   I   Q   M   T   Q   S   P   S   S   L   S   A   S   V   G   D   R
  1      GAC ATC CAG ATG ACC CAG TCT CCA TCC TCA CTG TCT GCA TCT GTA GGA GAC AGA

CDR1
                                  ~~~~~~~~~~~~~~~~~~~~~~~~~~~~~~~~~~~~~~
          V   T   I   T   C   R   A   S   Q   G   I   S   S   W   L   A   W   Y
  55     GTC ACC ATC ACT TGT CGG GCG AGT CAG GGT ATT AGC AGC TGG TTA GCC TGG TAT

CDR2
                                                                ~~~~~~~~~~~~~~~~~~~~
          Q   Q   K   P   E   K   A   P   K   S   L   I   Y   A   A   S   S   L
  109    CAG CAG AAA CCA GAG AAA GCC CCT AAG TCC CTG ATC TAT GCT GCA TCC AGT TTG

CDR2
         ~~~~~~~
          Q   S   G   V   P   S   R   F   S   G   S   G   S   G   T   D   F   T
  163    CAA AGT GGG GTC CCA TCA AGG TTC AGC GGC AGT GGA TCT GGG ACA GAT TTC ACT

CDR3
                                                                         ~~~~~~~~
          L   T   I   S   S   L   Q   P   E   D   F   A   T   Y   Y   C   Q   Q
  217    CTC ACC ATC AGC AGC CTG CAG CCT GAA GAT TTT GCA ACT TAT TAC TGC CAA CAG

CDR3
         ~~~~~~~~~~~~~~~~~~~~~~~~~~~
          Y   N   S   Y   P   P   T   F   G   G   G   T   K   V   E   I   K
  271    TAT AAT AGT TAC CCT CCC ACT TTC GGC GGA GGG ACC AAG GTG GAG ATC AAA
```

FIGURE 9A

Anti-IP10 8F6 VH

V segment:      3-30.3
    D segment:      6-13
    J segment:      JH4b

```
         Q   V   Q   L   V   D   S   G   G   G   V   V   Q   P   G   R   S   L
   1   CAG GTG CAA CTG GTG GAC TCT GGG GGA GGC GTG GTC CAG CCT GGG AGG TCC CTG

CDR1
                                                        ~~~~~~~~~~~~~~~~~~
         R   L   S   C   A   A   S   G   F   T   F   N   T   Y   G   M   H   W
  55   AGA CTC TCC TGT GCA GCC TCT GGA TTC ACC TTC AAT ACC TAT GGC ATG CAC TGG

CDR2
                                                                ~~~~~~~~~~~~~~~~~~
         V   R   Q   A   P   G   K   G   L   E   W   V   A   V   I   S   Y   D
 109   GTC CGC CAG GCT CCA GGC AAG GGG CTG GAG TGG GTG GCA GTT ATA TCA TAT GAT

CDR2
       ~~~~~~~~~~~~~~~~~~~~~~~~~~~~~~~~~~~~~~~~~~~~~~~~~~~~
         G   I   I   K   H   Y   A   D   S   V   K   G   R   F   T   I   T   R
 163   GGA ATC ATT AAA CAC TAC GCC GAC TCC GTG AAG GGC CGA TTC ACC ATA ACC AGA

D   N   S   K   N   M   V   H   L   Q   M   N   S   L   R   A   E   D
 217   GAC AAT TCC AAG AAC ATG GTG CAT CTG CAA ATG AAC AGC CTG AGA GCT GAG GAC

CDR3
                                               ~~~~~~~~~~~~~~~~~~~~~~~~~~~~~~~~~~
         T   A   V   Y   Y   C   A   R   D   S   S   S   W   Y   V   Y   F   D
 271   ACG GCT GTG TAT TAC TGT GCG AGA GAT AGC AGC AGC TGG TAC GTC TAC TTT GAC

CDR3
       ~~~
         Y   W   G   Q   G   T   L   V   T   V   S   S
 325   TAC TGG GGC CAG GGA ACC CTG GTC ACC GTC TCC TCA
```

FIGURE 9B

Anti-IP10 8F6 VK

V segment:       L6
    J segment:       JK1

```
           E   I   V   L   T   Q   S   P   A   T   L   S   L   S   P   G   E   R
   1      GAA ATT GTG TTG ACA CAG TCT CCA GCC ACC CTG TCT TTG TCT CCA GGG GAA AGA
                                              CDR1
                                   ~~~~~~~~~~~~~~~~~~~~~~~~~~~~~~~~~~~~~
           A   T   L   S   C   R   A   S   Q   S   V   S   S   Y   V   A   W   Y
  55      GCC ACC CTC TCC TGC AGG GCC AGT CAG AGT GTT AGC AGC TAC GTA GCC TGG TAC
                                                                      CDR2
                                                                 ~~~~~~~~~~~~~~~~~~~
           Q   Q   K   P   G   Q   A   P   R   L   L   I   Y   D   A   S   N   R
 109      CAA CAG AAA CCT GGC CAG GCT CCC AGG CTC CTC ATC TAT GAT GCA TCC AAC AGG

CDR2
          ~~~~~~~
           A   T   G   I   P   A   R   F   S   G   S   G   S   G   T   D   F   T
 163      GCC ACT GGC ATC CCA GCC AGG TTC AGT GGC AGT GGG TCT GGG ACA GAC TTC ACT
                                                                          CDR3
                                                                         ~~~~~~~
           L   T   I   S   S   L   E   P   E   D   F   A   I   Y   Y   C   Q   Q
 217      CTC ACC ATC AGC AGC CTA GAG CCT GAA GAT TTT GCA ATT TAT TAC TGT CAG CAG

CDR3
          ~~~~~~~~~~~~~~~~~~~~~~~~~~~~~~~~~~
           R   S   N   S   P   P   W   T   F   G   Q   G   T   K   V   E   I   K
 271      CGT AGC AAC TCG CCT CCG TGG ACG TTC GGC CAA GGG ACC AAG GTG GAA ATC AAA
```

FIGURE 10A

Anti-IP10 10A12 VH

V-segment: 3-33
    D-segment: undetermined
    J-segment: JH6b

```
        Q   V   Q   L   V   E   S   G   G   G   V   V   Q   P   G   R   S   L
  1     CAG GTG CAG CTG GTG GAG TCT GGG GGA GGC GTG GTC CAG CCT GGG AGG TCC CTG

CDR1
                                                                ~~~~~~~~~~~~~~~~~~~
        R   L   S   C   A   A   S   G   F   T   F   S   N   C   G   M   H   W
 55     AGA CTC TCC TGT GCA GCG TCT GGA TTC ACC TTC AGT AAC TGT GGC ATG CAC TGG

CDR2
                                                                        ~~~~~~~~~~~~~~
        V   R   Q   A   P   G   K   G   L   E   W   V   A   L   I   G   F   D
109     GTC CGC CAG GCT CCA GGC AAG GGG CTG GAG TGG GTG GCA CTT ATA GGG TTT GAT

CDR2
        ~~~~~~~~~~~~~~~~~~~~~~~~~~~~~~~~~~~~~~~~~~~~~~~~~~
        G   I   N   E   Y   Y   A   D   S   V   K   G   R   F   T   I   S   R
163     GGA ATT AAT GAA TAC TAT GCA GAC TCC GTG AAG GGC CGA TTC ACC ATC TCC AGA

D   N   S   K   N   T   L   Y   L   Q   M   N   S   L   R   A   E   D
217     GAC AAT TCC AAG AAC ACG CTG TAT CTG CAA ATG AAC AGC CTG AGA GCC GAG GAC

CDR3
                                                        ~~~~~~~~~~~~~~~~~~~~~~~~~~~~~~~~~~~~
        T   A   V   Y   Y   C   A   R   D   W   P   E   G   Y   Y   N   G   M
271     ACG GCT GTG TAT TAT TGT GCG AGA GAC TGG CCT GAG GGC TAC TAC AAC GGC ATG

CDR3
        ~~~~~~~
        D   V   W   G   Q   G   T   T   V   T   V   S   S
325     GAC GTC TGG GGC CAA GGG ACC ACG GTC ACC GTC TCC TCA
```

FIGURE 10B

Anti-IP10 10A12 VK

V segment: A27
    J segment: JK3

```
            E   I   V   L   T   Q   S   P   G   T   L   S   L   S   P   G   E   R
  1        GAA ATT GTG TTG ACG CAG TCT CCA GGC ACC CTG TCT TTG TCT CCA GGG AAA AGA
                                              CDR1
                                     ~~~~~~~~~~~~~~~~~~~~~~~~~~~~~~~~~~~~~~~~~~~~
            A   T   L   S   C   R   A   S   Q   S   V   S   S   S   Y   L   A   W
 55        GCC ACC CTC TCC TGC AGG GCC AGT CAG AGT GTT AGC AGC AGC TAC TTA GCC TGG
                                                                         CDR2
                                                                ~~~~~~~~~~~~~~~~~
            Y   Q   Q   K   P   G   Q   A   P   R   L   L   I   Y   G   A   S   S
109        TAC CAG CAG AAA CCT GGC CAG GCT CCC AGG CTC CTC ATC TAT GGT GCA TCC AGC

CDR2
           ~~~~~~~~~~~~~
            R   A   T   G   I   P   D   R   F   S   G   S   G   S   G   T   D   F
163        AGG GCC ACT GGC ATC CCA GAC AGG TTC AGT GGC AGT GGG TCT GGG ACA GAC TTC

CDR3
                                                                              ~~~
            T   L   T   I   S   R   L   E   P   E   D   F   A   V   Y   Y   C   Q
217        ACT CTC ACC ATC AGC AGA CTG GAG CCT GAA GAT TTT GCA GTG TAT TAC TGT CAG

CDR3
           ~~~~~~~~~~~~~~~~~~~~~~~~~~~~~~~~~~~~~~
            Q   Y   G   S   S   P   P   F   T   F   G   P   G   T   K   V   D   I
271        CAG TAT GGT AGC TCA CCT CCA TTC ACT TTC GGC CCT GGG ACC AAA GTG GAT ATC

K
325        AAA
```

FIGURE 11A

Anti-IP10 13C4 VH

V segment:    4-61
    D segment:    3-10
    J segment:    JH6b

```
          Q   V   Q   L   Q   E   S   G   P   G   L   V   K   P   S   E   T   L
  1       CAG GTG CAG CTG CAG GAG TCG GGC CCA GGA CTG GTG AAG CCT TCG GAG ACC CTG
                                                                    CDR1
                                                                    ~~~~~~~~~~~~~~~~~~~
          S   L   T   C   T   I   S   G   G   S   V   S   S   G   D   Y   Y   W
  55      TCC CTC ACC TGC ACT ATC TCT GGT GGC TCC GTC AGC AGT GGT GAT TAC TAC TGG

CDR1                                                              CDR2
          ~~~                                                               ~~~~~~~~~~~
          S   W   I   R   Q   P   P   G   K   G   L   E   W   I   G   N   I   Y
  109     AGC TGG ATC CGG CAG CCC CCA GGG AAG GGA CTG GAG TGG ATT GGG AAC ATC TAT

CDR2
          ~~~~~~~~~~~~~~~~~~~~~~~~~~~~~~~~~~~~~~~~~~~~~~~~~~~~~~~~~~~
          Y   S   G   S   T   N   Y   N   P   S   L   K   S   R   V   T   I   S
  163     TAC AGT GGG AGC ACC AAC TAC AAC CCC TCC CTC AAG AGT CGA GTC ACC ATA TCG

V   D   T   S   K   N   Q   F   S   L   K   L   S   S   V   T   A   A
  217     GTA GAC ACG TCC AAG AAC CAG TTC TCC CTG AAG CTG AGC TCT GTG ACC GCT GCG
                                                                        CDR3
                                                                        ~~~~~~~~~~~~~~~~~~~~~~~~
          D   T   A   V   Y   Y   C   A   R   G   G   G   T   V   V   R   G   I
  271     GAC ACG GCC GTG TAT TAC TGT GCG AGA GGG GGG GGT ACT GTG GTT CGG GGA ATT

CDR3
          ~~~~~~~~~~~~~~~~~~~~~~~~~~~~~~~~~~~~~~~~~~~~~~~~~
          I   H   Y   Y   Y   Y   Y   G   M   D   V   W   G   Q   G   T   T   V
  325     ATC CAT TAC TAC TAC TAC TAC GGT ATG GAC GTC TGG GGC CAA GGG ACC ACG GTC

T   V   S   S
  379     ACC GTC TCC TCA
```

FIGURE 11B

Anti-IP10 13C4 VK

V segment: A27
J segment: JK2

```
          E   I   V   L   T   Q   S   P   G   T   L   S   L   S   P   G   E   R
  1       GAA ATT GTG TTG ACG CAG TCT CCA GGC ACC CTG TCT TTG TCT CCA GGG GAA AGA

CDR1
                                        ~~~~~~~~~~~~~~~~~~~~~~~~~~~~~~~~~~~~~~~~
          A   T   L   S   C   R   A   S   Q   S   V   S   S   S   Y   L   A   W
  55      GCC ACC CTC TCC TGC AGG GCC AGT CAG AGT GTT AGC AGC AGC TAC TTA GCC TGG

CDR2
                                                                    ~~~~~~~~~~~~~~
          Y   Q   Q   K   P   G   Q   A   P   R   L   L   I   Y   G   A   S   S
  109     TAC CAG CAG AAA CCT GGC CAG GCT CCC AGG CTC CTC ATC TAT GGT GCA TCC AGC

CDR2
          ~~~~~~~~~~~
          R   A   T   G   I   P   D   R   F   S   G   S   G   S   G   T   D   F
  163     AGG GCC ACT GGC ATC CCA GAC AGG TTC AGT GGC AGT GGG TCT GGG ACA GAC TTC

CDR3
                                                                              ~~~
          T   L   T   I   S   R   L   E   P   E   D   F   A   V   Y   Y   C   Q
  217     ACT CTC ACC ATC AGC AGA CTG GAG CCT GAA GAT TTT GCA GTG TAT TAC TGT CAG

CDR3
          ~~~~~~~~~~~~~~~~~~~~~~~~~~~~~~~~~~~~~~~
          Q   Y   G   S   S   P   E   Y   T   F   G   Q   G   T   K   L   E   I
  271     CAG TAT GGT AGC TCA CCG GAG TAC ACT TTT GGC CAG GGG ACC AAG CTG GAG ATC

K
  325     AAA
```

FIGURE 12

|  | | | | | | | | | | | | | | | | | | | | | | | CDR1 | | | |
|---|---|---|---|---|---|---|---|---|---|---|---|---|---|---|---|---|---|---|---|---|---|---|---|---|---|---|
| 3-33 germline | Q | V | Q | L | V | E | S | G | G | G | V | V | Q | P | G | R | S | L | R | L | S | C | A | A | S | G | F | T | F | S | S | Y | G | M | H |
| 6A5 | - | M | - | - | - | - | - | - | - | - | - | - | - | - | - | - | - | - | - | - | - | - | - | - | - | - | - | - | - | - | N | N | - | - | - |
| 6A8 | - | - | - | - | - | - | - | - | - | - | - | - | - | - | - | - | - | - | - | - | - | - | T | - | - | - | - | - | - | - | T | - | - | - | - |
| 2G1 | - | - | - | - | E | - | - | - | - | - | - | - | - | - | - | - | - | - | - | - | - | - | - | - | - | - | - | - | - | - | N | C | - | - | - |
| 10A12 | - | - | - | - | - | - | - | - | - | - | - | - | - | - | - | - | - | - | - | - | - | - | T | - | - | - | - | - | - | - | N | C | - | - | - |
| 1E1 | - | - | - | - | - | - | - | - | - | - | - | - | - | - | - | - | - | - | - | - | - | - | - | - | - | - | - | - | - | - | T | - | - | - | - |
| 7C10 | - | - | - | - | - | - | - | - | - | - | - | - | - | - | - | - | - | - | - | - | - | - | - | - | - | - | - | - | - | - | N | S | - | - | - |
| 1D4 | - | - | - | - | - | - | - | - | - | - | - | - | - | - | - | - | - | - | - | - | - | - | - | - | - | - | - | - | - | - | - | - | - | - | - |

|  | | | | | | | | | | | | | | | CDR2 | | | | | | | | | | | | |
|---|---|---|---|---|---|---|---|---|---|---|---|---|---|---|---|---|---|---|---|---|---|---|---|---|---|---|---|
| 3-33 germline | W | V | R | Q | A | P | G | K | G | L | E | W | V | A | V | I | W | Y | D | G | S | N | K | Y | Y | A | D | S | V | K | G | R | F | T | I |
| 6A5 | - | - | - | - | - | - | - | - | - | - | - | - | - | - | - | - | - | F | - | - | - | - | M | - | - | F | - | V | - | - | - | - | - | - | - |
| 6A8 | - | - | - | - | - | - | - | - | - | - | - | - | - | - | - | - | - | F | - | - | - | - | - | - | - | E | D | - | - | - | - | - | - | - | - |
| 2G1 | - | - | - | - | - | - | - | - | - | - | - | - | - | - | - | - | - | - | L | - | - | - | - | - | - | E | - | - | - | - | - | - | - | - | - |
| 10A12 | - | - | - | - | - | - | - | - | - | - | - | - | - | - | - | - | - | G | L | - | - | - | - | - | - | E | - | - | - | - | - | - | - | - | - |
| 1E1 | - | - | - | - | - | - | - | - | - | - | - | - | - | - | - | - | - | G | F | - | - | - | - | - | - | - | - | A | - | - | - | - | - | - | - |
| 7C10 | - | - | - | - | - | - | - | - | - | - | - | - | - | - | - | - | - | - | - | D | - | - | - | - | - | - | D | - | - | - | D | - | - | - | V |
| 1D4 | - | - | - | - | - | - | - | - | - | - | - | - | - | - | - | - | - | F | E | - | - | - | H | - | - | Q | - | - | - | - | - | - | - | - | - |

|  | | | | | | | | | | | | | | | | | | | | | | | | CDR3 | | |
|---|---|---|---|---|---|---|---|---|---|---|---|---|---|---|---|---|---|---|---|---|---|---|---|---|---|---|
| 3-33 germline | S | R | D | N | S | K | N | T | L | Y | L | Q | M | N | S | L | R | A | E | D | T | A | V | Y | Y | C | A | R |
| 6A5 | - | - | - | - | - | - | - | - | - | - | - | - | - | - | - | - | - | - | - | - | - | - | - | H | - | - | - | - |
| 6A8 | - | - | - | - | - | - | - | - | - | - | - | - | - | - | - | - | - | - | - | - | - | - | - | - | - | - | - | - |
| 2G1 | - | - | - | - | - | - | - | - | - | - | - | E | - | - | - | - | - | - | - | - | - | - | - | - | - | - | - | - |
| 10A12 | - | - | - | - | - | - | - | - | - | - | - | - | - | - | - | - | - | - | - | - | - | - | - | F | - | - | - | - |
| 1E1 | - | - | - | - | - | K | - | - | - | - | - | - | - | - | - | - | - | - | - | - | - | - | - | - | - | - | - | - |
| 7C10 | - | - | - | - | - | - | - | - | - | - | - | - | - | - | - | - | - | - | - | - | - | - | - | - | - | - | - | - |
| 1D4 | - | - | - | - | - | - | - | - | - | - | - | - | - | H | - | - | - | - | - | - | - | - | - | - | - | - | - | - |

|  | CDR3 | | | | | | | | | | | | |
|---|---|---|---|---|---|---|---|---|---|---|---|---|---|
| 6A5 | Y | Y | Y | Y | G | M | D | V | W | G | Q | G | T | T | V | T | V | S | S |
| 6A8 | - | - | - | - | - | - | - | - | - | - | - | - | - | - | - | - | - | - | - |
| 2G1 | N | - | - | - | - | - | - | - | - | - | - | - | - | - | - | - | - | - | - |
| 10A12 | N | - | - | - | - | - | - | - | - | - | - | - | - | - | - | M | - | - | - |
| 1E1 | A | F | D | L | - | - | - | - | - | - | - | - | - | - | - | - | L | - | - |
| 7C10 | G | S | G | F | D | Y | - | - | - | - | - | - | - | - | - | - | - | - | - |
| 1D4 | - | - | - | - | - | - | - | - | - | - | - | - | - | - | - | - | - | - | - |

| 6A5 | E | G | D | G | S | G | I |
| 6A8 | - | - | - | - | - | - | - |
| 2G1 | - | - | - | - | - | - | - |
| 10A12 | - | - | - | - | - | - | - |
| 1E1 | - | - | - | - | - | - | - |
| 7C10 | - | - | - | - | - | - | - |
| 1D4 | - | - | - | - | - | - | - |

(Note: the CDR3 region shows varied sequences: 6A5: EGDGSGI -SL; 6A8: DWPEGYY; 2G1: DWPEGYY; 10A12: NIAVADV; 1E1: T-RGTHYY; 7C10: -A- -SL)

```
                              CDR1
3-30.3 Germline  Q V Q L V E S G G G V V Q P G R S L R L S C A A S G F T F S S Y A M H W V R Q
6B10 VH          - - - - - - - - - - - - - - - - - - - - - - - - - - - - - N S - - - - - - -
8F6 VH           - - - - D - - - - - - - - - - - - - - - - - - - - - - N T - - G - - - - - - -

CDR2
3-30.3 Germline  A P G K G L E W V A V I S Y D G S N K Y Y A D S V K G R F T I S R D N S K N T
6B10 VH          - - - - - - - - - - - - - L P F - - Y - - - - - - - - - - - - - - - - - - - -
8F6 VH           - - - - - - - - - - - - - - - H - - - - - - - - - - - - T - - - - - - - - M CDR3
3-30.3 Germline  L Y L Q M N S L R A E D T A V Y Y C A R
6B10 VH          - - - - - - - - - - - - - - - - - - - -   E G G Y T G Y D G G F D Y W G Q G I L -
8F6 VH           V H - - - - - - - - - - - - - - - - - -   D S S S W Y V Y - - - - - - - - - - T

```
                                                         CDR1
5-51 germline    E V Q L V Q S G A E V K K P G E S L K I S C K G S G Y S F T S Y W I G
3C4 VH           - - - - - - - - - - - - - - - - - - - - - - - - - - N - P - - - - -

CDR2
5-51 germline    W V R Q M P G K G L E W M G I I Y P G D S D T R Y S P S F Q G Q V T I
3C4 VH           - - - - - - - - - - - - - - - - - - V - S - - - - - - - - - - - - -

CDR3
5-51 germline    S A D K S I S T A Y L Q W S S L K A S D T A M Y Y C A R - - G Y C S G G S
3C4 VH           - - - - - - - - - - - - - - - - - - - - - - - - - - - - - - - - - - -

CDR3
3C4 VH           C Y P F F Q Y W G Q G T L V T V S S
```

FIGURE 14

```
4-61 Germline:  Q V Q L Q E S G P G L V K P S E T L S L T C T V S G G S V S S G S Y Y W S W I R Q P
13C4 VH:        - - - - - - - - - - - - - - - - - - - - - - - I - - - - - - - D - - - - - - - - -
                                                              |_____CDR1_____|

4-61 Germline:  P G K G L E W I G Y I Y Y S G S T N Y N P S L K S R V T I S V D T S K N Q F S L K L
13C4 VH:        - - - - - - - - - - - - - N - - - - - - - - - - - - - - - - - - - - - - - - - -
                                        |_____CDR2_____|

4-61 Germline:  S S V T A A D T A V Y Y C A R - - - - - - - - - - - - - - - - - - - - - - - - -
13C4 VH:        - - - - - - - - - - - - - - - G G G T V V R G I H Y Y Y Y Y G M D V W G Q G T T V T V S
                                              |_____CDR3_____|
S
```

```
                                                      CDR1
L6 germline  E I V L T Q S P A T L S L S P G E R A T L S C R A S Q S V S S Y L A
1E1          - - - - - - - - - - - - - - - - - - - - - - - - - - - - - - - - -
6B10         - - - - - - - - - - - I - - - - - - - - - - - - - - - - - - - - -
8F6          - - - - - - - - - - - - - - - - - - - - - - - - - - - - - - - - V CDR2
L6 germline  W Y Q Q K P G Q A P R L L I Y D A S N R A T G I P A R F S G S G S G
1E1          - - - - - - - - - - - - - - - - - - - - - - - - - - - - - - - - -
6B10         - - - - - - - - - - - - - - - - - - - - - - - - - - - - - - - - -
8F6          - - - - - - - - - - - - - - - - - - - - - - - - - - - - - - - - -

CDR3
L6 germline  T D F T L T I S S L E P E D F A V Y Y C Q Q R S N W P   P L T F G G G
1E1          - - - - - - - - - - - - - - - - - - - - - - - - - - -   - - - - - - -
6B10         - - - - - - - - - - - - - - - - - - - - - - - S - - -   - Y - - - - Q
8F6          - - - - - - - - - - - - - - - - - I - - - - - - W - -   - - - - - - Q T K V E I K
1E1          - - - - - -
6B10         - - L - - -
8F6          - - - - - -
```

FIGURE 17

```
L18 Germline:  A I Q L T Q S P S S L S A S V G D R V T I T C R A S Q G I S S A L A
3C4 VK:        - - - - - - - - - - - - - - - - - - - - - - - - - - - - - - - - -
                                                      |_____CDR1_____|

L18 Germline:  W Y Q Q K P G K A P K L L I Y D A S S L E S G V P S R F S G S G S G
3C4 VK:        - - - - - - - - - - - - - - - - - - - - - - - - - - - - - - - - -
                                       |_____CDR2_____|

L18 Germline:  T D F T L T I S S L Q P E D F A T Y Y C Q Q F N S Y P
3C4 VK:        - - - - - - - - - - - - - - - - - - - - - D - F - H T F G G G T
                                                        |____CDR3____|

```
L15 Germline  D I Q M T Q S P S S L S A S V G D R V T I T C R A S Q G I S S W L A
7C10 VK       - - - - - - - - - - - - - - - - - - - - - - - - - - - - - - - - -
                                                              └─────CDR1─────┘

L15 Germline  W Y Q Q K P E K A P K S L I Y A A S S L Q S G V P S R F S G S G S G
7C10 VK       - -             - - - - - - - └────CDR2────┘ - - - - - - - - - - -

L15 Germline  T D F T L T I S S L Q P E D F A T Y Y C Q Q Y N S Y P - - P T F G G G T
7C10 VK       - - - - - - - - - - - - - - - - - - - - └────CDR3────┘ - - - - - - - -

… # IP-10 ANTIBODIES AND THEIR USES

RELATED APPLICATIONS

This application is continuation of U.S. application Ser. No. 11/009,731, filed Dec. 10, 2004, which is a non-provisional of U.S. application No. 60/529,180, filed Dec. 10, 2003, the contents of which are hereby incorporated by reference.

BACKGROUND OF THE INVENTION

Interferon gamma inducible protein 10 (IP-10) (also known as CXCL10) is a 10 kDa chemokine that was originally identified based on expression of the IP-10 gene in cells treated with interferon gamma (IFN-gamma) (Luster, A. D. et al. (1985) *Nature* 315:672-676). IP-10 shows homology to proteins having chemotactic activity, such as platelet factor 4 and beta-thromboglobulin, and to proteins having mitogenic activity, such as connective tissue-activating peptide III (Luster, A. D. et al. (1987) *Proc. Natl. Acad. Sci. USA* 84:2868-2871). IP-10 is secreted by a variety of cells, including endothelial cells, monocytes, fibroblasts, and keratinocytes, in response to IFN-gamma (Luster, A. D. and Ravetch, J. V. (1987) *J. Exp. Med.* 166:1084-1097). IP-10 also has been shown to be present in dermal macrophages and endothelial cells in delayed type hypersensitivity (DTH) responses in human skin (Kaplan, G. et al. (1987) *J. Exp. Med.* 166:1098-1108). Although originally identified based on its being induced by IFN-gamma, IP-10 also can be induced by IFN-alpha, for example in dendritic cells (Padovan, E. et al. (2002) *J. Leukoc. Biol.* 71:669-676). IP-10 expression can also be induced in cells of the central nervous system, such as astrocytes and microglia, by stimuli such as IFN-gamma, viruses and lipopolysaccharide (Vanguri, R. and Farber, J. M. (1994) *J. Immunol.* 152:1411-1418; Ren, L. Q. et al. (1998) *Brain Res. Mol. Brain. Res.* 59:256-263). The immunobiology of IP-10 is reviewed in Neville, L. F et al. (1997) *Cytokine Growth Factor Rev.* 8:207-219.

The receptor for IP-10 has been identified as CXCR3, a seven transmembrane receptor (Loetscher, M. et al. (1996) *J. Exp. Med.* 184:963-969). CXCR3 has been shown to be expressed on activated T lymphocytes but not on resting T lymphocytes, nor on B lymphocytes, monocytes or granulocytes (Loetscher, M. et al., supra). CXCR3 expression has been shown to be upregulated on NK cells by stimulation with TGF-beta 1 (Inngjerdingen, M. et al. (2001) *Blood* 97:367-375). Two other ligands for CXCR3 have also been identified: MIG (Loetscher, M. et al., supra) and ITAC (Cole, K. E. et al. (1998) *J. Exp. Med.* 187:2009-2021).

Binding of IP-10 to CXCR3 has been shown to mediate calcium mobilization and chemotaxis in activated T cells (Loetscher, M. et al., supra). Chemotaxis and intracellular calcium mobilization are also induced by IP-10 binding to CXCR3 on activated NK cells (Maghazachi, A. A. et al. (1997) *FASEB J.* 11:765-774). Within the thymus, IP-10 has been shown to be a chemoattractant for TCRαβ⁺ CD8⁺ T cells, TCRγδ⁺ T cells and NK-type cells (Romagnani, P. et al. (2001) *Blood* 97:601-607).

IP-10 or its receptor CXCR3 have been identified in a variety of different inflammatory and autoimmune conditions, including multiple sclerosis (see e.g., Sorensen, T. L. et al. (1999) *J. Clin. Invest.* 103:807-815), rheumatoid arthritis (see e.g., Patel, D. D. et al. (2001) *Clin. Immunol.* 98:39-45), ulcerative colitis (see e.g., Uguccioni, M. et al. (1999) *Am. J. Pathol.* 155:331-336), hepatitis (see e.g., Narumi, S. et al. (1997) *J. Immunol.* 158:5536-5544), spinal cord injury (see e.g., McTigue, D. M. et al. (1998) *J. Neurosci. Res.* 53:368-376; Gonzalez et al. 2003. Exp. Neurol. 184:456-463), systemic lupus erythematosus (see e.g., Narumi, S. et al. (2000) *Cytokine* 12:1561-1565), transplant rejection (see e.g., Zhang, Z. et al. (2002) *J. Immunol.* 168:3205-3212), Sjogren's syndrome (see e.g., Ogawa, N. et al. (2002) *Arthritis Rheum.* 46:2730-2741). Accordingly, therapeutic agents that inhibit the activity are desirable, in particular agents that are suitable for use in humans.

SUMMARY OF THE INVENTION

The present invention provides isolated monoclonal antibodies, in particular human monoclonal antibodies, that bind to IP-10 and that exhibit numerous desirable properties. These properties include high affinity binding to human IP-10, as well as cross-reactivity with rhesus monkey IP-10 but lacking substantial cross-reactivity with either human MIG, human ITAC or mouse IP-10. Furthermore, the antibodies inhibit the binding of IP-10 to its receptor, CXCR3, inhibit calcium flux induced by IP-10 in receptor-expressing cells and inhibit IP-10 induced cell migration (chemotaxis). Still further, antibodies of the invention have been shown to bind to IP-10 in brain sections of a human subject diagnosed with multiple sclerosis.

In preferred embodiments of the invention, the human IP-10 comprises a polypeptide having an amino acid sequence as set forth in SEQ ID NO: 121 [Genbank Acc. No. NP_001556]; the CXCR3 comprises a polypeptide having an amino acid sequence as set forth in SEQ ID NO: 122 [Genbank Acc. No. NP_001495]; the rhesus monkey IP-10 comprises a polypeptide having an amino acid sequence as set forth in SEQ ID NO: 123 [Genbank Acc. No. AAK95955]; the mouse IP-10 comprises a polypeptide having an amino acid sequence as set forth in SEQ ID NO: 124 [Genbank Acc. No. NP_067249]; the human MIG comprises a polypeptide having an amino acid sequence as set forth in SEQ ID NO: 125 [Genbank Acc. No. NP_002407]; and/or the human ITAC comprises a polypeptide having an amino acid sequence as set forth in SEQ ID NO: 126 [Genbank Acc. No. NP_005400].

In one embodiment, the invention provides an isolated monoclonal antibody, or an antigen-binding portion thereof, wherein the antibody specifically binds to IP-10 and comprises a heavy chain variable region that is the product of or derived from a human $V_H$ germline gene selected from the group consisting of a human $V_H$ 3-33 gene, a human $V_H$ 3-30.3 gene, a human $V_H$ 5-51 gene and a human $V_H$ 4-61 gene. In another embodiment, the invention provides an isolated monoclonal antibody, or an antigen-binding portion thereof, wherein the antibody specifically binds to IP-10 and comprises a light chain variable region that is the product of or derived from a human $V_k$ germline gene selected from the group consisting of a human $V_k$ A27 gene, a human $V_k$ L15 gene, a human $V_k$ L6 gene and a human $V_k$ L18 gene. In still another embodiment, the invention provides an isolated monoclonal antibody, or an antigen-binding portion thereof, wherein the antibody specifically binds to IP-10 and comprises:

(a) a heavy chain variable region that is the product of or derived from a human $V_H$ germline gene selected from the group consisting of a human $V_H$ 3-33 gene, a human $V_H$ 3-30.3 gene, a human $V_H$ 5-51 gene and a human $V_H$ 4-61 gene; and (b) a light chain variable region that is the product of or derived from a human $V_k$ germline gene selected from the group consisting of a human $V_k$ A27 gene, a human $V_k$ L15 gene, a human $V_k$ L6 gene and a human $V_k$ L18 gene.

In one embodiment, the invention provides an isolated monoclonal antibody, or an antigen-binding portion thereof, wherein the antibody comprises:
(a) a heavy chain variable region that is the product of or derived from a human $V_H$ 3-33 gene; and
(b) a light chain variable region that is the product of or derived from a human Vk gene selected from the group consisting of a human Vk A27, a human Vk L15 gene and a human Vk L6 gene,
wherein the antibody specifically binds to IP-10.

In another embodiment, the invention provides an isolated monoclonal antibody, or an antigen-binding portion thereof, wherein the antibody comprises:
(a) a heavy chain variable region that is the product of or derived from a human $V_H$ 3-30.3 gene; and
(b) a light chain variable region that is the product of or derived from a human Vk L6 gene;
wherein the antibody specifically binds to IP-10.

In yet another embodiment, the invention provides an isolated monoclonal antibody, or an antigen-binding portion thereof, wherein the antibody comprises:
(a) a heavy chain variable region that is the product of or derived from a human $V_H$ 5-51 gene; and
(b) a light chain variable region that is the product of or derived from a human Vk L18 gene;
wherein the antibody specifically binds to IP-10.

In yet another embodiment, the invention provides an isolated monoclonal antibody, or an antigen-binding portion thereof, wherein the antibody comprises:
(a) a heavy chain variable region that is the product of or derived from a human $V_H$ 4-61 gene; and
(b) a light chain variable region that is the product of or derived from a human Vk A27 gene;
wherein the antibody specifically binds to IP-10.

In another aspect, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:
(a) the heavy chain variable region CDR3 sequence comprises an amino acid sequence selected from the group consisting of amino acid sequences of SEQ ID NOs: 24-34, and conservative modifications thereof,
(b) the light chain variable region CDR3 sequence comprises an amino acid sequence selected from the group consisting of amino acid sequence of SEQ ID NOs: 73-83, and conservative modifications thereof,
(c) the antibody specifically binds to IP-10, and
(d) the antibody exhibits at least one of the following functional properties:
(i) the antibody inhibits binding of IP-10 to CXCR3;
(ii) the antibody inhibits IP-10 induced calcium flux;
(iii) the antibody inhibits IP-10 induced cell migration;
(iv) the antibody cross-reacts with rhesus monkey IP-10;
(v) the antibody does not cross-react with mouse IP-10;
(vi) the antibody does not cross-react with human MIG;
(vii) the antibody does not cross-react with human ITAC.

In a preferred embodiment, the heavy chain variable region CDR2 sequence comprises an amino acid sequence selected from the group consisting of amino acid sequences of SEQ ID NOs: 13-23, and conservative modifications thereof; and the light chain variable region CDR2 sequence comprises an amino acid sequence selected from the group consisting of amino acid sequences of SEQ ID NOs: 62-72, and conservative modifications thereof. In another preferred embodiment, the heavy chain variable region CDR1 sequence comprises an amino acid sequence selected from the group consisting of amino acid sequences of SEQ ID NOs: 1-12, and conservative modifications thereof; and the light chain variable region CDR1 sequence comprises an amino acid sequence selected from the group consisting of amino acid sequences of SEQ ID NOs: 51-61, and conservative modifications thereof. The antibody can be, for example, a human antibody, a humanized antibody or a chimeric antibody.

In another aspect, the invention provides an isolated monoclonal antibody, or antigen binding portion thereof, comprising a heavy chain variable region and a light chain variable region, wherein:
(a) the heavy chain variable region comprises an amino acid sequence that is at least 80% homologous to an amino acid sequence selected from the group consisting of SEQ ID NOs: 35-46,
(b) the light chain variable region comprises an amino acid sequence that is at least 80% homologous to an amino acid sequence selected from the group consisting of SEQ ID NOs: 84-94,
(c) the antibody specifically binds to IP-10, and
(d) the antibody exhibits at least one of the following functional properties:
(i) the antibody inhibits binding of IP-10 to CXCR3;
(ii) the antibody inhibits IP-10 induced calcium flux;
(iii) the antibody inhibits IP-10 induced cell migration;
(iv) the antibody cross-reacts with rhesus monkey IP-10;
(v) the antibody does not cross-react with mouse IP-10;
(vi) the antibody does not cross-react with human MIG;
(vii) the antibody does not cross-react with human ITAC.

The antibody can be, for example, a human antibody, a humanized antibody or a chimeric antibody.

In preferred embodiments of the invention, the isolated monoclonal antibody, or antigen binding portion thereof comprises:
(a) a heavy chain variable region CDR1 comprising an amino acid sequence selected from the group consisting of SEQ ID NOs: 1-12;
(b) a heavy chain variable region CDR2 comprising an amino acid sequence selected from the group consisting of SEQ ID NOs: 13-23;
(c) a heavy chain variable region CDR3 comprising an amino acid sequence selected from the group consisting of SEQ ID NOs: 24-34;
(d) a light chain variable region CDR1 comprising an amino acid sequence selected from the group consisting of SEQ ID NOs: 51-61;
(e) a light chain variable region CDR2 comprising an amino acid sequence selected from the group consisting of SEQ ID NOs: 62-72; and
(f) a light chain variable region CDR3 comprising an amino acid sequence selected from the group consisting of SEQ ID NOs: 73-83;
wherein the antibody specifically binds IP-10.

In other preferred embodiments, the invention provides an isolated monoclonal antibody, or antigen binding portion thereof comprising:
(a) a heavy chain variable region comprising an amino acid sequence selected from the group consisting of SEQ ID NOs: 35-46; and
(b) a light chain variable region comprising an amino acid sequence selected from the group consisting of SEQ ID NOs: 84-94;
wherein the antibody specifically binds IP-10.

In another aspect of the invention, antibodies, or antigen-binding portions thereof, are provided that compete for binding to IP-10 with any of the aforementioned antibodies.

The antibodies of the invention can be, for example, full-length antibodies, for example of an IgG1 or IgG4 isotype. Alternatively, the antibodies can be antibody fragments, such as Fab or Fab'2 fragments, or single chain antibodies.

The invention also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen binding portion thereof.

Compositions comprising an antibody, or antigen-binding portion thereof, or immunoconjugate or bispecific molecule of the invention and a pharmaceutically acceptable carrier are also provided.

Nucleic acid molecules encoding the antibodies, or antigen-binding portions thereof, of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

In another aspect, the invention provides a method of inhibiting an inflammatory or autoimmune response mediated by activated T cells or NK cells comprising contacting the T cells or NK cells with the antibody, or antigen-binding portion thereof, of the invention, such that the inflammatory or autoimmune response is inhibited.

In yet another aspect, the invention provides a method of treating an inflammatory or autoimmune disease in a subject in need of treatment comprising administering to the subject the antibody, or antigen-binding portion thereof, of the invention, such that the inflammatory or autoimmune disease in the subject is treated. The disease can be, for example, multiple sclerosis, rheumatoid arthritis, inflammatory bowel disease (e.g., ulcerative colitis, Crohn's disease), systemic lupus erythematosus, Type I diabetes, inflammatory skin disorders (e.g., psoriasis, lichen planus), autoimmune thyroid disease (e.g., Graves' disease, Hashimoto's thyroiditis), Sjogren's syndrome, pulmonary inflammation (e.g., asthma, chronic obstructive pulmonary disease, pulmonary sarcoidosis, lymphocytic alveolitis), transplant rejection, spinal cord injury, brain injury (e.g., stroke), neurodegenerative diseases (e.g., Alzheimer's disease, Parkinson's disease), gingivitis, gene therapy-induced inflammation, diseases of angiogenesis, inflammatory kidney disease (e.g., IgA nephropathy, memranoproliferative glomerulonephritis, rapidly progressive glomerulonephritis) and atherosclerosis.

In still another aspect, the invention provides a method of treating a viral or bacterial infection involving unwanted IP-10 activity in a subject in need of treatment comprising administering to the subject the antibody, or antigen-binding portion thereof, of the invention, such that the viral or bacterial infection in the subject is treated. For example, the antibodies can be used to treat viral meningitis, viral encephalitis or bacterial meningitis. Viral infection to be treated by the method of the invention can be mediated by, for example, human immunodeficiency virus (HIV), hepatitis C virus (HCV), herpes simplex virus type I (HSV-1) or the Severe Acute Respiratory Syndrome (SARS) virus.

The invention also provides methods for making "second generation" anti-IP-10 antibodies based on the sequences of the anti-IP-10 antibodies provided herein. For example, the invention provides a method for preparing an anti-IP-10 antibody comprising:

(a) providing: (i) a heavy chain variable region antibody sequence comprising a CDR1 sequence selected from the group consisting of SEQ ID NOs: 1-12, a CDR2 sequence selected from the group consisting of SEQ ID NOs: 13-23 and/or a CDR3 sequence selected from the group consisting of SEQ ID NOs: 24-34; and (ii) a light chain variable region antibody sequence comprising a CDR1 sequence selected from the group consisting of SEQ ID NOs: 51-61, a CDR2 sequence selected from the group consisting of SEQ ID NOs: 62-72 and/or a CDR3 sequence selected from the group consisting of SEQ ID NOs: 73-83;

(b) altering at least one amino acid residue within the heavy chain variable region antibody sequence and/or the light chain variable region antibody sequence to create at least one altered antibody sequence; and (c) expressing the altered antibody sequence as a protein.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 99) and amino acid sequence (SEQ ID NO: 35) of the heavy chain variable region of the 1D4 human monoclonal antibody. The CDR1 (SEQ ID NO: 1), CDR2 (SEQ ID NO: 13) and CDR3 (SEQ ID NO: 24) regions are delineated and the V, D and J germline derivations are indicated.

FIG. 1B shows the nucleotide sequence (SEQ ID NO: 110) and amino acid sequence (SEQ ID NO: 84) of the light chain variable region of the 1D4 human monoclonal antibody. The CDR1 (SEQ ID NO: 51), CDR2 (SEQ ID NO: 62) and CDR3 (SEQ ID NO: 73) regions are delineated and the V and J germline derivations are indicated.

FIG. 2A shows the nucleotide sequence (SEQ ID NO: 100) and amino acid sequence (SEQ ID NO: 36) of the heavy chain variable region of the 1E1 human monoclonal antibody. The CDR1 (SEQ ID NO: 2), CDR2 (SEQ ID NO: 14) and CDR3 (SEQ ID NO: 25) regions are delineated and the V and J germline derivations are indicated.

FIG. 2B shows the nucleotide sequence (SEQ ID NO: 111) and amino acid sequence (SEQ ID NO: 85) of the light chain variable region of the 1E1 human monoclonal antibody. The CDR1 (SEQ ID NO: 52), CDR2 (SEQ ID NO: 63) and CDR3 (SEQ ID NO: 74) regions are delineated and the V and J germline derivations are indicated.

FIG. 3A shows the nucleotide sequence (SEQ ID NO: 101) and amino acid sequence (SEQ ID NO: 37) of the heavy chain variable region of the 2G1 human monoclonal antibody. The CDR1 (SEQ ID NO: 3), CDR2 (SEQ ID NO: 15) and CDR3 (SEQ ID NO: 26) regions are delineated and the V and J germline derivations are indicated.

FIG. 3B shows the nucleotide sequence (SEQ ID NO: 112) and amino acid sequence (SEQ ID NO: 86) of the light chain variable region of the 2G1 human monoclonal antibody. The CDR1 (SEQ ID NO: 53), CDR2 (SEQ ID NO: 64) and CDR3 (SEQ ID NO: 75) regions are delineated and the V and J germline derivations are indicated.

FIG. 4A shows the nucleotide sequence (SEQ ID NO: 102) and amino acid sequence (SEQ ID NO: 38) of the heavy chain variable region of the 3C4 human monoclonal antibody. The CDR1 (SEQ ID NO: 4), CDR2 (SEQ ID NO: 16) and CDR3 (SEQ ID NO: 27) regions are delineated and the V, D and J germline derivations are indicated.

FIG. 4B shows the nucleotide sequence (SEQ ID NO: 113) and amino acid sequence (SEQ ID NO: 87) of the light chain variable region of the 3C4 human monoclonal antibody. The CDR1 (SEQ ID NO: 54), CDR2 (SEQ ID NO: 65) and CDR3 (SEQ ID NO: 76) regions are delineated and the V and J germline derivations are indicated.

FIG. 5A shows the nucleotide sequence (SEQ ID NO: 103) and amino acid sequence (SEQ ID NO: 39) of the heavy chain variable region of the 6A5 human monoclonal antibody. The CDR1 (SEQ ID NO: 5), CDR2 (SEQ ID NO: 17) and CDR3 (SEQ ID NO: 28) regions are delineated and the V, D and J germline derivations are indicated.

FIG. 5B shows the nucleotide sequence (SEQ ID NO: 114) and amino acid sequence (SEQ ID NO: 88) of the light chain variable region of the 6A5 human monoclonal antibody. The CDR1 (SEQ ID NO: 55), CDR2 (SEQ ID NO: 66) and CDR3 (SEQ ID NO: 77) regions are delineated and the V and J germline derivations are indicated.

FIG. 6A shows the nucleotide sequence (SEQ ID NO: 104) and amino acid sequence (SEQ ID NO: 40) of the heavy chain variable region of the 6A8 human monoclonal antibody. The CDR1 (SEQ ID NO: 6), CDR2 (SEQ ID NO: 18) and CDR3 (SEQ ID NO: 29) regions are delineated and the V and J germline derivations are indicated.

FIG. 6B shows the nucleotide sequence (SEQ ID NO: 115) and amino acid sequence (SEQ ID NO: 89) of the light chain variable region of the 6A8 human monoclonal antibody. The CDR1 (SEQ ID NO: 56), CDR2 (SEQ ID NO: 67) and CDR3 (SEQ ID NO: 78) regions are delineated and the V and J germline derivations are indicated.

FIG. 7A shows the nucleotide sequence (SEQ ID NO: 105) and amino acid sequence (SEQ ID NO: 41) of the heavy chain variable region of the 6B10 human monoclonal antibody. The CDR1 (SEQ ID NO: 7), CDR2 (SEQ ID NO: 19) and CDR3 (SEQ ID NO: 30) regions are delineated and the V, D and J germline derivations are indicated.

FIG. 7B shows the nucleotide sequence (SEQ ID NO: 116) and amino acid sequence (SEQ ID NO: 90) of the light chain variable region of the 6B10 human monoclonal antibody. The CDR1 (SEQ ID NO: 57), CDR2 (SEQ ID NO: 68) and CDR3 (SEQ ID NO: 79) regions are delineated and the V and J germline derivations are indicated.

FIG. 8A shows the nucleotide sequence (SEQ ID NO: 106) and amino acid sequence (SEQ ID NO: 42) of the heavy chain variable region of the 7C10 human monoclonal antibody. The CDR1 (SEQ ID NO: 8), CDR2 (SEQ ID NO: 20) and CDR3 (SEQ ID NO: 31) regions are delineated and the V, D and J germline derivations are indicated.

FIG. 8B shows the nucleotide sequence (SEQ ID NO: 117) and amino acid sequence (SEQ ID NO: 91) of the light chain variable region of the 7C10 human monoclonal antibody. The CDR1 (SEQ ID NO: 58), CDR2 (SEQ ID NO: 69) and CDR3 (SEQ ID NO: 80) regions are delineated and the V and J germline derivations are indicated.

FIG. 9A shows the nucleotide sequence (SEQ ID NO: 107) and amino acid sequence (SEQ ID NO: 43) of the heavy chain variable region of the 8F6 human monoclonal antibody. The CDR1 (SEQ ID NO: 9), CDR2 (SEQ ID NO: 21) and CDR3 (SEQ ID NO: 32) regions are delineated and the V, D and J germline derivations are indicated.

FIG. 9B shows the nucleotide sequence (SEQ ID NO: 118) and amino acid sequence (SEQ ID NO: 92) of the light chain variable region of the 8F6 human monoclonal antibody. The CDR1 (SEQ ID NO: 59), CDR2 (SEQ ID NO: 70) and CDR3 (SEQ ID NO: 81) regions are delineated and the V and J germline derivations are indicated.

FIG. 10A shows the nucleotide sequence (SEQ ID NO: 108) and amino acid sequence (SEQ ID NO: 44) of the heavy chain variable region of the 10A12 human monoclonal antibody. The CDR1 (SEQ ID NO: 10), CDR2 (SEQ ID NO: 22) and CDR3 (SEQ ID NO: 33) regions are delineated and the V and J germline derivations are indicated. Alternatively, amino acid residue 32 within CDR1 can be mutated from cysteine to serine (SEQ ID NO: 11), leading to the VH sequence of SEQ ID NO: 45.

FIG. 10B shows the nucleotide sequence (SEQ ID NO: 119) and amino acid sequence (SEQ ID NO: 93) of the light chain variable region of the 10A12 human monoclonal antibody. The CDR1 (SEQ ID NO: 60), CDR2 (SEQ ID NO: 71) and CDR3 (SEQ ID NO: 82) regions are delineated and the V and J germline derivations are indicated.

FIG. 11A shows the nucleotide sequence (SEQ ID NO: 109) and amino acid sequence (SEQ ID NO: 46) of the heavy chain variable region of the 13C4 human monoclonal antibody. The CDR1 (SEQ ID NO: 12), CDR2 (SEQ ID NO: 23) and CDR3 (SEQ ID NO: 34) regions are delineated and the V, D and J germline derivations are indicated.

FIG. 11B shows the nucleotide sequence (SEQ ID NO: 120) and amino acid sequence (SEQ ID NO: 94) of the light chain variable region of the 13C4 human monoclonal antibody. The CDR1 (SEQ ID NO: 61), CDR2 (SEQ ID NO: 72) and CDR3 (SEQ ID NO: 83) regions are delineated and the V and J germline derivations are indicated.

FIG. 12 shows the alignment of the amino acid sequence of the heavy chain variable region of 1D4, 1E1, 2G1, 6A5, 6A8, 7C10 and 10A12 with the human germline $V_H$ 3-33 amino acid sequence (SEQ ID NO: 47).

FIG. 13 shows the alignment of the amino acid sequence of the heavy chain variable region of 6B10 and 8F6 with the human germline $V_H$ 3-30.3 amino acid sequence (SEQ ID NO: 48).

FIG. 14 shows the alignment of the amino acid sequence of the heavy chain variable region of 3C4 with the human germline $V_H$ 5-51 amino acid sequence (SEQ ID NO: 49).

FIG. 15 shows the alignment of the amino acid sequence of the heavy chain variable region of 13C4 with the human germline $V_H$ 4-61 amino acid sequence (SEQ ID NO: 50).

FIG. 16 shows the alignment of the amino acid sequence of the light chain variable region of 1D4, 2G1, 6A5, 6A8, 10A12 and 13C4 with the human germline $V_k$ A27 amino acid sequence (SEQ ID NO: 95).

FIG. 17 shows the alignment of the amino acid sequence of the light chain variable region of 1E1, 6B10 and 8F6 with the human germline $V_k$ L6 amino acid sequence (SEQ ID NO: 96).

FIG. 18 shows the alignment of the amino acid sequence of the light chain variable region of 3C4 with the human germline $V_k$ L18 amino acid sequence (SEQ ID NO: 97).

FIG. 19 shows the alignment of the amino acid sequence of the light chain variable region of 7C10 with the human germline $V_k$ L15 amino acid sequence (SEQ ID NO: 98).

DETAILED DESCRIPTION OF THE INVENTION

The present invention relates to isolated monoclonal antibodies, particularly human monoclonal antibodies, that bind specifically to IP-10 and that inhibit functional properties of IP-10. In certain embodiments, the antibodies of the invention are derived from particular heavy and light chain germline sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunconjugates or bispecific molecules of the invention. The invention also relates to methods of using the antibodies to inhibit inflammatory or autoimmune responses, for example in the treatment of various inflammatory or autoimmune diseases, as well as methods of treating viral infections involving unwanted IP-10 activity.

In order that the present invention may be more readily understood, certain terms are first defined. Additional definitions are set forth throughout the detailed description.

The terms "interferon gamma inducible protein 10" "IP-10," and "CXCL10" are used interchangeably, and include variants, isoforms and species homologs of human IP-10. Accordingly, human antibodies of the invention may, in certain cases, cross-react with IP-10 from species other than human. In other cases, the antibodies may be completely specific for human IP-10 and may not exhibit species or other types of cross-reactivity. The complete amino acid sequence of human IP-10 has Genbank accession number NP_001556 (SEQ ID NO: 121). The complete amino acid sequence of rhesus monkey IP-10 has Genbank accession number AAK95955 (SEQ ID NO: 123). The complete amino acid sequence of mouse IP-10 has Genbank accession number NP_067249 (SEQ ID NO: 124).

The term "CXCR3" refers to the receptor for IP-10 (CXCL10). The complete amino acid sequence of human CXCR3 has Genbank accession number NP_001495 (SEQ ID NO: 122).

The term "MIG" refers to a ligand for CXCR3, also know as monokine induced by gamma interferon, that is distinct from IP-10. The complete amino acid sequence of human MIG has Genbank accession number NP_002407 (SEQ ID NO: 125).

The term "ITAC" refers to a ligand for CXCR3, also known as interferon-inducible T cell alpha chemoattractant, that is distinct from IP-10. The complete amino acid sequence of human ITAC has Genbank accession number NP_005400 (SEQ ID NO: 126).

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the CXCR3 receptor to which the IP-10 molecule binds.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., IP-10). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds IP-10 is substantially free of antibodies that specifically bind antigens other than IP-10). An isolated antibody that specifically binds IP-10 may, however, have cross-reactivity to other antigens, such as IP-10 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human IP-10" is intended to refer to an antibody that binds to human IP-10 with a $K_D$ of $5 \times 10^{-9}$ M or less, more preferably $2 \times 10^{-9}$ M or less, and even more preferably $1 \times 10^{-10}$ M or less. An antibody that "cross-reacts with rhesus monkey IP-10" is intended to refer to an antibody that binds to rhesus monkey IP-10 with a $K_D$ of $0.5 \times 10^{-8}$ M or less, more preferably $5 \times 10^{-9}$ M or less, and even more preferably $2 \times 10^{-9}$ M or less. An antibody that "does not cross-react with mouse IP-10" or "does not cross-react with human MIG" or "does not cross-react with human ITAC" is intended to refer to an antibody that binds to mouse IP-10, human MIG or human ITAC with a $K_D$ of $1.5 \times 10^{-8}$ M or greater, more preferably a $K_D$ of $5-10 \times 10^{-8}$ M or greater and even more preferably $1 \times 10^{-7}$ M or greater. In certain embodiments, such antibodies that do not cross-react with mouse IP-10, human MIG and/or human ITAC exhibit essentially undetectable binding against these proteins in standard binding assays.

As used herein, an antibody that "inhibits binding of IP-10 to CXCR3" is intended to refer to an antibody that inhibits IP-10 binding to CXCR3 with a $K_i$ of 1 nM or less, more preferably 0.75 nM or less, even more preferably 0.5 nM or less and even more preferably 0.25 nM or less.

As used herein, an antibody that "inhibits IP-10 induced calcium flux" is intended to refer to an antibody that inhibits IP-10 induced calcium flux with a $IC_{50}$ of 10 nM or less, more preferably 7.5 nM or less, even more preferably 5 nM or less and even more preferably 2.5 nM or less.

As used herein, an antibody that "inhibits IP-10 induced cell migration" is intended to refer to an antibody that inhibits human IP-10 induced cell migration with a $IC_{50}$ of 2 µg/ml or less, more preferably 1 µg/ml or less, even more preferably 0.5 µg/ml or less and even more preferably 0.25 µg/ml or less.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

Various aspects of the invention are described in further detail in the following subsections.

Anti-IP-10 Antibodies

The antibodies of the invention are characterized by particular functional features or properties of the antibodies. For example, the antibodies bind specifically to human IP-10. Additionally, the antibodies may cross react with IP-10 from one or more non-human primates, such as rhesus monkey. Preferably, the antibodies do not cross react with mouse IP-10. Moreover, although MIG and ITAC are also ligands for the CXCR3 receptor, the antibodies of the invention preferably do not cross react with human MIG or human ITAC.

Preferably, an antibody of the invention binds to IP-10 with high affinity, for example with a $K_D$ of $10^{-8}$ M or less or 10 M or less or even $10^{-10}$ M or less.

Furthermore, the antibodies of the invention are capable of inhibiting one or more functional activities of IP-10. For example, in one embodiment, the antibodies inhibit the binding of IP-10 to CXCR3. In another embodiment, the antibodies inhibit IP-10 induced calcium flux. In yet another embodiment, the antibodies inhibit IP-10 induced cell migration (chemotaxis).

Standard assays to evaluate the binding ability of the antibodies toward IP-10 of various species and/or MIG or ITAC are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of IP-10 (e.g., receptor binding, calcium flux, chemotaxis) are described in further detail in the Examples.

Accordingly, an antibody that "inhibits" one or more of these IP-10 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). Preferably an antibody that inhibits an IP-10 activity effects such a statistically significant decrease by at least 10% of the measured parameter, more preferably by at least 20%, 30%, 40%, 50%, 60%, 70%, 80% or 90%, and in certain preferred embodiments an antibody of the invention may inhibit greater than 92%, 94%, 95%, 97%, 98% or 99% of an IP-10 functional activity.

Monoclonal Antibodies 1D4, 1E1, 2G1, 3C4, 6A5, 6A8, 6B10, 7C10, 8F6, 10A12 and 13C4

Preferred antibodies of the invention are the human monoclonal antibodies 1D4, 1E1, 2G1, 3C4, 6A5, 6A8, 6B10, 7C10, 8F6, 10A12 and 13C4, isolated and structurally characterized as described in Examples 1 and 2. Another preferred antibody is 10A12S, in which amino acid residue 32 of the heavy chain of 10A12 (within $V_H$ CDR1) has been mutated from a cysteine to a serine. The $V_H$ amino acid sequences of 1E1, 2G1, 3C4, 6A5, 6A8, 6B10, 7C10, 8F6, 10A12, 10A12S and 13C4 are shown in SEQ ID NOs: 35-46, respectively. The $V_L$ amino acid sequences of 1E1, 2G1, 3C4, 6A5, 6A8, 6B10, 7C10, 8F6, 10A12 and 13C4 are shown in SEQ ID NOs: 84-94, respectively.

Given that each of these antibodies can bind to IP-10, the $V_H$ and $V_L$ sequences can be "mixed and matched" to create other anti-IP-10 binding molecules of the invention. IP-10 binding of such "mixed and matched" antibodies can be tested using the binding assays described above and in the Examples (e.g., ELISAs). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence. For example, the $V_H$ and $V_L$ sequences of 1D4, 2G1, 6A5, 6A8, 10A12 or 10A12S are particularly amenable for mixing and matching, since these antibodies use $V_H$ and $V_L$ sequences derived from the same germline sequences (VH 3-33 and Vk A27) and thus they exhibit structural similarity. Likewise, the $V_H$ and $V_L$ sequences of 6B10 and 8F6 also are particularly amenable to mixing and matching, since they too use $V_H$ and $V_L$ sequences derived from the same germline sequences (VH 3-30.3 and Vk L6) and thus they exhibit structural similarity. Alternatively, for example, the $V_H$ sequence of 1D4, 2G1, 6A5, 6A8, 10A12 or 10A12S can be paired with the $V_L$ of 13C4, since the $V_H$ sequences of 1D4, 2G1, 6A5, 6A8, 10A12 and 10A12S originally paired with a $V_L$ sequence of germline Vk A27 and the $V_L$ sequence of 13C4 also is derived from germline Vk A27. Likewise, the $V_L$ sequence of 7C10 or 1E1 can be paired with the $V_H$ of 1D4, 2G1, 6A5, 6A8, 10A12 or 10A12S, since the $V_L$ sequences of 7C10 and 1E1 originally paired with a $V_H$ sequence of germline VH 3-33 and the $V_H$ sequences of 1D4, 2G1, 6A5, 6A8, 10A12 and 10A12S also are derived from germline VH 3-33. It will be readily apparent to the ordinarily skilled artisan that other $V_H/V_L$ pairing of structurally similar sequences can be created from the $V_H$ and $V_L$ sequences disclosed herein for monoclonal antibodies 1D4, 1E1, 2G1, 3C4, 6A5, 6A8, 6B10, 7C10, 8F6, 10A12 and 13C4.

Accordingly, in one aspect, the invention provides an isolated monoclonal antibody, or antigen binding portion thereof comprising:

(a) a heavy chain variable region comprising an amino acid sequence selected from the group consisting of SEQ ID NOs: 35-46; and (b) a light chain variable region comprising an amino acid sequence selected from the group consisting of SEQ ID NOs: 84-94;

wherein the antibody specifically binds IP-10.

Preferred heavy and light chain combinations include:

(a) a heavy chain variable region comprising the amino acid sequence of SEQ ID NO: 35; and (b) a light chain variable region comprising the amino acid sequence of SEQ ID NO: 84; or (a) a heavy chain variable region comprising the amino acid sequence of SEQ ID NO: 36; and (b) a light chain variable region comprising the amino acid sequence of SEQ ID NO: 85; or (a) a heavy chain variable region comprising the amino acid sequence of SEQ ID NO: 37; and (b) a light chain variable region comprising the amino acid sequence of SEQ ID NO: 86; or (a) a heavy chain variable region comprising the amino acid sequence of SEQ ID NO: 38; and (b) a light chain variable region comprising the amino acid sequence of SEQ ID NO: 87; or (a) a heavy chain variable region comprising the amino acid sequence of SEQ ID NO: 39; and (b) a light chain variable region comprising the amino acid sequence of SEQ ID NO: 88; or (a) a heavy chain variable region comprising the amino acid sequence of SEQ ID NO: 40; and (b) a light chain variable region comprising the amino acid sequence of SEQ ID NO: 89; or (a) a heavy chain variable region comprising the amino acid sequence of SEQ ID NO: 41; and (b) a light chain variable region comprising the amino acid sequence of SEQ ID NO: 90; or (a) a heavy chain variable region comprising the amino acid sequence of SEQ ID NO: 42; and (b) a light chain variable region comprising the amino acid sequence of SEQ ID NO: 91; or (a) a heavy chain variable region comprising the amino acid sequence of SEQ ID NO: 43; and (b) a light chain variable region comprising the amino acid sequence of SEQ ID NO: 92; or (a) a heavy chain variable region comprising the amino acid sequence of SEQ ID NO: 44 or 45; and (b) a light chain variable region comprising the amino acid sequence of SEQ ID NO: 93; or (a) a heavy chain variable region comprising the amino acid sequence of SEQ ID NO: 46; and (b) a light chain variable region comprising the amino acid sequence of SEQ ID NO: 94.

In another aspect, the invention provides antibodies that comprise the heavy chain and light chain CDR1s, CDR2s and CDR3s of 1D4, 1E1, 2G1, 3C4, 6A5, 6A8, 6B10, 7C10, 8F6, 10A12, 10A12S and 13C4, or combinations thereof. The amino acid sequences of the $V_H$ CDR1s of 1D4, 1E1, 2G1, 3C4, 6A5, 6A8, 6B10, 7C10, 8F6, 10A12, 10A12S and 13C4 are shown in SEQ ID NOs: 1-12. The amino acid sequences of the $V_H$ CDR2s of 1D4, 1E1, 2G1, 3C4, 6A5, 6A8, 6B10, 7C10, 8F6, 10A12 and 13C4 are shown in SEQ ID NOs: 13-23. The amino acid sequences of the $V_H$ CDR3s of 1D4, 1E1, 2G1, 3C4, 6A5, 6A8, 6B10, 7C10, 8F6, 10A12 and 13C4 are shown in SEQ ID NOs: 24-34. The amino acid sequences of the $V_k$ CDR1s of 1D4, 1E1, 2G1, 3C4, 6A5, 6A8, 6B10, 7C10, 8F6, 10A12 and 13C4 are shown in SEQ ID NOs: 51-61. The amino acid sequences of the $V_k$ CDR2s of 1D4, 1E1, 2G1, 3C4, 6A5, 6A8, 6B10, 7C10, 8F6, 10A12 and 13C4 are shown in SEQ ID NOs: 62-72. The amino acid sequences of the $V_k$ CDR1s of 1D4, 1E1, 2G1, 3C4, 6A5, 6A8, 6B10, 7C10, 8F6, 10A12 and 13C4 are shown in SEQ ID NOs: 73-83. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to IP-10 and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, although each antibody must contain a $V_H$ CDR1, 2 and 3 and a $V_L$ CDR1, 2 and 3) to create other anti-IP-10 binding molecules of the invention. IP-10 binding of such "mixed and matched" antibodies can be tested using the binding assays described above and in the Examples (e.g., ELISAs). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). For example, the $V_H$ CDR1s of 1D4, 1E1, 2G1, 6A5, 6A8, 6B10, 7C10, 8F6, 10A12 and 10A12S share some structural similarity and therefore are amenable to mixing and matching, whereas the $V_H$ CDR1s of 3C4 and 13C4 are not structurally similar to the $V_H$ CDR1s of 1D4, 1E1, 2G1, 6A5, 6A8, 6B10, 7C10, 8F6, 10A12 and 10A12S and thus should not be mixed and matched with them. It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 1D4, 1E1, 2G1, 3C4, 6A5, 6A8, 6B10, 7C10, 8F6, 10A12 and 13C4.

Accordingly, in another aspect, the invention provides an isolated monoclonal antibody, or antigen binding portion thereof comprising:

(a) a heavy chain variable region CDR1 comprising an amino acid sequence selected from the group consisting of SEQ ID NOs: 1-12;

(b) a heavy chain variable region CDR2 comprising an amino acid sequence selected from the group consisting of SEQ ID NOs: 13-23;

(c) a heavy chain variable region CDR3 comprising an amino acid sequence selected from the group consisting of SEQ ID NOs: 24-34;

(d) a light chain variable region CDR1 comprising an amino acid sequence selected from the group consisting of SEQ ID NOs: 51-61;

(e) a light chain variable region CDR2 comprising an amino acid sequence selected from the group consisting of SEQ ID NOs: 62-72; and (f) a light chain variable region CDR3 comprising an amino acid sequence selected from the group consisting of SEQ ID NOs: 73-83;

wherein the antibody specifically binds IP-10.

In a preferred embodiment, the antibody comprises:
(a) a heavy chain variable region CDR1 comprising SEQ ID NO: 1;
(b) a heavy chain variable region CDR2 comprising SEQ ID NO: 13;
(c) a heavy chain variable region CDR3 comprising SEQ ID NO: 24;
(d) a light chain variable region CDR1 comprising SEQ ID NO: 51;
(e) a light chain variable region CDR2 comprising SEQ ID NO: 62; and
(f) a light chain variable region CDR3 comprising SEQ ID NO: 73.

In another preferred embodiment, the antibody comprises:
(a) a heavy chain variable region CDR1 comprising SEQ ID NO: 2;
(b) a heavy chain variable region CDR2 comprising SEQ ID NO: 14;
(c) a heavy chain variable region CDR3 comprising SEQ ID NO: 25;
(d) a light chain variable region CDR1 comprising SEQ ID NO: 52;
(e) a light chain variable region CDR2 comprising SEQ ID NO: 63; and
(f) a light chain variable region CDR3 comprising SEQ ID NO: 74.

In another preferred embodiment, the antibody comprises:
(a) a heavy chain variable region CDR1 comprising SEQ ID NO: 3;
(b) a heavy chain variable region CDR2 comprising SEQ ID NO: 15;
(c) a heavy chain variable region CDR3 comprising SEQ ID NO: 26;
(d) a light chain variable region CDR1 comprising SEQ ID NO: 53;
(e) a light chain variable region CDR2 comprising SEQ ID NO: 64; and
(f) a light chain variable region CDR3 comprising SEQ ID NO: 75.

In another preferred embodiment, the antibody comprises:
(a) a heavy chain variable region CDR1 comprising SEQ ID NO: 4;
(b) a heavy chain variable region CDR2 comprising SEQ ID NO: 16;
(c) a heavy chain variable region CDR3 comprising SEQ ID NO: 27;
(d) a light chain variable region CDR1 comprising SEQ ID NO: 54;
(e) a light chain variable region CDR2 comprising SEQ ID NO: 65; and
(f) a light chain variable region CDR3 comprising SEQ ID NO: 76.

In another preferred embodiment, the antibody comprises:
(a) a heavy chain variable region CDR1 comprising SEQ ID NO: 5;
(b) a heavy chain variable region CDR2 comprising SEQ ID NO: 17;
(c) a heavy chain variable region CDR3 comprising SEQ ID NO: 28;

(d) a light chain variable region CDR1 comprising SEQ ID NO: 55;
(e) a light chain variable region CDR2 comprising SEQ ID NO: 66; and
(f) a light chain variable region CDR3 comprising SEQ ID NO: 77.

In another preferred embodiment, the antibody comprises:
(a) a heavy chain variable region CDR1 comprising SEQ ID NO: 6;
(b) a heavy chain variable region CDR2 comprising SEQ ID NO: 18;
(c) a heavy chain variable region CDR3 comprising SEQ ID NO: 29;
(d) a light chain variable region CDR1 comprising SEQ ID NO: 56;
(e) a light chain variable region CDR2 comprising SEQ ID NO: 67; and
(f) a light chain variable region CDR3 comprising SEQ ID NO: 78.

In another preferred embodiment, the antibody comprises:
(a) a heavy chain variable region CDR1 comprising SEQ ID NO: 7;
(b) a heavy chain variable region CDR2 comprising SEQ ID NO: 19;
(c) a heavy chain variable region CDR3 comprising SEQ ID NO: 30;
(d) a light chain variable region CDR1 comprising SEQ ID NO: 57;
(e) a light chain variable region CDR2 comprising SEQ ID NO: 68; and
(f) a light chain variable region CDR3 comprising SEQ ID NO: 79.

In another preferred embodiment, the antibody comprises:
(a) a heavy chain variable region CDR1 comprising SEQ ID NO: 8;
(b) a heavy chain variable region CDR2 comprising SEQ ID NO: 20;
(c) a heavy chain variable region CDR3 comprising SEQ ID NO: 31;
(d) a light chain variable region CDR1 comprising SEQ ID NO: 58;
(e) a light chain variable region CDR2 comprising SEQ ID NO: 69; and
(f) a light chain variable region CDR3 comprising SEQ ID NO: 80.

In another preferred embodiment, the antibody comprises:
(a) a heavy chain variable region CDR1 comprising SEQ ID NO: 9;
(b) a heavy chain variable region CDR2 comprising SEQ ID NO: 21;
(c) a heavy chain variable region CDR3 comprising SEQ ID NO: 32;
(d) a light chain variable region CDR1 comprising SEQ ID NO: 59;
(e) a light chain variable region CDR2 comprising SEQ ID NO: 70; and
(f) a light chain variable region CDR3 comprising SEQ ID NO: 81.

In another preferred embodiment, the antibody comprises:
(a) a heavy chain variable region CDR1 comprising SEQ ID NO: 10 or 11;
(b) a heavy chain variable region CDR2 comprising SEQ ID NO: 22;
(c) a heavy chain variable region CDR3 comprising SEQ ID NO: 33;
(d) a light chain variable region CDR1 comprising SEQ ID NO: 60;
(e) a light chain variable region CDR2 comprising SEQ ID NO: 71; and
(f) a light chain variable region CDR3 comprising SEQ ID NO: 82.

In another preferred embodiment, the antibody comprises:
(a) a heavy chain variable region CDR1 comprising SEQ ID NO: 12;
(b) a heavy chain variable region CDR2 comprising SEQ ID NO: 23;
(c) a heavy chain variable region CDR3 comprising SEQ ID NO: 34;
(d) a light chain variable region CDR1 comprising SEQ ID NO: 61;
(e) a light chain variable region CDR2 comprising SEQ ID NO: 72; and
(f) a light chain variable region CDR3 comprising SEQ ID NO: 83.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

As demonstrated herein, human antibodies specific for IP-10 have been prepared that comprise a heavy chain variable region that is the product of or derived from a human germline VH 3-33 gene, VH 3-30.3 gene, VH 5-51 gene or VH 4-61 gene. Accordingly, the invention provides an isolated monoclonal antibody, or an antigen-binding portion thereof, wherein the antibody comprises a heavy chain variable region that is the product of or derived from a human VH germline gene selected from the group consisting of: VH 3-33, VH 3-30.3, VH 5-51 and VH 4-61. Preferably the antibody is specific for a human IP-10 polypeptide (e.g., comprising the sequence of Genbank Acc. No. NP_001556).

Also as demonstrated herein, human antibodies specific for IP-10 have been prepared that comprise a light chain variable region that is the product of or derived from a human germline Vk A27 gene, Vk L15 gene, Vk L6 gene or Vk L18 gene. Accordingly, the invention provides an isolated monoclonal antibody, or an antigen-binding portion thereof, wherein the antibody comprises a light chain variable region that is the product of or derived from a human Vk germline gene selected from the group consisting of: Vk A27, Vk L15, Vk L6 and Vk L18. Preferably the antibody is specific for a human IP-10 polypeptide (e.g., comprising the sequence of Genbank Acc. No. NP_001556).

Preferred antibodies of the invention are those comprising a heavy chain variable region that is the product of or derived from one of the above-listed human germline VH genes and also comprising a light chain variable region that is the product of or derived from one of the above-listed human germline Vk genes. Accordingly, in antoher embodiment, the invention provides an isolated monoclonal antibody, or an antigen-binding portion thereof, wherein the antibody comprises:
(a) a heavy chain variable region that is the product of or derived from a human VH germline gene selected from the group consisting of: VH 3-33, VH 3-30.3, VH 5-51 and VH 4-61; and
(b) a light chain variable region that is the product of or derived from a human Vk germline gene selected from the group consisting of: Vk A27, Vk L15, Vk L6 and Vk L18. Preferably the antibody is specific for a human IP-10 polypeptide (e.g., comprising the sequence of Genbank Acc. No. NP_001556).

The invention also provides antibodies comprising preferred combinations of heavy and light chain variable regions that are the product of or derived from particular VH and Vk germline genes. For example, in a preferred embodiment, the invention provides an isolated monoclonal antibody, or an antigen-binding portion thereof, wherein the antibody:

(a) comprises a heavy chain variable region that is the product of or derived from a human VH 3-33 gene (which encodes the amino acid sequence set forth in SEQ ID NO: 47;

(b) comprises a light chain variable region that is the product of or derived from a human Vk A27, L15 or L6 gene (which encode the amino acid sequences set forth in SEQ ID NOs: 95, 98 and 97, respectively); and (c) specifically binds to IP-10.

In one embodiment, the antibody comprises a light chain variable region that is the product of or derived from a human Vk A27 gene. Examples of antibodies having $V_H$ and $V_K$ of VH 3-33 and Vk A27, respectively, include 1D4, 2G1, 6A5, 6A8, 10A12 and 10A12S. In another embodiment, the antibody comprises a light chain variable region that is the product of or derived from a human Vk L15 gene. An example of an antibody having $V_H$ and $V_K$ of VH 3-33 and Vk L15, respectively, is 7C10. In another embodiment, the antibody comprises a light chain variable region of a human Vk L6 gene. An example of an antibody having $V_H$ and $V_K$ of VH 3-33 and Vk L6, respectively, is 1E1.

In another preferred embodiment, the invention provides an isolated monoclonal antibody, or an antigen-binding portion thereof, wherein the antibody:

(a) comprises a heavy chain variable region of or derived from a human VH 3-30.3 gene (which encodes the amino acid sequence set forth in SEQ ID NO: 48);

(b) comprises a light chain variable region of or derived from a human Vk L6 gene (which encodes the amino acid sequence set forth in SEQ ID NO: 96); and (c) specifically binds to IP-10.

Examples of antibodies having $V_H$ and $V_K$ of VH 3-30.3 and Vk L6, respectively, include 6B10 and 8F6.

In another preferred embodiment, the invention provides an isolated monoclonal antibody, or an antigen-binding portion thereof, wherein the antibody:

(a) comprises a heavy chain variable region of or derived from a human VH 5-51 gene (which encodes the amino acid sequence set forth in SEQ ID NO:49);

(b) comprises a light chain variable region of or derived from a human Vk L18 gene (which encodes the amino acid sequence set forth in SEQ ID NO: 97); and (c) specifically binds to IP-10.

An example of an antibody having $V_H$ and $V_K$ of VH 5-51 and Vk L18, respectively, is 3C4.

In yet another preferred embodiment, the invention provides an isolated monoclonal antibody, or an antigen-binding portion thereof, wherein the antibody:

(a) comprises a heavy chain variable region of or derived from a human VH 4-61 gene (which encodes the amino acid sequence set forth in SEQ ID NO:50);

(b) comprises a light chain variable region of or derived from a human Vk A27 gene (which encodes the amino acid sequence set forth in SEQ ID NO: 95); and (c) specifically binds to IP-10.

An example of an antibody having $V_H$ and $V_K$ of VH 4-61 and Vk A27, respectively, is 13C4.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-IP-10 antibodies of the invention.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to an amino acid sequence selected from the group consisting of SEQ ID NOs: 35-46;

(b) the light chain variable region comprises an amino acid sequence that is at least 80% homologous to an amino acid sequence selected from the group consisting of SEQ ID NOs:84-94;

(c) the antibody specifically binds to IP-10, and (d) the antibody exhibits at least one of the following functional properties:

(i) the antibody inhibits binding of IP-10 to CXCR3;

(ii) the antibody inhibits IP-10 induced calcium flux;

(iii) the antibody inhibits IP-10 induced cell migration;

(iv) the antibody cross-reacts with rhesus monkey IP-10;

(v) the antibody does not cross-react with mouse IP-10;

(vi) the antibody does not cross-react with human MIG;

(vii) the antibody does not cross-react with human ITAC.

In various embodiments, the antibody may exhibit one or more, two or more, three or more, four or more, five or more or six or more of the functional properties listed as (d) through (j) above. The antibody can be, for example, a human antibody, a humanized antibody or a chimeric antibody.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of SEQ ID NOs: 35-46 and 84-94, respectively, can be obtained by mutagenesis (e.g., site-directed or PCR-mediated mutagenesis) of nucleic acid molecules encoding SEQ ID NOs: 35-46 and/or 84-94, followed by testing of the encoded altered antibody for retained function (i.e., the functions set forth in (c) through (j) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.*

25(17):3389-3402. When utilizing BLAST and Gapped BLAST programs, the default parameters of the respective programs (e.g., XBLAST and NBLAST) can be used. See http://www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 1D4, 1E1, 2G1, 3C4, 6A5, 6A8, 6B10, 7C10, 8F6, 10A12, 10A12S or 13C4), or conservative modifications thereof, and wherein the antibodies retain the desired functional properties of the anti-IP-10 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 24-34, and conservative modifications thereof;

(b) the light chain variable region CDR3 sequence comprises an amino acid sequence selected from the group consisting of amino acid sequence of SEQ ID NOs: 73-83, and conservative modifications thereof;

(c) the antibody specifically binds to IP-10, and (d) the antibody exhibits at least one of the following functional properties:

(i) the antibody inhibits binding of IP-10 to CXCR3;
(ii) the antibody inhibits IP-10 induced calcium flux;
(iii) the antibody inhibits IP-10 induced cell migration;
(iv) the antibody cross-reacts with rhesus monkey IP-10;
(v) the antibody does not cross-react with mouse IP-10;
(vi) the antibody does not cross-react with human MIG;
(vii) the antibody does not cross-react with human ITAC.

In a preferred embodiment, the heavy chain variable region CDR2 sequence comprises an amino acid sequence selected from the group consisting of amino acid sequences of SEQ ID NOs: 13-23, and conservative modifications thereof; and the light chain variable region CDR2 sequence comprises an amino acid sequence selected from the group consisting of amino acid sequences of SEQ ID NOs: 62-72, and conservative modifications thereof. In another preferred embodiment, the heavy chain variable region CDR3 sequence comprises an amino acid sequence selected from the group consisting of amino acid sequences of SEQ ID NOs: 1-12, and conservative modifications thereof; and the light chain variable region CDR3 sequence comprises an amino acid sequence selected from the group consisting of amino acid sequences of SEQ ID NOs: 51-61, and conservative modifications thereof.

In various embodiments, the antibody may exhibit one or more, two or more, three or more, four or more, five or more or six or more of the functional properties listed as (d) through (j) above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

Antibodies that Bind to the Same Epitope as Anti-IP-10 Antibodies of the Invention In another embodiment, the invention provides antibodies that bind to the same epitope as do the various anti-IP-10 antibodies of the invention provided herein, such as other human antibodies that bind to the same epitope as the 1D4, 1E1, 2G1, 3C4, 6A5, 6A8, 6B10, 7C10, 8F6, 10A12, 10A12S or 13C4 antibodies described herein. Such additional antibodies can be identified based on their ability to cross-compete (e.g., to competitively inhibit the binding of, in a statistically significant manner) with other antibodies of the invention, such as 1D4, 1E1, 2G1, 3C4, 6A5, 6A8, 6B10, 7C10, 8F6, 10A12, 10A12S or 13C4, in standard IP-10 binding assays. The ability of a test antibody to inhibit the binding of, e.g., 1D4, 1E1, 2G1, 3C4, 6A5, 6A8, 6B10, 7C10, 8F6, 10A12, 10A12S or 13C4 to human IP-10 demonstrates that the test antibody can compete with that antibody for binding to human IP-10; such an antibody may, according to non-limiting theory, bind to the same or a related (e.g., a structurally similar or spatially proximal) epitope on human IP-10 as the antibody with which it competes. In a preferred embodiment, the antibody that binds to the same epitope on human IP-10 as 1D4, 1E1, 2G1, 3C4, 6A5, 6A8, 6B10, 7C10, 8F6, 10A12, 10A12S or 13C4 is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 1-12, SEQ ID NOs: 13-23 and SEQ ID NOs: 24-34, respectively, and a light chain variable region comprising CDR1, CDR2, and CDR3 sequences comprising an amino acid sequence selected from the group consisting of SEQ ID NOs:51-61, SEQ ID NOs: 62-72 and SEQ ID NOs: 73-83, respectively. Thus, such antibodies contain the $V_H$ and $V_L$ CDR sequences of monoclonal antibodies 1D4, 1E1, 2G1, 3C4, 6A5, 6A8, 6B10, 7C10, 8F6, 10A12, 10A12S or 13C4 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies of the invention are those that are structurally similar to the framework sequences used by selected antibodies of the invention, e.g., similar to the $V_H$ 3-33, 3-30.3, 4-61 or 5-51 sequences [SEQ ID NOS:47-50] and/or $V_k$ A27, L6, L18 or L15 framework sequences [SEQ ID NOS:95-98] used by preferred monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-IP-10 monoclonal antibodies, or antigen binding portions thereof, comprising a heavy chain variable region comprising: (a) a $V_H$ CDR1 region comprising an amino acid sequence selected from the group consisting of SEQ ID NOs: 1-12, or an amino acid sequence having one, two, three, four or five amino acid substitutions, deletions or additions as compared to SEQ ID NOs: 1-12; (b) a $V_H$ CDR2 region comprising an amino acid sequence selected from the group consisting of SEQ ID NOs: 13-23, or an amino acid sequence having one, two, three, four or five amino acid substitutions, deletions or additions as compared to SEQ ID NOs: 13-23; (c) a $V_H$ CDR3 region comprising an amino acid sequence selected from the group consisting of SEQ ID NOs: 24-34, or an amino acid sequence having one, two, three, four or five amino acid substitutions, deletions or additions as compared to SEQ ID NOs: 24-34; (d) a $V_L$ CDR1 region comprising an amino acid sequence selected from the group consisting of SEQ ID NOs: 51-61, or an amino acid sequence having one, two, three, four or five amino acid substitutions, deletions or additions as compared to SEQ ID NOs: 51-61; (e) a $V_L$ CDR2 region comprising an amino acid sequence selected from the group consisting of SEQ ID NOs: 62-72, or an amino acid sequence having one, two, three, four or five amino acid substitutions, deletions or additions as compared to SEQ ID NOs: 62-72; and (f) a $V_L$ CDR3 region comprising an amino acid sequence selected from the group consisting of SEQ ID NOs: 73-83, or an amino acid sequence having one, two, three, four or five amino acid substitutions, deletions or additions as compared to SEQ ID NOs: 73-83.

A preferred substitution mutation of the invention is the substitution of a serine residue for the cysteine residue at position 32, within CDR1, of the $V_H$ chain of the 10A12 mAb. This modified form of 10A12 is referred to herein as 10A12S. The amino acid sequence of the $V_H$ chain of 10A12 is shown in SEQ ID NO: 44 and the amino acid sequence of the $V_H$ chain of 10A12S is shown in SEQ ID NO: 45.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for 6A5, amino acid residue #2 (within FR1) of $V_H$ is a methionine whereas this residue in the corresponding $V_H$ 3-33 germline sequence is a valine (see FIG. 12). To return the framework region sequences to their germline configuration, the somatic mutations can be "backmutated" to the germline sequence by, for example, site-directed mutagenesis or PCR-mediated mutagenesis (e.g., residue 2 of the $V_H$ of 6A5 can be "backmutated" from methionine to valine). Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of $CH_1$ is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol.*

*Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-IP-10 antibodies having $V_H$ and $V_L$ sequences disclosed herein can be used to create new anti-IP-10 antibodies by modifying the VH and/or VL sequences, or the constant region(s) attached thereto. Thus, in another aspect of the invention, the structural features of an anti-IP-10 antibody of the invention, e.g. 1D4, 1E1, 2G1, 3C4, 6A5, 6A8, 6B10, 7C10, 8F6, 10A12, 10A12S or 13C4, are used to create structurally related anti-IP-10 antibodies that retain at least one functional property of the antibodies of the invention, such as binding to human IP-10 and rhesus monkey IP-10, but not to mouse IP-10 or human MIG or human ITAC, and also inhibiting one or more functional properties of IP-10 (e.g., CXCR3 binding, calcium flux, chemotaxis). For example, one or more CDR regions of 1D4, 1E1, 2G1, 3C4, 6A5, 6A8, 6B10, 7C10, 8F6, 10A12, 10A12S or 13C4, or mutations thereof, can be combined recombinantly with known framework regions and/or other CDRs to create additional, recombinantly-engineered, anti-IP-10 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-IP-10 antibody comprising:

(a) providing: (i) a heavy chain variable region antibody sequence comprising a CDR1 sequence selected from the group consisting of SEQ ID NOs: 1-12, a CDR2 sequence selected from the group consisting of SEQ ID NOs: 13-23 and/or a CDR3 sequence selected from the group consisting of SEQ ID NOs: 24-34; and (ii) a light chain variable region antibody sequence comprising a CDR1 sequence selected from the group consisting of SEQ ID NOs: 51-61, a CDR2 sequence selected from the group consisting of SEQ ID NOs: 62-72 and/or a CDR3 sequence selected from the group consisting of SEQ ID NOs: 73-83;

(b) altering at least one amino acid residue within the heavy chain variable region antibody sequence and/or the light chain variable region antibody sequence to create at least one altered antibody sequence; and (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-IP-10 antibodies described herein, which functional properties include, but are not limited to:

(i) specifically binds to human IP-10;
(ii) inhibits binding of IP-10 to CXCR3;
(iii) inhibits IP-10 induced calcium flux;
(iv) inhibits IP-10 induced cell migration;
(v) cross-reacts with rhesus monkey IP-10;
(vi) does not cross-react with mouse IP-10;
(vii) does not cross-react with human MIG; and
(viii) does not cross-react with human ITAC.

The altered antibody may exhibit one or more, two or more, three or more, four or more, five or more, six or more or seven or more of the functional properties set forth as (i) through (viii) above.

The functional properties of the altered antibodies can be assessed using standard assays available in the art and/or described herein, such as those set forth in the Examples (e.g., ELISAs, calcium flux assays, chemotaxis assays).

In certain embodiments of the methods of engineering antibodies of the invention, mutations can be introduced randomly or selectively along all or part of an anti-IP-10 antibody coding sequence and the resulting modified anti-IP-10 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 1D4, 1E1, 2G1, 3C4, 6A5, 6A8, 6B10, 7C10, 8F6, 10A12 or 13C4 monoclonal antibodies. DNA sequences encoding the VH sequences of 1D4, 1E1, 2G1, 3C4, 6A5, 6A8, 6B10, 7C10, 8F6, 10A12 and 13C4 are shown in SEQ ID NOs: 99-109, respectively. DNA sequences encoding the VL sequences of 1D4, 1E1, 2G1, 3C4, 6A5, 6A8, 6B10, 7C10, 8F6, 10A12 and 13C4 are shown in SEQ ID NOs: 110-120, respectively.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against IP-10 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IP-10 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-IP-10 antibodies of the invention. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-IP-10 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of IP-10 antigen and/or recombinant IP-10, or an IP-10 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of IP-10 antigen can be used to immunize the human Ig mice intraperitoneally.

Detailed procedures to generate fully human monoclonal antibodies to IP-10 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-IP-10 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12).

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA*

77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to IP-10 by, for example, standard ELISA. Briefly, microtiter plates are coated with purified IP-10 at 0.25 µg/ml in PBS, and then blocked with 5% bovine serum albumin in PBS. Dilutions of antibody (e.g., dilutions of plasma from IP-10-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with IP-10 immunogen. Hybridomas that bind with high avidity to IP-10 are subcloned and further characterized. One clone from each hybridoma, which retains the reactivity of the parent cells (by ELISA), can be chosen for making a 5-10 vial cell bank stored at −140° C., and for antibody purification.

To purify anti-IP-10 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-IP-10 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using IP-10 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-IP-10 human IgGs can be further tested for reactivity with IP-10 antigen by Western blotting. Briefly, IP-10 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present invention features an anti-IP-10 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine-131, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-IP-10 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for IP-10 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs)), and to target cells expressing IP-10. These bispecific molecules target IP-10 expressing cells to effector cell and trigger Fc receptor-mediated effector cell activities, such as phagocytosis of an IP-10 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-IP-10 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor or target cell antigen. The "anti-enhancement factor portion" can bind an $F_c$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. Fcα RI (CD89) is constitutively expressed on monocytes/macrophages, eosinophilic and neutrophilic granulocytes, but not on non-effector cell populations. FcαRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-IP-10 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) *Behring Ins. Mitt. No.* 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013, 653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoas say (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-IP-10 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-IP-10 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IP-10 antibody of the invention preferably results in a decrease in severity of disease symptoms, an increase in frequency and duration of disease symptom-free periods, or a prevention of impairment or disability due to the disease affliction. In the case of Rheumatoid Arthritis (RA), a therapeutically effective dose preferably prevents further deterioration of physical symptoms associated with RA, such as, for example, pain, fatigue, morning stiffness (lasting more than one hour), diffuse muscular aches, loss of appetite, weakness, joint pain with warmth, swelling, tenderness, and stiffness of a joint after inactivity. A therapeutically effective dose preferably also prevents or delays onset of RA, such as may be desired when early or preliminary signs of the disease are present. Likewise it includes delaying chronic progression associated with RA. Laboratory tests utilized in the diagnosis of RA include chemistries (including the measurement of IP-10 levels), hematology, serology and radiology. Accordingly, any clinical or biochemical assay that monitors any of the foregoing may be used to determine whether a particular treatment is a therapeutically effective dose for treating RA. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) FEBS Lett. 346:123; J. J. Killion; I. J. Fidler (1994) *Immunomethods* 4:273.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. The term "subject" as used herein in intended to includes human and non-human animals. Non-human animals includes all vertebrates, e.g., mammals and non-mammals, such as non-human primates, sheep, dogs, cats, cows, horses, chickens, amphibians, and reptiles. The methods are particularly suitable for treating human patients having a disorder associated with aberrant IP-10 expression. When antibodies to IP-10 are administered together with another agent, the two can be administered in either order or simultaneously.

In one embodiment, the antibodies (and immunoconjugates and bispecific molecules) of the invention can be used to detect levels of IP-10, or levels of cells that contain IP-10. This can be achieved, for example, by contacting a sample (such as an in vitro sample) and a control sample with the anti-IP-10 antibody under conditions that allow for the formation of a complex between the antibody and IP-10. Any complexes formed between the antibody and IP-10 are detected and compared in the sample and the control. For example, standard detection methods, well-known in the art, such as ELISA and flow cytometic assays, can be performed using the compositions of the invention.

Accordingly, in one aspect, the invention further provides methods for detecting the presence of IP-10 (e.g., human IP-10 antigen) in a sample, or measuring the amount of IP-10, comprising contacting the sample, and a control sample, with an antibody of the invention, or an antigen binding portion thereof, which specifically binds to IP-10, under conditions that allow for formation of a complex between the antibody or portion thereof and IP-10. The formation of a complex is then detected, wherein a difference in complex formation between the sample compared to the control sample is indicative of the presence of IP-10 in the sample.

Also within the scope of the invention are kits comprising the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

IP-10 is know to have a chemoattractant effect on activated T cells and NK cells and to recruit such cells to sites of inflammation and autoimmune responses. Accordingly, the anti-IP-10 antibodies (and immunoconjugates and bispecific molecules) of the invention can be used to inhibit inflammatory or autoimmune response mediated by activated T cells and/or NK cells in a variety of clinical indications. The invention, therefore, provides a method of inhibiting an inflammatory or autoimmune response mediated by activated T cells and/or NK cells comprising contacting the T cells or NK cells with an antibody, or antigen-binding portion thereof, of the invention (or immunconjugate or bispecific molecule of the invention) such that the inflammatory or autoimmune response is inhibited. Specific examples of inflammatory or autoimmune conditions in which the antibodies of the invention can be used include, but are not limited to, the following:

A. Multiple Sclerosis and other Demyelinating Diseases

Expression of IP-10 mRNA has been shown to be increased in murine experimental allergic encephalomyelitis (EAE), a mouse model of multiple sclerosis (Godiska, R. et al. (1995) *J. Neuroimmunol.* 58:167-176). Moreover, increased levels of IP-10 have been found in the cerebrospinal fluid of MS patients during acute demyelinating events (Sørensen, T. L. et al. (1999) *J. Clin. Invest.* 103:807-815; Franciotta et al. (2001) *J. Neuroimmunol.* 115:192-198). IP-10 also has been shown to be expressed by astrocytes in MS lesions, but not in unaffected white matter (Balashov, K. E. et al. (1999) *Proc. Natl. Acad. Sci. USA* 96:6873-6878) and to be expressed by macrophages within MS plaques and by reactive astrocytes in the surrounding parenchyma (Simpson, J. E. et al. (2000) *Neuropathol. Appl. Neurobiol.* 26:133-142). PCT Patent Publication WO 02/15932 showed administration of anti-IP-10 antibodies in a mouse hepatitis virus (MHV) model of MS resulted in reduced T lymphocyte and macrophage invasion, inhibited progression of demyelination, increased remyelination and improved neurological function (see also Liu, M. T. et al. (2001) *J. Immunol.* 167:4091-4097). Administration of murine anti-IP-10 antibodies has been shown to decrease clinical and histological disease incidence and severity in murine EAE (Fife, B. T. et al. (2001) *J. Immunol.* 166:7617-7624).

In view of the foregoing, the anti-IP-10 antibodies of the invention can be used in the treatment of MS and other demyelinating diseases by administering the antibody to a subject in need of treatment. The antibody can be used alone or in combination with other anti-MS agents, such as interferon beta-1a (e.g., Avonex®, Rebif®), interferon beta-1b (e.g., Betaseron®), glatiramer acetate (e.g., Copaxone®) and/or mitoxantrone (e.g., Novantrone®).

B. Rheumatoid Arthritis

IP-10 levels have been shown to be significantly elevated in synovial fluid, synovial tissue and serum of patients with rheumatoid arthritis (RA) (Patel, D. D. et al. (2001) *Clin. Immunol.* 98:39-45; Hanaoka, R. et al. (2003) *Arthritis Res. and Therapy* 5:R74-R81). The IP-10 receptor, CXCR3, has been shown to be preferentially expressed on mast cells within synovial tissue from RA patients (Ruschpler, P. et al. (2003) *Arthritis Res. Ther.* 5:R241-R252). In an adjuvant induced arthritis (AA) rat model, a detectable autoantibody response against self IP-10 has been reported (Salomon, I. et al. (2002) *J. Immunol.* 169:2685-2693). Moreover, administration of an IP-10-encoding DNA vaccine augmented production of neutralizing anti-IP-10 antibodies within the rats, and these IP-10 autoantibodies could adoptively transfer resistance to AA to naïve rats (Salomon, I. et al., supra).

In view of the foregoing, the anti-IP-10 antibodies of the invention can be used in the treatment of rheumatoid arthritis by administering the antibody to a subject in need of treatment. The antibody can be used alone or in combination with other anti-RA agents, such as non-steroidal anti-inflammatory drugs (NSAIDs), analgesics, corticosteroids (e.g., prednisone, hydrocortisone), TNF-inhibitors (including adilimumab (Humira®), etanercept (Enbrel®) and infliximab (Remicade®)), disease-modifying anti-rheumatic drugs (including methotrexate, cyclophosphamide, cyclosporine, auranofin, azathioprine, gold sodium thiomalate, hydroxychloroquine sulfate, leflunomide, minocycline, penicillamine and sulfasalazine), fibromyalgia medications, osteoporosis medications and gout medications.

C. Inflammatory Bowel Disease

IP-10 expression has been shown to be significantly enhanced in cells infiltrating the lamina propria of colonic biopsies taken from ulcerative colitis patients (Uguccioni, M. et al. (1999) *Am. J. Pathol.* 155:331-336). Furthermore, neutralization of IP-10 has been shown to protect mice from epithelial ulceration in acute colitis and to enhance crypt cell survival (Sasaki, S. et al. (2002) *Eur. J. Immunol.* 32:3197-3205). Also, in IL-10−/− mice, which develop colitis similar to Crohn's disease in humans, treatment with anti-IP-10 antibodies led to improvement in scoring of inflammation (Singh, U. P. et al. (2003) *J. Immunol.* 171:1401-1406).

In view of the foregoing, the anti-IP-10 antibodies of the invention can be used in the treatment of inflammatory bowel disease (IBD), including ulcerative colitis and Crohn's disease, by administering the antibody to a subject in need of treatment. The antibody can be used alone or in combination with other anti-IBD agents, such as drugs containing mesalamine (including sulfasalazine and other agents containing 5-aminosalicylic acid (5-ASA), such as olsalazine and balsalazide), non-steroidal anti-inflammatory drugs (NSAIDs), analgesics, corticosteroids (e.g., predinisone, hydrocortisone), TNF-inhibitors (including adilimumab (Humira®), etanercept (Enbrel®) and infliximab (Remicade®)), immunosuppressants (such as 6-mercaptopurine, azathioprine and cyclosporine A), and antibiotics.

D. Systemic Lupus Erythematosus

Serum IP-10 levels have been shown to be markedly increased in patients with systemic lupus erythematosus (SLE) and the levels have been shown to correlate with disease activity (see e.g., Narumi, S. et al. (2000) *Cytokine* 12:1561-1565). Accordingly, in another embodiment, the anti-IP-10 antibodies of the invention can be used in the treatment of SLE by administering the antibody to a subject in need of treatment. The antibody can be used alone or in combination with other anti-SLE agents, such as non-steroidal anti-inflammatory drugs (NSAIDs), analgesics, corticosteroids (e.g., predinisone, hydrocortisone), immunosuppressants (such as cyclophosphamide, azathioprine, and methotrexate), antimalarials (such as hydroxychloroquine) and biologic drugs that inhibit the production of dsDNA antibodies (e.g., LJP 394).

E. Type I Diabetes

Serum IP-10 levels have been shown to be elevated in patients with Type I diabetes, particularly those with recent onset disease, and the levels were shown to correlate with the number of GAD-reactive gamma-interferon-producing T cells in patients positive for GAD autoantibodies (Shimada, A. et al. (2001) *Diabetes Care* 24:510-515). In a separate study, serum IP-10 levels were found to be increased in patients with newly diagnosed disease and in patients at high risk for the disease, and IP-10 concentrations correlated with IFN-gamma levels (Nicoletti, F. et al. (2002) *Diabetologia* 45:1107-1110). Moreover, beta cells have been demonstrated to secrete IP-10, leading to chemoattraction of T cells, and mice deficient in CXCR3 have been shown to have delayed onset of Type I diabetes (Frigerio, S. et al. (2002) *Nature Medicine* 8:1414-1420).

Accordingly, in another embodiment, the anti-IP-10 antibodies of the invention can be used in the treatment of Type I diabetes by administering the antibody to a subject in need of treatment. The antibody can be used alone or in combination with other anti-diabetic agents, such as insulin.

F. Inflammatory Skin Disorders

IP-10 expression has been shown to be associated with a variety of inflammatory skin disorders. For example, IP-10 has been detected in keratinocytes and the dermal infiltrate from active psoriatic plaques (Gottlieb, A. B. et al. (1988) *J. Exp. Med.* 168:941-948). Moreover, CXCR3 is expressed by dermal CD3+ lymphocytes, suggesting that CXCR3 is involved in T lymphocyte trafficking to the psoriatic dermis (Rottman, J. B. et al. (2001) *Lab. Invest.* 81:335-347). Accordingly, in another embodiment, the anti-IP-10 antibodies of the invention can be used in the treatment of psoriasis by administering the antibody to a subject in need of treatment. The antibody can be used alone or in combination with other agents or treatments, such as topical treatments (e.g., steroids, coal tar, calcipotriene, tazarotene, anthralin, salicylic acid), phototherapy, systemic medications (e.g., methotrexate, oral retinoids, cyclosporine, fumaric acid esters) and/or biologic drugs (e.g., alefacept, efalizumab).

Lichen planus, a chronic inflammatory disease of the skin and oral mucosa, has been shown to be associated with infiltrating CD4+ and CD8+ T cells that express CXCR3 and, moreover, the CD8+infiltrating cytolytic T cells have to shown to have IP-10 in their cytolytic granules and the lesional keratinocytes have been shown to overexpress IP-10 (Iijima, W. et al. (2003) *Am. J. Pathol.* 163:261-268). Accordingly, in another embodiment, the anti-IP-10 antibodies of the invention can be used in the treatment of lichen planus by administering the antibody to a subject in need of treatment. The antibody can be used alone or in combination with other agents or treatments, such as anti-inflammatory agents, antihistamines, corticosteroids and light therapy.

IP-10 expression has been shown to be elevated in other inflammatory skin disorders, such as chronic discoid lupus erythematosus and Jessner's lymphocytic infiltration of the skin (Flier, J. et al. (2001) *J. Pathol.* 194:398-405). Accordingly, the anti-IP-10 antibodies of the invention can be used in the treatment of these inflammatory skin disorders by administering the antibody to a subject in need of treatment. The antibody can be used alone or in combination with other agents or treatments, as described above.

G. Autoimmune Thyroid Disease

Both IP-10 and CXCR3 have been shown to be expressed in the thyroid gland of patients suffering from Graves' Disease (GD), but not to be expressed (or poorly expressed) in normal thyroid tissue, and expression was highest in patients with recent onset GD (Romagnani, P. et al. (Am. J. Pathol. 161:195-206). IP-10 also has been shown to be expressed in thyroid tissue of patients suffering from Hashimoto's thyroiditis (Kemp, E. H. et al. (2003) Clin. Endocrinol. 59:207-213). Accordingly, in another embodiment, the anti-IP-10 antibodies of the invention can be used in the treatment of autoimmune thyroid disease, including Graves' Disease and Hashimoto's thyroiditis, by administering the antibody to a subject in need of treatment. The antibody can be used alone or in combination with other agents or treatments, such as anti-thyroid drugs, radioactive iodine and subtotal thyroidectomy.

H. Sjogren's Syndrome

The expression of IP-10 mRNA has been shown to be significantly upregulated in the salivary glands of patients with Sjogren's syndrome (SS), with expression being most prominent in the ductal epithelium adjacent to lymphoid infiltrates (see e.g., Ogawa, N. et al. (2002) *Arthritis Rheum.* 46:2730-2741). Accordingly, in another embodiment, the anti-IP-10 antibodies of the invention can be used in the treatment of Sjogren's Syndrome by administering the antibody to a subject in need of treatment. The antibody can be used alone or in combination with other anti-SS agents, such as artificial lubricants (e.g., preservative-free artificial tears, artificial salivas, unscented skin lotions, saline nasal sprays, and vaginal lubricants), Lacriserts® for treatment of dry eyes, pilocarpine hydrochloride (Salagen®) and ceyimeline (Eyoxac®) for treatment of dry mouth, non-steroidal anti-inflammatory drugs (NSAIDs), steroids and immunosuppressive drugs.

I. Pulmonary Inflammation

IP-10 expression has been examined in a mouse model of allergic asthma, with the results demonstrating that IP-10 is upregulated in the lungs after allergen challenge and that overexpression of IP-10 was associated with increased airway hyperactivity, eosinophilia, increased IL-4 levels and recruitment of CD8+ lymphocytes (Medoff, B. D. et al. (2002) *J. Immunol.* 168:5278-5286). Moreover, smokers who develop chronic obstructive pulmonary disease (COPD) have been shown to express IP-10 in their bronchiolar epithelium (Saetta, M. et al. (2002) *Am. J. Respir. Crit. Care Med.* 165: 1404-1409). Still further, high levels of IP-10 have been demonstrated in the bronchoalveolar lavage fluid of patients with pulmonary sarcoidosis and lymphocytic alveolitis (Agostini, C. et al. (1998) *J. Immunol.* 161:6413-6420).

Accordingly, in another embodiment, the anti-IP-10 antibodies of the invention can be used in the treatment of disease characterized by pulmonary inflammation, such as asthma, COPD, pulmonary sarcoidosis or lymphocytic alveolitis, by administering the antibody to a subject in need of treatment. The antibody can be used alone or in combination with other agents for reducing pulmonary inflammation, such as cromolyn sodium, nedocromil sodium, inhaled corticosteroids, systemic (e.g., oral) corticosteroids, short acting beta antagonists, short acting bronchodilators, long acting beta antagonists or agonists (oral or inhaled), leukotriene modifiers, theophylline and oxygen therapy.

J. Transplant Rejection

IP-10 has been shown to play a role in rejection of transplanted tissue. For example, treatment of mice with neutralizing anti-IP-10 antibodies increased the survival of small bowel allografts and reduced accumulation of host T cells and NK cells in the lamina propria (Zhang, Z. et al. (2002) *J. Immunol.* 168:3205-3212). Furthermore, in mice receiving pancreatic islet allografts, anti-IP-10 antibody treatment also resulted in increased allograft survival and decreased lymphocytic graft infiltration (Baker, M. S. et al. (2003) *Surgery* 134:126-133). Additionally, cardiac allografts, but not normal hearts, were shown to express IP-10 and CXCR3, and elevated IP-10 levels were associated with cardiac allograft vasculopathy (Zhao, D. X. et al. (2002) *J. Immunol.* 169: 1556-1560). CXCR3 and IP-10 also have been shown to be expressed by inflammatory cells infiltrating lung allografts (Agostini, C. et al. (2001) *Am J. Pathol.* 158:1703-1711). Neutralization of CXCR3 or IP-10 in vivo was shown to attenuate bronchiolitis obliterans syndrome (BOS), the major limitation to survival for lung transplant recipients, in a murine lung transplant model (Belperio, J. A. et al. (2002) *J. Immunol.* 169:1037-1049).

In view of the foregoing, the invention also provides a method of inhibiting transplant rejection by administering an anti-IP-10 antibody of the invention to a transplant recipient in need of treatment. Examples of tissue transplants that can be treated include, but are not limited to, liver, lung (e.g., treatment of BOS), kidney, heart, small bowel, and pancreatic islet cells. The antibody can be used alone or in combination with other agents for inhibiting transplant rejection, such as immunosuppressive agents (e.g., cyclosporine, azathioprine, methylprednisolone, prednisolone, prednisone, mycophenolate mofetil, sirilimus, rapamycin, tacrolimus), anti-infective agents (e.g., acyclovir, clotrimazole, ganciclovir, nystatin, trimethoprimsulfarnethoxazole), diuretics (e.g., bumetanide, furosemide, metolazone) and ulcer medications (e.g., cimetidine, famotidine, lansoprazole, omeprazole, ranitidine, sucralfate).

K. Spinal Cord Injury

Traumatic injury to the spinal cord leads to infiltration of inflammatory cells. IP-10 has been shown to play a central role in secondary degeneration following spinal cord injury (Gonzalez et al. (2003) *Exp. Neuro/*0.184:456-463; see also PCT patent publication WO 03/06045). IP-10 has been shown to be significantly elevated in the contused rat spinal cords 6 and 12 hours postinjury (McTigue, D. M. et al. (1998) *J. Neurosci. Res.* 53:368-376) and in the injured mouse spinal cord 6 hours post injury (Gonzalez et al. (2003) supra). Accordingly, inhibition of IP-10 activity after spinal cord injury has been shown to be useful in reducing infiltration of inflammatory cells and thus reducing secondary tissue damage to inflammation. Inhibition may also reduce infiltration of inflammatory cells, decrease secondary degeneration and improve recovery following traumatic brain injury and stroke. Thus, the invention also provides a method of treating spinal cord injury and brain injury (e.g., stroke) in a subject in need of treatment comprising administering to the subject an anti-IP-10 antibody of the invention. The antibody can be used alone or in combination with other agents, such as other anti-inflammatory agents.

L. Neurodegenerative Diseases

IP-10 and CXCR3 expression within the central nervous system has been found to be upregulated in association with pathological changes associated with Alzheimer's Disease (AD) (Xia, M. Q. and Hyman, D. T. (1999) *J. Neurovirol.* 5:32-41). Within AD brains, CXCR3 was shown to be expressed constitutively on neurons and neuronal processes in various cortical and subcortical regions and IP-10 was shown to be expressed in astrocytes and its level was markedly elevated as compared to normal brains (Xia, M. Q. et al. (2000) *J. Neuroimmunol.* 108:227-235). Accordingly, the antibodies of the invention can be used in the treatment of neurodegenerative diseases, such as Alzheimer's disease and Parkinson's disease, by administering to a subject in need of treatment the anti-IP-10 antibody, alone or in combination with other therapeutic agents. Examples of agents with which the anti-IP-10 antibody can be combined for Alzheimer's disease treatment include cholinesterase inhibitors (donepezil, rivastigmine, galantamine, tacrine) and vitamin E. An example of an agent with which the anti-IP-10 antibody can be combined for Parkinson's disease treatment is levodopa.

M. Gingivitis

Marginal periodontitis is associated with inflamed gingival tissue. Cells producing IP-10 have been found in inflamed human gingival tissue, as well as cells expressing the CXCR3 receptor (Kabashima, H. et al. (2002) *Cytokine* 20:70-77). Accordingly, in another embodiment, the anti-IP-10 antibodies of the invention can be used in the treatment of gingivitis by administering the antibody to a subject in need of treatment. The antibody can be used alone or in combination with other agents or treatments, such as anti-gingival mouthwashes (e.g., antibiotic mouthwashes), periodontal scaling and root planing and periodontal surgery.

N. Gene Therapy-Associated Inflammation

Replication-deficient adenoviruses, used as adenoviral vectors used in gene therapy, can cause acute injury and inflammation in tissues infected by the viral vectors. Such adenoviral vectors have been shown to induce the expression of IP-10 through capsid-dependent activation of NFkB (Borgland, S. L. et al. (2000) *J. Virol.* 74:3941-3947). Accordingly, the anti-IP-10 antibodies of the invention can be used to inhibit IP-10-induced injury and/or inflammation during gene therapy treatment that utilizes a viral vector, such as an adenoviral vector, that stimulates unwanted production of IP-10.

O. Diseases of Angiogenesis

IP-10 has been shown to inhibit angiogenesis in vitro and in vivo (Strieter et al. (1995) *Biochem. Biophys. Res. Commun.* 210:51-57; Angiolillo et al. (1995) *J. Exp. Med.* 182:155-162; Luster et al. (1995) *J. Exp. Med.* 182:219-231). Angiogenesis plays a crucial role in many disease processes, such as the healing response to trauma. For example, vasculature within the injured spinal cord remains in a state of active remodeling until at least 28 days post injury (Popovich et al. (1997) *J. Comp. Neurol.* 377:443-464).

IP-10 is thought to exert its angiostatic effects through the inhibition of endothelial cell growth and chemotaxis. It does this through its heparin-binding motif as well as through a receptor-mediated mechanism. Through its heparin-binding motif it prevents the angiogenic factors FGF-2 and VEFG165 from binding to their receptors. It also exerts its effects through a receptor-mediated process. The receptor for IP-10, CXCR3, is alternatively spliced to produce the two known variations CXCR3A and CXCR3B. IP-10 binding to the CXCR3A receptor leads to proliferation and chemotaxis of the target cell, whereas IP-10 binding to the CXCR3B receptor has the opposite effect of inhibition of growth and chemotaxis. It is through the CXCR3B receptor that IP-10 acts as an angiostatic factor (Lasagni et al. (2003) *J. Exp. Med.* 197: 1537-1549).

In view of the foregoing, the anti-IP-10 antibodies of the invention can be used in the treatment of diseases requiring angiogenesis, for example where the angiostatic behaviour of IP-10 delays or prevents healing and exacerbates the disease process. Such diseases include: 1) aberrant physiological neovascularization, which may impact wound healing, the female estrus cycle, pregnancy, exercise-induced hypertrophy and the like; 2) indications that may require stimulation of neovascularization, including induction of collateral vessel formation (including myocardial ischemia, peripheral ischemia, cerebral ischemia), coronary artery disease, peripheral vascular disease, stroke, wound healing, engraftment subsequent to organ transplantation such as islet cell transplantation, fracture and tendon repair, reconstructive surgery, tissue engineering, restenosis, hair loss, decubitus and stasis ulcers, gastrointestinal ulcers, placental insufficiency, aseptic necrosis, pulmonary and systemic hypertension, vascular dementia, Alzheimer's Disease, cerebral autosomal dominant arteriopathy with subcortical infarcts and leukoencephalopathy (CADASIL); thyroid psuedocyst and lymphoedema; and 3) indications that may require vascular remodeling, including vascular malformations, psoriasis, and pre-eclampsia. The antibodies of the invention can be used alone or in combination with other angiogenesis inducing agents.

P. Inflammatory Kidney Disease

The CXCR3 receptor has been reported to be expressed by mesangial cells of patients with IgA nephropathy, membranoproliferative glomerulonephritis or rapidly progressive glomerulonephritis (Romagnani, P. et al. (1999) *J. Am. Soc. Nephrol.* 10:2518-2526). Furthermore, in a mouse model of nephrotoxic nephritis, IP-10 mRNA levels were increased six-fold in the cortex of nephritic kidneys 7 days after induction of nephritis (Schadde, E. et al. (2000) *Nephrol. Dial. Transplant.* 15:1046-1053). Still further, high levels of IP-10 expression were observed in kidney biopsy specimens of human patients with glomerulonephritis as compared to normal kidneys (Romagnani, P. et al. (2002) *J. Am. Soc. Nephrol.* 13:53-64). Accordingly, the anti-IP-10 antibodies of the invention can be used in the treatment of inflammatory kidney disease, including IgA nephropathy, memranoproliferative glomerulonephritis and rapidly progressive glomerulonephritis. The antibodies of the invention can be used alone or in combination with other agents or treatments used in the treatment of glomerulonephritis, such as antibiotics, diuretics, high blood pressure medications and dialysis.

Q. Atherosclerosis

IP-10 has been shown to be a mitogenic and chemotactic factor for vascular smooth muscle, which are important features of smooth muscle cells for their contribution to the pathogenesis of atherosclerosis (Wang, X. et al. (1996) *J. Biol. Chem.* 271:24286-24293). IP-10 also has been shown to be induced in smooth muscle cells after treatment with LPS or interferon gamma, and was also induced in the rat carotid artery after balloon angioplasty (Wang, X. et al. (1996) supra). Moreover, IP-10 has been demonstrated to be expressed in atheroma-associated endothelial cells, smooth muscle cells and macrophages, suggesting a role for IP-10 in recruitment and retention of activated T cells that have been observed within vascular wall lesions during atherogenesis (Mach, F. et al. (1999) *J. Clin. Invest.* 104:1041-1050). Accordingly, the anti-IP-10 antibodies of the invention can be used in the treatment or prevention of atherosclerosis. The antibodies can be used alone or in combination with other agents or treatments used in the treatment of atherosclerosis, such high blood pressure medications and cholesterol-lowering drugs.

R. Viral Infections

IP-10 may be upregulated in various viral infections and may play a beneficial role in recruiting activated T cells to fight the viral infection. In certain instances, however, production of IP-10 during viral infection may lead to detrimental effects and thus, the IP-10 activity may be unwanted and it may be desirable to inhibit IP-10 activity in such viral infections using an anti-IP-10 antibody of the invention.

For example, IP-10 has been shown to stimulate replication of human immunodeficiency virus (HIV) in monocyte-derived macrophages and peripheral blood lymphocytes (Lane, B. R. et al. (2003) *Virology* 307:122-134). Furthermore, IP-10 levels are elevated in cerebrospinal fluid and brain of HIV-infected patients and in the central nervous system of HIV gp120-transgenic mice (Asensio, V. C. et al. (2001) *J. Virol.* 75:7067-7077).

IP-10 levels also have been shown to be elevated in patients with chronic persistent hepatitis C virus (HCV) and in patients with chronic active hepatitis (Narumi, S. et al. (1997) *J. Immunol.* 158:5536-5544). In HCV-infected livers, IP-10 was shown to be expressed by hepatocytes but not by other cell types within the liver, and a significantly higher proportion of CXCR3 positive T cells was found in the liver as compared to blood (Harvey, C. E. et al. (2003) *J. Leukoc. Biol.* 74:360-369).

Increased secretion of IP-10 has been shown to be associated with the inflammatory response to acute ocular herpes simplex virus type I (HSV-1) infection in mice, and treatment of HSV-1 infected mice with anti-IP-10 antibodies was shown to reduce mononuclear cell infiltration into the corneal stroma, reduce corneal pathology, and inhibit progression of the virus from the corneal stroma to the retina during acute infection (Carr, D. J. et al. (2003) *J. Virol.* 77:10037-10046).

IP-10 expression also has been shown to be expressed in viral meningitis. IP-10 was demonstrated to be present in the CSF of patients with viral meningitis and to be responsible for chemotactic activity on neutrophils, peripheral blood mononuclear cells and activated T cells (Lahrtz, F. et al. (1997) *Eur. J. Immunol.* 27:2484-2489; Lahrtz, F. et al. (1998) *J. Neuroimmunol.* 85:33-43).

In view of the foregoing, the anti-IP-10 antibodies of the invention can be used in the treatment of viral infections involving unwanted IP-10 activity by administering the antibody to a subject in need of treatment. Non-limiting examples of viral infections that can be treated include HIV (e.g., HIV-induced encephalitis), HCV, HSV-1, viral meningitis and Severe Acute Respiratory Syndrome (SARS). The antibody can be used alone or in combination with other anti-viral agents, such as, for HIV infection, nucleoside/nucleotide reverse transciptase inhibitors, non-nucleoside reverse transciptase inhibitors and/or protease inhibitors (and combinations thereof), for HCV infection, interferon alpha 2a, pegylated interferon alpha 2a, and/or ribavirin, and for HSV-1 infection, acyclovir, valacyclovir and/or famciclovir.

S. Bacterial Infections.

Bacterial infections induce IP-10 production in affected cells (see Gasper, N. A. et al. (2002) *Infect Immun.* 70:4075-82.) Bacterial meningitis is also specifically known to invoke IP-10 expression (Lapinet, J. A. et al. (2000) *Infect Immun.* 68:6917-23). IP-10 is also produced by testicular somatic cells of seminiferous tubules, in a bacterial infection model, strongly indicating a likely role of these chemokines in the accumulation of neutrophils and T lymphocytes during testicular inflammation, which is classically observed in the pathogenesis of bacterial infections (Aubry, F. et al. (2000) *Eur Cytokine Netw.* 11:690-8).

In view of the foregoing, the anti-IP-10 antibodies of the invention can be used in the treatment of bacterial infections involving unwanted IP-10 activity by administering the antibody to a subject in need of treatment. Examples of bacterial infections include, but are not limited to, bacterial meningitis and bacterial pneumonia. The antibody can be used alone or in combination with other anti-bacterial agents, such as antibiotics.

The present invention is further illustrated by the following examples which should not be construed as further limiting. The contents of all figures and all references, patents and published patent applications cited throughout this application are expressly incorporated herein by reference.

Example 1

Generation of Human Monoclonal Antibodies Against IP-10

Antigen

Purified recombinant human IP10 derived from *E. coli* (PeproTech, Inc., Cat number: 300-12), or purified recombinant human IP10 conjugated to keyhole limpet hemocyanin (KLH), was used as the antigen Transgenic HuMab and KM Mice Fully human monoclonal antibodies to IP10 were prepared using HCo7, HCo12 and HCo17 strains of HuMab transgenic mice and the KM strain of transgenic transchromosomic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,545,806; 5,625,825; and 5,545,807. The HCo12 strain carries the HCo12 human heavy chain transgene as described in Example 2 of PCT Publication WO 01/09187. The HCo17 stain carries the HCo17 human heavy chain transgene as described in Example 8 below. The KM strain contains the SC20 transchromosome as described in PCT Publication WO 02/43478.

HuMab and KM Immunizations:

To generate fully human monoclonal antibodies to IP10, HuMab mice and KM mice were immunized with purified recombinant IP10 derived from *E. coli* or IP10-KLH conjugate as antigen. General immunization schemes for HuMab mice are described in Lonberg, N. et al (1994) *Nature* 368 (6474): 856-859; Fishwild, D. et al. (1996) *Nature Biotechnology* 14: 845-851 and PCT Publication WO 98/24884. The mice were 6-16 weeks of age upon the first infusion of antigen. A purified recombinant preparation (5-50 µg) of IP10 antigen (e.g., purified from transfected *E. coli* cells expressing IP10) was used to immunize the HuMab mice and KM mice intraperitonealy, subcutaneously (Sc) or via footpad injection.

Transgenic mice were immunized twice with antigen in complete Freund's adjuvant or Ribi adjuvant either intraperitonealy (IP), subcutaneously (Sc) or via footpad (FP), followed by 3-21 days IP, Sc or FP immunization (up to a total of 11 immunizations) with the antigen in incomplete Freund's or Ribi adjuvant. The immune response was monitored by retroorbital bleeds. The plasma was screened by ELISA (as described below), and mice with sufficient titers of anti-IP10 human immunogolobulin were used for fusions. Mice were boosted intravenously with antigen 3 and 2 days before sacrifice and removal of the spleen. Typically, 10-35 fusions for each antigen were performed. Several dozen mice were immunized for each antigen. A total of 82 mice of the HCo7, HCo12, HCo17 and KM mice strains were immunized with IP10.

Selection of HuMab or KM Mice Producing Anti-IP10 Antibodies:

To select HuMab or KM mice producing antibodies that bound IP10, sera from immunized mice was tested by ELISA as described by Fishwild, D. et al. (1996). Briefly, microtiter plates were coated with purified recombinant IP10 from *E. coli* at 1-2 µg/ml in PBS, 50 µl/wells incubated 4° C. overnight then blocked with 200 µl/well of 5% chicken serum in PBS/Tween (0.05%). Dilutions of plasma from IP10-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Sigma, A-1888, 0.22 mg/ml) and analyzed by spectrophotometer at OD 415-495. Mice that developed the highest titers of anti-IP10 antibodies were used for fusions. Fusions were performed as described below and hybridoma supernatants were tested for anti-IP10 activity by ELISA.

Generation of Hybridomas Producing Human Monoclonal Antibodies to IP10:

The mouse splenocytes, isolated from the HuMab mice and KM mice, were fused with PEG to a mouse myeloma cell line based upon standard protocols. The resulting hybridomas were then screened for the production of antigen-specific antibodies. Single cell suspensions of splenic lymphocytes from immunized mice were fused to one-fourth the number of SP2/0 nonsecreting mouse myeloma cells (ATCC, CRL 1581) with 50% PEG (Sigma). Cells were plated at approximately $1 \times 10^5$/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA (described above) for human anti-IP10 monoclonal IgG antibodies. Once extensive hybridoma growth occurred, medium was monitored usually after 10-14 days. The antibody secreting hybridomas were replated, screened again and, if still positive for human IgG, anti-IP10 monoclonal antibodies were subcloned at least twice by limiting dilution. The stable subclones were then cultured in vitro to generate small amounts of antibody in tissue culture medium for further characterization.

Hybridoma clones 1D4, 1E1, 2G1, 3C4, 6A5, 6A8, 6B10, 7C10, 8F6, 10A12 and 13C4 were selected for further analysis.

Example 2

Structural Characterization of Human Monoclonal Antibodies Against IP-10

The cDNA sequences encoding the heavy and light chain variable regions of the 1D4, 1E1, 2G1, 3C4, 6A5, 6A8, 6B10, 7C10, 8F6, 10A12 and 13C4 monoclonal antibodies were obtained from the corresponding hybridomas using standard PCR techniques and were sequenced using standard DNA sequencing techniques. In cases where DNA sequencing alone was not sufficient to unambiguously determine the antibody structure, protein analysis (e.g., N-terminal amino acid analysis and mass spectroscopy) was also performed and the results compared to the DNA sequence analysis to thereby determine the correct antibody structure. The structural analysis results are as follows:

The nucleotide and amino acid sequences of the heavy chain variable region of 1D4 are shown in FIG. 1A and in SEQ ID NOs: 99 and 35, respectively. The nucleotide and amino acid sequences of the light chain variable region of 1D4 are shown in FIG. 1B and in SEQ ID NOs: 110 and 84, respectively.

The nucleotide and amino acid sequences of the heavy chain variable region of 1E1 are shown in FIG. 2A and in SEQ ID NOs: 100 and 36, respectively. The nucleotide and amino acid sequences of the light chain variable region of 1E1 are shown in FIG. 2B and in SEQ ID NOs: 111 and 85, respectively.

The nucleotide and amino acid sequences of the heavy chain variable region of 2G1 are shown in FIG. 3A and in SEQ ID NOs: 101 and 37, respectively. The nucleotide and amino acid sequences of the light chain variable region of 2G1 are shown in FIG. 3B and in SEQ ID NOs: 112 and 86, respectively.

The nucleotide and amino acid sequences of the heavy chain variable region of 3C4 are shown in FIG. 4A and in SEQ ID NOs: 102 and 38, respectively. The nucleotide and amino acid sequences of the light chain variable region of 3C4 are shown in FIG. 4B and in SEQ ID NOs: 113 and 87, respectively.

The nucleotide and amino acid sequences of the heavy chain variable region of 6A5 are shown in FIG. 5A and in SEQ ID NOs: 103 and 39, respectively. The nucleotide and amino acid sequences of the light chain variable region of 6A5 are shown in FIG. 5B and in SEQ ID NOs: 114 and 88, respectively.

The nucleotide and amino acid sequences of the heavy chain variable region of 6A8 are shown in FIG. 6A and in SEQ ID NOs: 104 and 40, respectively. The nucleotide and amino acid sequences of the light chain variable region of 6A8 are shown in FIG. 6B and in SEQ ID NOs: 115 and 89, respectively.

The nucleotide and amino acid sequences of the heavy chain variable region of 6B10 are shown in FIG. 7A and in SEQ ID NOs: 105 and 41, respectively. The nucleotide and amino acid sequences of the light chain variable region of 6B10 are shown in FIG. 7B and in SEQ ID NOs: 116 and 90, respectively.

The nucleotide and amino acid sequences of the heavy chain variable region of 7C10 are shown in FIG. 8A and in SEQ ID NOs: 106 and 42, respectively. The nucleotide and amino acid sequences of the light chain variable region of 7C10 are shown in FIG. 8B and in SEQ ID NOs: 117 and 91, respectively.

The nucleotide and amino acid sequences of the heavy chain variable region of 8F6 are shown in FIG. 9A and in SEQ ID NOs: 107 and 43, respectively. The nucleotide and amino acid sequences of the light chain variable region of 8F6 are shown in FIG. 9B and in SEQ ID NOs: 118 and 92, respectively.

The nucleotide and amino acid sequences of the heavy chain variable region of 10A12 are shown in FIG. 10A and in SEQ ID NOs: 108 and 44, respectively. The nucleotide and amino acid sequences of the light chain variable region of 10A12 are shown in FIG. 10B and in SEQ ID NOs: 119 and 93, respectively.

The nucleotide and amino acid sequences of the heavy chain variable region of 13C4 are shown in FIG. 11A and in SEQ ID NOs: 109 and 46, respectively. The nucleotide and amino acid sequences of the light chain variable region of 13C4 are shown in FIG. 11B and in SEQ ID NOs: 120 and 94, respectively.

Comparison of the 1D4, 1E1, 2G1, 6A5, 6A8, 7C10 and 10A12 heavy chain immunoglobulin sequences to the known human germline immunoglobulin heavy chain sequences demonstrated that these antibody heavy chains utilizes a $V_H$ segment from human germline $V_H$ 3-33. The alignment of the 1D4, 1E1, 2G1, 6A5, 6A8, 7C10 and 10A12 $V_H$ sequences to the germline $V_H$ 3-33 sequence (SEQ ID NO: 47) is shown in FIG. 12. Further analysis of the 1D4, 1E1, 2G1, 6A5, 6A8, 7C10 and 10A12 VH sequences using the Kabat system of CDR region determination led to the delineation of the heavy chain CDR1, CDR2 and CD3 regions as shown in FIGS. 1A, 2A, 3A, 5A, 6A, 8A and 10A, respectively.

Comparison of the 6B10 and 8F6 heavy chain immunoglobulin sequences to the known human germline immunoglobulin heavy chain sequences demonstrated that these antibody heavy chains utilizes a $V_H$ segment from human germline $V_H$ 3-30.3. The alignment of the 6B10 and 8F6 $V_H$ sequences to the germline $V_H$ 3-33 sequence (SEQ ID NO: 48) is shown in FIG. 13. Further analysis of the 6B10 and 8F6 VH sequences using the Kabat system of CDR region determination led to the delineation of the heavy chain CDR1, CDR2 and CD3 regions as shown in FIGS. 7A and 9A, respectively.

Comparison of the 3C4 heavy chain immunoglobulin sequence to the known human germline immunoglobulin heavy chain sequences demonstrated that this antibody heavy chain utilizes a $V_H$ segment from human germline $V_H$ 5-51. The alignment of the 3C4 $V_H$ sequence to the germline $V_H$ 5-51 sequence (SEQ ID NO: 49) is shown in FIG. 14. Further analysis of the 3C4 VH sequence using the Kabat system of CDR region determination led to the delineation of the heavy chain CDR1, CDR2 and CD3 regions as shown in FIG. 4A.

Comparison of the 13C4 heavy chain immunoglobulin sequence to the known human germline immunoglobulin heavy chain sequences demonstrated that this antibody heavy chain utilizes a $V_H$ segment from human germline $V_H$ 4-61. The alignment of the 13C4 $V_H$ sequence to the germline $V_H$ 4-61 sequence (SEQ ID NO: 50) is shown in FIG. 15. Further analysis of the 13C4 VH sequence using the Kabat system of CDR region determination led to the delineation of the heavy chain CDR1, CDR2 and CD3 regions as shown in FIG. 11A.

Comparison of the 1D4, 2G1, 6A5, 6A8, 10A12 and 13C4 light chain immunoglobulin sequences to the known human germline immunoglobulin light chain sequences demonstrated that these antibody light chains utilizes a $V_L$ segment from human germline $V_k$ A27. The alignment of the 1D4, 2G1, 6A5, 6A8, 10A12 and 13C4 $V_L$ sequences to the germline $V_K$ A27 sequence (SEQ ID NO: 95) is shown in FIG. 16. Further analysis of the 1D4, 2G1, 6A5, 6A8, 10A12 and 13C4 $V_L$ sequences using the Kabat system of CDR region determination led to the delineation of the light chain CDR1, CDR2 and CD3 regions as shown in FIGS. 1B, 3B, 5B, 6B, 10B and 11B, respectively.

Comparison of the 1E1, 6B10 and 8F6 light chain immunoglobulin sequences to the known human germline immunoglobulin light chain sequences demonstrated that these antibody light chains utilizes a $V_L$ segment from human germline $V_k$ L6. The alignment of the 1E1, 6B10 and 8F6 $V_L$ sequences to the germline $V_K$ L6 sequence (SEQ ID NO: 96) is shown in FIG. 17. Further analysis of the 1E1, 6B10 and 8F6 $V_L$ sequences using the Kabat system of CDR region determination led to the delineation of the light chain CDR1, CDR2 and CD3 regions as shown in FIGS. 2B, 7B and 9B, respectively.

Comparison of the 3C4 light chain immunoglobulin sequence to the known human germline immunoglobulin light chain sequences demonstrated that the 3C4 light chain utilizes a $V_L$ segment from human germline $V_k$ L18. The alignment of the 3C4 $V_L$ sequence to the germline $V_k$ L18 sequence (SEQ ID NO: 97) is shown in FIG. 18. Further analysis of the 3C4 $V_L$ sequence using the Kabat system of CDR region determination led to the delineation of the light chain CDR1, CDR2 and CD3 regions as shown in FIG. 4B.

Comparison of the 7C10 light chain immunoglobulin sequence to the known human germline immunoglobulin light chain sequences demonstrated that the 7C10 light chain utilizes a $V_L$ segment from human germline $V_k$ L15. The alignment of the 7C10 $V_L$ sequence to the germline $V_k$ L15 sequence (SEQ ID NO: 98) is shown in FIG. 19. Further analysis of the 7C10 $V_L$ sequence using the Kabat system of CDR region determination led to the delineation of the light chain CDR1, CDR2 and CD3 regions as shown in FIG. 8B.

Example 3

Characterization of Binding Specificity and Binding Kinetics of Anti-IP-10 Human Monoclonal Antibodies In this example, binding affinity, binding kinetics and binding specificity of anti-IP-10 antibodies were examined by Biacore analysis. Also, binding specificity and cross-competition was examined by ELISA.

Biacore Analysis

Anti-IP-10 antibodies were characterized for affinities and binding kinetics by Biacore analysis (Biacore AB, Uppsala, Sweden). *E. coli*-expressed, purified recombinant human IP-10 (R& D Systems) was coupled to the CM5 sensor chip @ 97 RU using the EDC/NHS coupling protocol provided by Biacore AB. Binding was measured by flowing the antibody in HBS EP buffer (provided by Biacore AB) at concentrations from 33-267 nM at a flow rate of 40 μl/min. The antigen-antibody association kinetics was followed for 5 minutes and the dissociation kinetics was followed for 8 minutes. The association and dissociation curves were fit to a 1:1 Langmuir binding model using BIAevaluation software (Biacore AB). Data corresponding to the initial few dozen seconds for association and dissociation phases alone were considered for curve fitting to minimize the effect of avidity. The experiments were performed at both 25° C. and 37° C. The $K_D$, $k_{on}$ and $k_{off}$ values that were determined are shown in Table 1 for binding at 25° C. and in Table 2 for binding at 37° C.:

TABLE 1

Binding Characterization at 25° C. with Human IP-10

| Clone ID | Affinity $K_D \times 10^{-9}$ (M) | On rate $K_{on} \times 10^4$ (1/Ms) | Off rate $K_{off} \times 10^{-5}$ (1/s) |
| --- | --- | --- | --- |
| 7C10 | 0.02 | 1.70 | 0.04 |
| 10A12 | 0.53 | 3.83 | 2.02 |
| 8F6 | 0.81 | 23.3 | 19.0 |
| 10A12S | 0.88 | 3.68 | 3.24 |
| 6A5 | 1.20 | 3.11 | 3.64 |
| 6A5 Batch 2* | 0.96 | 3.20 | 3.10 |
| 1D4 | 1.20 | 8.40 | 10.20 |
| 6B10 | 1.78 | 9.50 | 17.2 |
| 2G1 | 1.90 | 3.78 | 0.75 |

*6A5 Batch 2 is an independent sample of purified antibody from the 6A5 hybridoma supernatant as compared to sample 6A5.

TABLE 2

Binding Characterization at 37° C. with Human IP-10

| Clone ID | Affinity $K_D \times 10^{-9}$ (M) | On rate $K_{on} \times 10^4$ (1/Ms) | Off rate $K_{off} \times 10^{-5}$ (1/s) |
| --- | --- | --- | --- |
| 7C10 | 0.016 | 5.27 | 0.08 |
| 10A12 | 0.34 | 11.1 | 3.81 |
| 8F6 | 0.78 | 34.7 | 27.0 |
| 10A12S | 0.49 | 9.10 | 4.43 |
| 6A5 | 0.70 | 10.2 | 7.15 |
| 6A5 Batch 2 | 0.74 | 8.41 | 6.26 |
| 1D4 | 1.15 | 16.6 | 19.2 |
| 6B10 | 2.54 | 19.9 | 50.4 |
| 2G1 | 0.34 | 14.8 | 4.97 |

The half-life of the antibodies (in hours), as defined by the time taken for the dissociation of half of the antibody-antigen complex during the dissociation phase, was measured at 25° C. and 37° C. The values were determined by extension of the dissociation curves to get to the time required for the 50% reduction of the Y-axis of the dissociation sensogram. The results are shown below in Table 3:

TABLE 3

Half-Life of Antibodies at 25° C. and 37° C.

| Clone ID | Half-life (in hours) at 25° C. | Half-life (in hours) at 37° C. |
|---|---|---|
| 2G1 | 25.67 | 3.87 |
| 10A12 | 9.53 | 5.05 |
| 10A12S | 5.94 | 4.34 |
| 6A5 | 5.29 | 2.69 |
| 6A5 Batch 2 | 6.21 | 3.87 |
| 1D4 | 1.88 | 1.00 |
| 6B10 | 1.12 | 0.38 |
| 8F6 | 1.01 | 0.71 |

The cross-reactivity of the antibodies, at 25° C., with rhesus monkey IP-10, human MIG, human ITAC and mouse IP-10 was determined by Biacore analysis using the same methods as described above for human IP-10. Human MIG, human IP-10 and mouse IP-10 were obtained commercially (PeproTech, Rocky Hill, N.J.), whereas rhesus monkey IP-10 was made by recombinant expression and purified by standard methods. The antigens were conjugated to the CM5 sensor chip @ 140 RUs (rhesus monkey IP-10), 457 RUs (human MIG), 206 RUs (human ITAC) and 150 RUs (mouse IP-10). Association sensograms were obtained by flowing antibodies in HBS EP buffer at a concentration of 133 nM for 5 minutes. The flow was then stopped and dissociation was monitored for 5 minutes. The association and dissociation curves were fit to a Langmuir binding model using BIAevaluation software (Biacore AB). The results of the cross-reactivity experiments are summarized below in Table 4:

TABLE 4

Anti-IP-10 Cross Reactivity with Various CXCR3 Ligands

| Clone ID | Rhesus IP-10 $K_D \times 10^{-9}$ (M) | Human MIG $K_D \times 10^{-9}$ (M) | Human ITAC $K_D \times 10^{-9}$ (M) | Mouse IP-10 $K_D \times 10^{-9}$ (M) |
|---|---|---|---|---|
| 7C10 | 4.4 | 105.0 | No binding | 464.0 |
| 10A12 | 0.71 | 161.0 | No binding | No binding |
| 8F6 | 0.81 | No binding | No binding | No binding |
| 10A12S | 1.21 | 722.0 | No binding | No binding |
| 6A5 | 1.06 | No binding | No binding | No binding |
| 6A5 Batch 2 | 1.23 | No binding | No binding | No binding |
| 1D4 | 0.94 | No binding | No binding | No binding |
| 6B10 | 2.01 | 15.4 | 51.5 | 105.0 |
| 2G1 | 0.26 | 70.1 | No binding | No binding |

ELISA Analysis

Additional experiments were performed using an ELISA assay to examine the antigenic cross-reactivity of the anti-IP-10 antibodies for human MIG, rhesus monkey IP-10 or mouse IP-10. The procedures used for the ELISA was as described above in Example 1 except that the microtiter plates were coated with 1 µg/ml of either recombinant human IP-10, human MIG (PeproTech, cat. #300-26), mouse IP-10 (PeproTech, cat. #250-16) or recombinant rhesus monkey IP-10. The results, expressed as $EC_{50}$ values (in ng/ml) are summarized below in Table 5:

TABLE 5

Anti-IP-10 Cross Reactivity by ELISA with Various CXCR3 Ligands

| Clone ID | Human IP-10 ($EC_{50}$ ng/ml) | Monkey IP-10 ($EC_{50}$ ng/ml) | Human MIG ($EC_{50}$ ng/ml) | Mouse IP-10 |
|---|---|---|---|---|
| 10A12 | 40 | 80 | 180 | No binding |
| 10A12S | 4.9 | 15.6 | 380 | No binding |
| 2G1 | 30 | 30 | 45 | No binding |
| 6A5 | 35 | 90 | No binding | No binding |
| 6A5 Batch 2 | 62 | 125 | No binding | No binding |
| 6B10 | 30 | 45 | 20 | No binding |
| 8F6 | 90 | 31 | No binding | No binding |
| 1D4 | 25 | 62 | No binding | No binding |

Cross-competition studies between the various anti-IP-10 antibodies were also performed by ELISA using biotinylated forms of 6A5 and 2G1 to determine whether the antibodies recognize different epitopes on IP-10. The procedure for competition ELISAs was similar to the ELISA described above in Example 1. Briefly, microtiter plates were coated with purified recombinant IP-10 from E. coli at 0.2 µg/ml in PBS, 50 µl/well and incubated 4° C. overnight. The wells then were blocked with 200 µl/well of 5% chicken serum in PBS/Tween (0.05%). Dilutions of purified human anti-human IP-10 antibodies (from 2 µg/ml to 3.91 ng/ml) were added to each well and incubated for 30 minutes at ambient temperature. The plates were washed with PBS/Tween and then incubated with 0.1 µg/ml of biotin-6A5 or biotin-2G1 for 30 minutes. The plates were then washed three times with PBS/Tween. After washing, phosphatase labeled streptavidin (KPL, Cat #: 15-30-00) was added at 1:2000 dilution in 5% chicken serum to each well and incubated for 1 hour at room temperature. After washing, the plates were developed with p-NPP substrate (Moss, Inc, lot 10274021) and analyzed by spectrophotometer at OD 405. As expected, unlabeled 2G1 could compete with biotin-2G1 for binding to IP-10 and, moreover, unlabeled 6A5, 7C10, 10A12, 10A12S, 6B10, 8F6 and 1D4 were each capable of competing the binding of biotin-2G1 to human IP-10. Similarly, unlabeled 6A5 could compete with biotin-6A5 for binding to IP-10 and, moreover, unlabeled 2G1, 7C10, 10A12, 10A12S, 6B10, 8F6 and 1D4 were each capable of competing the binding of biotin-6A5 to human IP-10. These results indicate that each of these antibodies have a binding specificity for the same epitope (or epitope group) of human IP-10.

Example 4

Inhibition of IP-10 Binding to CXCR3

In this example, the ability of anti-IP-10 antibodies to inhibit the binding of human IP-10 to its receptor, CXCR3, on receptor-expressing cells was examined. First, a Scatchard analysis was performed for $^{125}$I-IP-10 binding to 300.19 cells transfected to express CXCR3. The cells were grown in RPMI media containing 10% FCS and G418 selection. Prior to use, the cells were washed twice with Hank's Balanced Salt Solution (HBSS) at 4° C. and adjusted to $4 \times 10^7$ cells/ml. Glass fiber plates (Millipore MultiScreen®, Cat. #MAFBN0B50) were blocked with 200 µl of a 0.1% polyethyleneimine solution one day prior to the experiment. On the day of the study, the blocking buffer was aspirated by using a Millipore manifold. The plates were washed three times with 200 µl of binding buffer (50 mM HEPES, pH 7.2, 1 mM $CaCl_2$, 5 mM $MgCl_2$, 0.5% BSA). Twenty-five microliters of binding buffer was added to each well followed by either 25 µl of 1000 fold excess unlabeled IP-10 or binding buffer. Twenty-five microliters of $^{125}$I-IP-10 (Amersham, Cat. #IM332-25 µCi) at increasing concentrations was added, followed by 25 µl of cells at a density of 1×10$^6$ cells per well. The plates were incubated on a plate shaker for 60 minutes at room temperature and washed three times with wash buffer (10 mM HEPES, pH 7.2, 0.5 M NaCl, 0.5% BSA) at a volume of 200 µl per wash. The plates were dried, 25 µl of scintillant was added and the plates were counted on a Wallac Microbeta Counter. Data were analyzed using Prism software and a $K_D$ was calculated. A mean $K_D$ of 0.231 nM was determined for receptor binding.

Next, the ability of the anti-IP-10 antibodies to inhibit the binding of 100 pM-$^{125}$I-hIP-10 to the CXCR3-expressing cells was examined. Competition assays were run in a similar manner to the experiment described above. Briefly, 25 µl of binding buffer was added to the glass fiber filter plates, followed by 25 µl of increasing concentrations of anti-IP-10 antibodies. Twenty-five microliters of $^{125}$I-IP-10 was added to a final concentration of 0.100 nM. Lastly, 25 µl of cells at a density of 1×10$^6$ cells per well were added and the plates were incubated on a plate shaker for 60 minutes at room temperature, washed and counted as described above. $EC_{50}$ values were calculated using Prism software. $K_i$ values (in nM) were determined using the formula:

$$K_i = \frac{EC_{50}}{1 + [L]/K_D}$$

The results are summarized below in Table 6:

TABLE 6

Inhibition of IP-10 Binding to CXCR3

| Clone ID | Ki (nM) |
|---|---|
| 10A12 | 0.09 |
| 10A12S | 0.06 |
| 2G1 | 0.09 |
| 8F6 | 0.16 |
| 1E1 | 0.29 |
| 6B10 | 0.30 |
| 7C10 | 0.41 |
| 6A5 | 0.67 |
| 6A5 Batch 2 | 0.35 |
| 1D4 | 0.86 |

Example 5

Inhibition of IP-10 Induced Calcium Flux

In this example, the ability of anti-IP-10 antibodies to inhibit IP-10-induced calcium flux was examined using either 300.19 cells transfected to express CXCR3 or anti-CD3 activated human peripheral blood lymphocytes (PBLs) that express CXCR3. To prepare the PBLs, normal human blood was purified by standard Ficoll separation. The purified human PBLs were stimulated by adding the cells to plates coated with 3 µg/ml of anti-CD3 antibody and grown in RPMI with 10% FBS. Following a three day incubation, the cells were maintained in growth media containing 500 U/ml of IL-2. On the day of the study, the cells were washed and resuspended in media at a density of 2.5×10$^7$ cells/ml. The 300.19 cells transfected to express CXCR3 were grown in RPMI containing 10% FBS. The 300.19 cells were resuspended in growth media at 2×10$^6$ cells/ml.

To perform the assay, 100 µl of cell suspension was added to a black-sided, clear-bottomed 96 well plate which was coated with Poly-D-Lysine (Corning/Costar, cat. #3667). 100 microliters of Calcium 3 kit loading dye (FlexStation™, Molecular Devices, Inc., Sunnyvale, Calif.) was added to each well, the plates were spun at 1100 RPM for 4 minutes and incubated at 37° C. for 30 minutes. Using a 96-well reagent plate, human IP-10 (Peprotech, cat. #300-12) was diluted in Hank's Balanced Salt Solution with 20 mM HEPES and 1% FBS (800 pM for 300.19 cells and 1200 pM for human PBLs). Antibodies were serially diluted in the reagent plates containing IP-10. Control wells containing buffer alone or IP-10 alone were included. Twenty-two microliters of IP-10/antibody solution were added per well to the plates containing the dye labeled cells and calcium flux was determined by monitoring Calcium 3 fluorescence using the FlexStation™ instrument according to the manufacturer's instructions, over a time period of 200 seconds. The area under the curve (AUC) was calculated by the integration of the calcium flux between 20-100 seconds according to standard protocols (see e.g., Smart D. et al. (1999) *Br. J. Pharmacol.* 128:1-3). The data were analyzed using Prism™ software (Molecular Devices, Inc.) and $IC_{50}$ values (in nM) were determined. The results are summarized below in Table 7:

TABLE 7

Inhibition of IP-10-Induced Calcium Flux

| Clone ID | IC$_{50}$ (nM) for HPBL | IC$_{50}$ (nM) for 300.19 Cells |
|---|---|---|
| 10A12 | 1.25 | 0.18 |
| 10A12S | 2.31 | 0.08 |
| 2G1 | 2.98 | 0.50 |
| 8F6 | 6.27 | 0.30 |
| 1E1 | 3.64 | NT |
| 6B10 | 4.40 | 0.50 |
| 7C10 | 8.15 | 0.77 |
| 6A5 | 2.85 | 0.61 |
| 6A5 Batch 2 | 2.18 | 0.42 |
| 1D4 | 4.07 | 0.34 |

Example 6

Inhibition of IP-10 Induced Cell Migration

The ability of anti-IP-10 antibodies to inhibit cell migration induced by IP-10 was examined in an in vitro chemotaxis assay. In a these experiments, CXCR3-expressing 300.19 cells were used and were stimulated with either: (i) 100 ng/ml of recombinant human IP-10 (rhIP-10); (ii) supernatant of THP-1 cells stimulated with IFN gamma (which induces secretion of native IP-10 and MIG), wherein THP-1 derived IP-10 was at a concentration of 16 ng/ml and MIG activity was blocked by addition of anti-MIG (R&D Systems) at 2.5 µg/ml; or (iii) 100 ng/ml recombinant rhesus macaque IP-10 (rrmIP-10). Inhibition of cell migration was assessed using various concentrations of antibodies and a chemotactic index was determined.

Specifically, chemotaxis inhibition was assessed using a standard 96 well plate assay (Multiscreen MIC plates (Millipore)). A 5 µm filter was used for transfected cell lines; and 3 µm filter was used for primary cells. Responding cells (300.19 CXCR3+; MBP-specific human PBMC cells) were resuspended in chemotaxis buffer (RPMI+1% BSA or FBS) at 1×10$^6$ cells/ml. 100 µl of cell suspension was added to the upper well and left to incubate for 30 minutes at 37° C. 5% $CO_2$ was applied prior to addition to the bottom well.

Human and rhesus macaque IP-10 was prepared at 100 ng/ml; for THP-1 derived IP-10, THP-1 cells were stimulated with IFN-γ (0.2 ng/ml) and supernatant was collected; MS CSF derived IP-10 was used neat. Ligand was prepared in 150 μL of chemotaxis buffer and placed in the lower chamber.

For chemotaxis inhibition assays, ligand was pre-incubated with varying concentrations of the indicated anti-IP-10 antibody (5 μg/ml, 2.5 m/ml, 1.25 m/ml, 0.613 m/ml, 0.3 m/ml, 0.015 m/ml) for 30 minutes at 37° C. in 5% CO2 prior to assay. The top chamber was placed over wells, and the wells were incubated for 2 hours at 37° C. in 5% CO2. At the end of the incubation, responding cells were aspirated from the top chamber. The top chamber was carefully removed. Cells were counted in 4 random fields/well at 400× magnification. Data was averaged across three wells and presented as a chemotaxis index (i.e. the fold migration in response to ligand over media alone).

The results, expressed as $IC_{50}$ values, are summarized below in Table 8:

TABLE 8

Inhibition of IP-10 Induced Cell Migration

| Clone ID | rhIP-10 $IC_{50}$ (μg/ml) | THP-1 IP-10 $IC_{50}$ (μg/ml) | rmIP-10 $IC_{50}$ (μg/ml) |
|---|---|---|---|
| 6A5 (Batch 2) | 0.156 | 0.132 | 0.119 |
| 8F6 | 0.355 | 0.173 | 0.100 |
| 6B10 | 1.1 | 0.193 | 0.149 |
| 10A12S | 0.115 | 0.211 | 15.1 |
| 1D4 | 0.156 | 0.247 | 0.163 |

The ability of anti-IP-10 antibodies to inhibit CXCR3-expressing 300.19 cell migration in response to cerebrospinal fluid (CSF) from multiple sclerosis (MS) patients was also examined. Again, anti-MIG antibody at 2.5 μg/ml was added to the CSF sample to neutralize MIG activity. The results from two experiments, expressed as $IC_{50}$ values, are summarized below in Table 9:

TABLE 9

Inhibition of MS-CSF Induced Cell Migration

| Clone ID | Expt. 1 $IC_{50}$ (μg/ml) | Expt. 2 $IC_{50}$ (μg/ml) |
|---|---|---|
| 6A5 (Batch 2) | 0.100 | 0.236 |
| 10A12S | 0.562 | 0.577 |

Cell migration studies were also performed using CXCR3-expressing 300.19 cells and recombinant human MIG (R&D Systems), at 200 ng/ml, to examine the ability of the anti-IP-10 antibodies to inhibit MIG-induced cell migration. The anti-IP-10 antibodies 6B10, 8F6, 1D4, 6A5 batch 2, 10A12 and 10A12S were individually tested at 1 μg/ml and were found not to inhibit the MIG-induced cell migration.

Example 7

Binding of Antibodies to Brain Section of MS Patients

In this example, the ability of anti-IP-10 antibodies to stain brain sections from a multiple sclerosis (MS) patient was examined. Brain sections from a 57 year old female MS patient were obtained 19.8 hours post-mortem and showed an irregular shaped periventricular plaque (1.3 cm×1.0 cm) with numerous additional smaller plaques present throughout the remaining white matter. LFB staining showed complete demyelination. Immunohistochemistry was performed on the sections using the 6A5 (batch 2) and 10A12S anti-IP-10 antibodies, as well as anti-GFAP and anti-CD68, as positive controls, and a negative control antibody.

A standard immunohistochemistry protocol was employed for anti-IP-10 staining of the sections. Sections were blocked using 2%-10% serum. 100 μl/section primary antibody (e.g., 6A5) diluted 1:100 in 2% serum was added, then incubated 1 hr at RT. Optionally, sections were incubated overnight at 4° C. and washed. The secondary anti-human biotinylated antibody (diluted in 2% serum (100 μl/section)) was then added and incubated 30-60 minutes at RT. Endogenous peroxidases were removed by adding dilute $H_2O_2$ in MeOH. Next, ABC Solution (Vector Labs) was added, 100 μl/section, and incubated for 30 mins RT. DAB substrate solution was prepared immediately prior to use. 100 μl per section was applied to slides before incubating in the dark for 10-20 mins (as necessary for development). Slides were then counterstained with Hematoxylin nuclear stain for 3 min (Progress checked after 1 min). Finally slides were incubate in 2% sodium bicarbonate for 45 seconds to bring out the colour.

The results showed that both 6A5 and 10A12S could bind to IP-10 in situ in the brain sections of the MS patient, with 6A5 staining being more intense than 10A12S staining.

Example 8

Construction of HCo17 Strain of Transgenic Mice

The HCo17 transgenic mouse strain was generated by coinjection of the 80 kb insert of pHC2 (Taylor et al. (1994) *Int. Immunol.,* 6: 579-591), the 25 Kb insert of pVX6, and a ~460 kb yeast artificial chromosome fragment of the yIgH24 chromosome. The pHC2 construct alone is fully capable of being rearranged in vivo to form functional human heavy chain immunoglobulin loci; pVX6 and yIgH24 were added to contribute additional germline $V_H$ diversity. The individual components of the DNA mixture used to produce HCo17 are described below.

The pHC2 insert described above contains four functional human germline $V_H$ gene segments: 1-69 (DP-10), 5-51 (DP-73), 4-34 (DP-63), and 3-30.3 (DP-46). In addition, this construct also contains human genomic sequences comprising 15 functional D segments, all 6 J segments, as well μ and γ1 constant region segments and a functional μ-γ1 switch region.

The pVX6 insert contains 3 human germline VH segments, VH1-18 (DP-14), VH5-51 (DP-73) and VH3-23 (DP-47). An 8.5 kb HindIII/SalI DNA fragment, comprising the germline human VH1-18 (DP-14) gene, together with approximately 2.5 kb of 5' flanking, and 5 kb of 3' flanking genomic sequence, was subcloned into the plasmid vector pSP72 (Promega, Madison, Wis.) to generate the plasmid p343.7.16. A 7 kb BamHI/HindIII DNA fragment, comprising the germline human VH5-51 (DP-73) gene, together with approximately 5 kb of 5' flanking and 1 kb of 3' flanking genomic sequence, was cloned into the pBR322 based plasmid cloning vector pGP1f (Taylor et al. (1992) *Nucleic Acids Res.* 20: 6287-6295), to generate the plasmid p251f. A new cloning vector derived from pGP1f, pGP1k, was digested with EcoRV/BamHI, and ligated to a 10 kb EcoRV/BamHI DNA fragment, comprising the germline human VH3-23 (DP47) gene, together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251f. The resulting plasmid, pVx4, was digested with XhoI and ligated with the 8.5 kb XhoI/SalI insert of p343.7.16. A clone was obtained with the VH1-18 gene in the same orientation as the other two V genes. This clone, designated pVx6, was then digested with NotI for insert preparation.

The yeast artificial chromosome (YAC) yIgH24 was originally identified by PCR screening using VH3 and VH4 family specific primers and is mapped to the human chromosome 14 by VH content. It was established that yIgH24 contains VH segments including members of the VH families VH1, VH2, VH3, VH4, and VH5, and in particular at least VH1-24, VH1-45, VH1-46, VH2-26, VH3-30, V 3-30.5, VH3-30.3, VH3-33, VH3-43, VH3-48, VH3-49, VH3-53, VH4-28, VH4-30, VH4-30.4, VH4-30.3, VH4-31, VH4-34, 4-39, and VH5-51.

Purified inserts from pVX6 (26 kb), pHC2 (80 kb), and yIgH24 (~460 kb) were combined in a 1:1:1 molar ratio, and microinjected into the pronuclei of one-half day (C57BL/6J× DBA/2J) F2 embryos as described by Hogan et al. (B. Hogan et al., *Manipulating the Mouse Embryo, A Laboratory Manual*, 2$^{nd}$ edition, 1994, Cold Spring Harbor Laboratory Press, Plainview, N.Y.). A founder line of transgenic mice, comprising sequences from pVx6, HC2 and yIgH24, was established from mice that developed from the injected embryos. This line was designated (HCo17) 25950.

The (HCo17) 25950 line was then bred with mice comprising the CMD mutation (described in Example 1 of PCT Publication WO 01/09187), the JKD mutation (Chen et al. (1993) *EMBO J*. 12: 811-820), and the (KCo5)9272 transgene (Fishwild et al. (1996) *Nature Biotechnology* 14: 845-851). The resulting mice express human immunoglobulin heavy and kappa light chain transgenes in a background homozygous for disruption of the endogenous mouse heavy and kappa light chain loci.

SUMMARY OF SEQUENCE LISTING

| SEQ ID NO: | SEQUENCE |
|---|---|
| 1 | VH CDR1 a.a. 1D4 |
| 2 | VH CDR1 a.a. 1E1 |
| 3 | VH CDR1 a.a. 2G1 |
| 4 | VH CDR1 a.a. 3C4 |
| 5 | VH CDR1 a.a. 6A5 |
| 6 | VH CDR1 a.a. 6A8 |
| 7 | VH CDR1 a.a. 6B10 |
| 8 | VH CDR1 a.a. 7C10 |
| 9 | VH CDR1 a.a. 8F6 |
| 10 | VH CDR1 a.a. 10A12 |
| 11 | VH CDR1 a.a. 10A12S |
| 12 | VH CDR1 a.a. 13C4 |
| 13 | VH CDR2 a.a. 1D4 |
| 14 | VH CDR2 a.a. 1E1 |
| 15 | VH CDR2 a.a. 2G1 |
| 16 | VH CDR2 a.a. 3C4 |
| 17 | VH CDR2 a.a. 6A5 |
| 18 | VH CDR2 a.a. 6A8 |
| 19 | VH CDR2 a.a. 6B10 |
| 20 | VH CDR2 a.a. 7C10 |
| 21 | VH CDR2 a.a. 8F6 |
| 22 | VH CDR2 a.a. 10A12 |
| 23 | VH CDR2 a.a. 13C4 |
| 24 | VH CDR3 a.a. 1D4 |
| 25 | VH CDR3 a.a. 1E1 |
| 26 | VH CDR3 a.a. 2G1 |
| 27 | VH CDR3 a.a. 3C4 |
| 28 | VH CDR3 a.a. 6A5 |
| 29 | VH CDR3 a.a. 6A8 |
| 30 | VH CDR3 a.a. 6B10 |
| 31 | VH CDR3 a.a. 7C10 |
| 32 | VH CDR3 a.a. 8F6 |
| 33 | VH CDR3 a.a. 10A12 |
| 34 | VH CDR3 a.a. 13C4 |
| 35 | VH a.a. 1D4 |
| 36 | VH a.a. 1E1 |
| 37 | VH a.a. 2G1 |
| 38 | VH a.a. 3C4 |
| 39 | VH a.a. 6A5 |
| 40 | VH a.a. 6A8 |
| 41 | VH a.a. 6B10 |
| 42 | VH a.a. 7C10 |
| 43 | VH a.a. 8F6 |
| 44 | VH a.a. 10A12 |
| 45 | VH a.a. 10A12S |
| 46 | VH a.a. 13C4 |
| 47 | VH 3-33 germline a.a. |
| 48 | VH 3-30.3 germline a.a. |
| 49 | VH 5-51 germline a.a. |
| 50 | VH 4-61 germline a.a. |
| 51 | Vk CDR1 a.a. 1D4 |
| 52 | Vk CDR1 a.a. 1E1 |
| 53 | Vk CDR1 a.a. 2G1 |
| 54 | Vk CDR1 a.a. 3C4 |
| 55 | Vk CDR1 a.a. 6A5 |
| 56 | Vk CDR1 a.a. 6A8 |
| 57 | Vk CDR1 a.a. 6B10 |
| 58 | Vk CDR1 a.a. 7C10 |
| 59 | Vk CDR1 a.a. 8F6 |
| 60 | Vk CDR1 a.a. 10A12 |
| 61 | Vk CDR1 a.a. 13C4 |
| 62 | Vk CDR2 a.a. 1D4 |
| 63 | Vk CDR2 a.a. 1E1 |
| 64 | Vk CDR2 a.a. 2G1 |
| 65 | Vk CDR2 a.a. 3C4 |
| 66 | Vk CDR2 a.a. 6A5 |
| 67 | Vk CDR2 a.a. 6A8 |
| 68 | Vk CDR2 a.a. 6B10 |
| 69 | Vk CDR2 a.a. 7C10 |
| 70 | Vk CDR2 a.a. 8F6 |
| 71 | Vk CDR2 a.a. 10A12 |
| 72 | Vk CDR2 a.a. 13C4 |
| 73 | Vk CDR3 a.a. 1D4 |
| 74 | Vk CDR3 a.a. 1E1 |
| 75 | Vk CDR3 a.a. 2G1 |
| 76 | Vk CDR3 a.a. 3C4 |
| 77 | Vk CDR3 a.a. 6A5 |
| 78 | Vk CDR3 a.a. 6A8 |
| 79 | Vk CDR3 a.a. 6B10 |
| 80 | Vk CDR3 a.a. 7C10 |
| 81 | Vk CDR3 a.a. 8F6 |
| 82 | Vk CDR3 a.a. 10A12 |
| 83 | Vk CDR3 a.a. 13C4 |
| 84 | Vk a.a. 1D4 |
| 85 | Vk a.a. 1E1 |
| 86 | Vk a.a. 2G1 |
| 87 | Vk a.a. 3C4 |
| 88 | Vk a.a. 6A5 |
| 89 | Vk a.a. 6A8 |
| 90 | Vk a.a. 6B10 |
| 91 | Vk a.a. 7C10 |
| 92 | Vk a.a. 8F6 |
| 93 | Vk a.a. 10A12 |
| 94 | Vk a.a. 13C4 |
| 95 | Vk A27 germline a.a. |
| 96 | Vk L6 germline a.a. |
| 97 | Vk L18 germline a.a. |
| 98 | Vk L15 germline a.a. |
| 99 | VH n.t. 1D4 |
| 100 | VH n.t. 1E1 |
| 101 | VH n.t. 2G1 |
| 102 | VH n.t. 3C4 |
| 103 | VH n.t. 6A5 |
| 104 | VH n.t. 6A8 |
| 105 | VH n.t. 6B10 |
| 106 | VH n.t. 7C10 |
| 107 | VH n.t. 8F6 |
| 108 | VH n.t. 10A12 |
| 109 | VH n.t. 13C4 |
| 110 | Vk n.t 1D4 |
| 111 | Vk n.t. 1E1 |

-continued

SUMMARY OF SEQUENCE LISTING

| SEQ ID NO: | SEQUENCE |
|---|---|
| 112 | Vk n.t. 2G1 |
| 113 | Vk n.t. 3C4 |
| 114 | Vk n.t. 6A5 |
| 115 | Vk n.t. 6A8 |
| 116 | Vk n.t. 6B10 |
| 117 | Vk n.t. 7C10 |
| 118 | Vk n.t. 8F6 |
| 119 | Vk n.t. 10A12 |
| 120 | Vk n.t 13C4 |
| 121 | Human IP-10 a.a. |
| 122 | Human CXCR3 a.a. |
| 123 | Rhesus monkey IP-10 a.a. |
| 124 | Mouse IP-10 a.a. |

-continued

SUMMARY OF SEQUENCE LISTING

| SEQ ID NO: | SEQUENCE |
|---|---|
| 125 | Human Mig a.a. |
| 126 | Human ITAC a.a. |

EQUIVALENTS

Those skilled in the art will recognize or be able to ascertain, using no more than routine experimentation, many equivalents of the specific embodiments of the invention described herein. Such equivalents are intended to be encompassed by the following claims.

```

We claim:

1. An isolated monoclonal antibody, or antigen binding portion thereof, comprising:
   (a) a heavy chain variable region CDR1 comprising SEQ ID NO: 5;
   (b) a heavy chain variable region CDR2 comprising SEQ ID NO: 17;
   (c) a heavy chain variable region CDR3 comprising SEQ ID NO: 28;
   (d) a light chain variable region CDR1 comprising SEQ ID NO: 55;
   (e) a light chain variable region CDR2 comprising SEQ ID NO: 66; and
   (f) a light chain variable region CDR3 comprising SEQ ID NO: 77,
   wherein the antibody specifically binds IP-10 (SEQ ID NO: 121).

2. An isolated monoclonal antibody, or antigen binding portion thereof comprising:
   (a) a heavy chain variable region comprising SEQ ID NO: 39; and
   (b) a light chain variable region comprising SEQ ID NO: 88,
   wherein the antibody specifically binds IP-10 (SEQ ID NO: 121).

3. A composition comprising the antibody, or antigen-binding portion thereof, of claim 1, and a pharmaceutically acceptable carrier.

4. An immunoconjugate comprising the antibody, or antigen-binding portion thereof, of claim 1, linked to a therapeutic agent.

5. A composition comprising the immunoconjugate of claim 4 and a pharmaceutically acceptable carrier.

6. A bispecific molecule comprising the antibody, or antigen-binding portion thereof, of claim 1, linked to a second functional moiety having a different binding specificity than said antibody, or antigen binding portion thereof.

7. A composition comprising the bispecific molecule of claim 6, and a pharmaceutically acceptable carrier.

8. An isolated monoclonal antibody, or antigen binding portion thereof, comprising a heavy chain variable region and a light chain variable region, wherein the heavy chain variable region has the amino acid sequence set forth in SEQ ID NO: 39, wherein the antibody specifically binds IP-10 (SEQ ID NO: 121).

9. An isolated monoclonal antibody, or antigen binding portion thereof, comprising a heavy chain variable region and a light chain variable region, wherein the light chain variable region has the amino acid sequence set forth in SEQ ID NO: 88, wherein the antibody specifically binds IP-10 (SEQ ID NO: 121).

10. An isolated monoclonal antibody, or antigen binding portion thereof, which binds an epitope on human IP-10 (SEQ ID NO: 121) recognized by an antibody comprising a heavy chain variable region having the amino acid sequence set forth in SEQ ID NO: 39 and a light chain variable region having the amino acid sequence set forth in SEQ ID NO: 88.

11. The antibody, or antigen-binding portion thereof, of claim 8, 9, or 10, wherein the antibody exhibits at least one of the following functional properties:
   (i) the antibody cross-reacts with rhesus monkey IP-10 (SEQ ID NO: 123);
   (ii) the antibody does not cross-react with mouse IP-10 (SEQ ID NO: 124);
   (iii) the antibody does not cross-react with human MIG (SEQ ID NO: 125); or
   (iv) the antibody does not cross-react with human ITAC (SEQ ID NO: 126).

12. A composition comprising the antibody, or antigen-binding portion thereof, of claim 8, 9, or 10, and a pharmaceutically acceptable carrier.

13. An immunoconjugate comprising the antibody, or antigen-binding portion thereof, of claim 8, 9, or 10, linked to a therapeutic agent.

14. A composition comprising the immunoconjugate of claim 13 and a pharmaceutically acceptable carrier.

15. A bispecific molecule comprising the antibody, or antigen-binding portion thereof, of claim 8, 9, or 10, linked to a second functional moiety having a different binding specificity than said antibody, or antigen binding portion thereof.

16. A composition comprising the bispecific molecule of claim 15, and a pharmaceutically acceptable carrier.

17. A hybridoma prepared from transgenic mouse comprising human immunoglobulin heavy and light chain transgenes, wherein the mouse expresses the antibody of claim 8, 9, or 10.

* * * * *

                        SEQUENCE LISTING

<160> NUMBER OF SEQ ID NOS: 126

<210> SEQ ID NO 1
<211> LENGTH: 5
<212> TYPE: PRT
<213> ORGANISM: Homo sapiens

<400> SEQUENCE: 1

Ser Tyr Gly Met His
1               5

<210> SEQ ID NO 2
<211> LENGTH: 5
<212> TYPE: PRT
<213> ORGANISM: Homo sapiens

<400> SEQUENCE: 2

Thr Tyr Gly Met His
1               5

<210> SEQ ID NO 3
<211> LENGTH: 5
<212> TYPE: PRT
<213> ORGANISM: Homo sapiens

<400> SEQUENCE: 3

Asn Cys Gly Met His
1               5

<210> SEQ ID NO 4
<211> LENGTH: 5
<212> TYPE: PRT
<213> ORGANISM: Homo sapiens

<400> SEQUENCE: 4

Ser Tyr Trp Ile Gly
1               5

<210> SEQ ID NO 5
<211> LENGTH: 5
<212> TYPE: PRT
<213> ORGANISM: Homo sapiens

<400> SEQUENCE: 5

Asn Asn Gly Met His
1               5
```

```
<210> SEQ ID NO 6
<211> LENGTH: 5
<212> TYPE: PRT
<213> ORGANISM: Homo sapiens

<400> SEQUENCE: 6

Thr Tyr Gly Met His
1               5

<210> SEQ ID NO 7
<211> LENGTH: 5
<212> TYPE: PRT
<213> ORGANISM: Homo sapiens

<400> SEQUENCE: 7

Asn Ser Ala Met His
1               5

<210> SEQ ID NO 8
<211> LENGTH: 5
<212> TYPE: PRT
<213> ORGANISM: Homo sapiens

<400> SEQUENCE: 8

Asn Ser Gly Met His
1               5

<210> SEQ ID NO 9
<211> LENGTH: 5
<212> TYPE: PRT
<213> ORGANISM: Homo sapiens

<400> SEQUENCE: 9

Thr Tyr Gly Met His
1               5

<210> SEQ ID NO 10
<211> LENGTH: 5
<212> TYPE: PRT
<213> ORGANISM: Homo sapiens

<400> SEQUENCE: 10

Asn Cys Gly Met His
1               5

<210> SEQ ID NO 11
<211> LENGTH: 5
<212> TYPE: PRT
<213> ORGANISM: Homo sapiens

<400> SEQUENCE: 11

Asn Ser Gly Met His
1               5

<210> SEQ ID NO 12
<211> LENGTH: 7
<212> TYPE: PRT
<213> ORGANISM: Homo sapiens

<400> SEQUENCE: 12

Ser Gly Asp Tyr Tyr Trp Ser
1               5

<210> SEQ ID NO 13
```

<211> LENGTH: 17
<212> TYPE: PRT
<213> ORGANISM: Homo sapiens

<400> SEQUENCE: 13

Val Ile Trp Phe Glu Gly Ser Ile Lys Tyr Tyr Ala Asp Ser Val Lys
 1               5                  10                  15

Gly

<210> SEQ ID NO 14
<211> LENGTH: 17
<212> TYPE: PRT
<213> ORGANISM: Homo sapiens

<400> SEQUENCE: 14

Val Ile Trp Tyr Asp Gly Ser Asp Lys Tyr Tyr Ala Asp Ser Val Lys
 1               5                  10                  15

Asp

<210> SEQ ID NO 15
<211> LENGTH: 17
<212> TYPE: PRT
<213> ORGANISM: Homo sapiens

<400> SEQUENCE: 15

Leu Ile Gly Tyr Asp Gly Ile Asn Glu Tyr Tyr Ala Asp Ser Val Lys
 1               5                  10                  15

Gly

<210> SEQ ID NO 16
<211> LENGTH: 17
<212> TYPE: PRT
<213> ORGANISM: Homo sapiens

<400> SEQUENCE: 16

Val Ile Ser Pro Gly Asp Ser Asp Thr Arg Tyr Ser Pro Ser Phe Gln
 1               5                  10                  15

Gly

<210> SEQ ID NO 17
<211> LENGTH: 17
<212> TYPE: PRT
<213> ORGANISM: Homo sapiens

<400> SEQUENCE: 17

Val Ile Trp Phe Asp Gly Met Asn Lys Phe Tyr Val Asp Ser Val Lys
 1               5                  10                  15

Gly

<210> SEQ ID NO 18
<211> LENGTH: 17
<212> TYPE: PRT
<213> ORGANISM: Homo sapiens

<400> SEQUENCE: 18

Ile Ile Trp Phe Asp Gly Ser Asn Glu Asp Tyr Ala Ala Ser Val Lys
 1               5                  10                  15

Gly

<210> SEQ ID NO 19
<211> LENGTH: 17
<212> TYPE: PRT

<213> ORGANISM: Homo sapiens

<400> SEQUENCE: 19

Leu Ile Pro Phe Asp Gly Tyr Asn Lys Tyr Tyr Ala Asp Ser Val Lys
1               5                   10                  15

Gly

<210> SEQ ID NO 20
<211> LENGTH: 17
<212> TYPE: PRT
<213> ORGANISM: Homo sapiens

<400> SEQUENCE: 20

Val Ile Asp Tyr Asp Gly Ile Ile Gln Tyr Tyr Ala Asp Ser Val Lys
1               5                   10                  15

Gly

<210> SEQ ID NO 21
<211> LENGTH: 17
<212> TYPE: PRT
<213> ORGANISM: Homo sapiens

<400> SEQUENCE: 21

Val Ile Ser Tyr Asp Gly Ile Ile Lys His Tyr Ala Asp Ser Val Lys
1               5                   10                  15

Gly

<210> SEQ ID NO 22
<211> LENGTH: 17
<212> TYPE: PRT
<213> ORGANISM: Homo sapiens

<400> SEQUENCE: 22

Leu Ile Gly Phe Asp Gly Ile Asn Glu Tyr Tyr Ala Asp Ser Val Lys
1               5                   10                  15

Gly

<210> SEQ ID NO 23
<211> LENGTH: 16
<212> TYPE: PRT
<213> ORGANISM: Homo sapiens

<400> SEQUENCE: 23

Asn Ile Tyr Tyr Ser Gly Ser Thr Asn Tyr Asn Pro Ser Leu Lys Ser
1               5                   10                  15

<210> SEQ ID NO 24
<211> LENGTH: 15
<212> TYPE: PRT
<213> ORGANISM: Homo sapiens

<400> SEQUENCE: 24

Glu Gly Ala Gly Ser Ser Leu Tyr Tyr Tyr Gly Met Asp Val
1               5                   10                  15

<210> SEQ ID NO 25
<211> LENGTH: 11
<212> TYPE: PRT
<213> ORGANISM: Homo sapiens

<400> SEQUENCE: 25

Asn Ile Ala Val Ala Asp Val Ala Phe Asp Leu
1               5                   10

<210> SEQ ID NO 26
<211> LENGTH: 12
<212> TYPE: PRT
<213> ORGANISM: Homo sapiens

<400> SEQUENCE: 26

Asp Trp Pro Glu Gly Tyr Tyr Asn Gly Met Asp Val
1               5                   10

<210> SEQ ID NO 27
<211> LENGTH: 14
<212> TYPE: PRT
<213> ORGANISM: Homo sapiens

<400> SEQUENCE: 27

Gly Tyr Cys Ser Gly Gly Ser Cys Tyr Pro Phe Phe Gln Tyr
1               5                   10

<210> SEQ ID NO 28
<211> LENGTH: 15
<212> TYPE: PRT
<213> ORGANISM: Homo sapiens

<400> SEQUENCE: 28

Glu Gly Asp Gly Ser Gly Ile Tyr Tyr Tyr Gly Met Asp Val
1               5                   10                  15

<210> SEQ ID NO 29
<211> LENGTH: 15
<212> TYPE: PRT
<213> ORGANISM: Homo sapiens

<400> SEQUENCE: 29

Glu Gly Asp Gly Ser Ser Leu Tyr Tyr Tyr Gly Met Asp Val
1               5                   10                  15

<210> SEQ ID NO 30
<211> LENGTH: 13
<212> TYPE: PRT
<213> ORGANISM: Homo sapiens

<400> SEQUENCE: 30

Glu Gly Gly Tyr Thr Gly Tyr Asp Gly Gly Phe Asp Tyr
1               5                   10

<210> SEQ ID NO 31
<211> LENGTH: 14
<212> TYPE: PRT
<213> ORGANISM: Homo sapiens

<400> SEQUENCE: 31

Glu Arg Gly Thr His Tyr Tyr Gly Ser Gly Ser Phe Asp Tyr
1               5                   10

<210> SEQ ID NO 32
<211> LENGTH: 11
<212> TYPE: PRT
<213> ORGANISM: Homo sapiens

<400> SEQUENCE: 32

Asp Ser Ser Ser Trp Tyr Val Tyr Phe Asp Tyr
1               5                   10

<210> SEQ ID NO 33

```
<211> LENGTH: 12
<212> TYPE: PRT
<213> ORGANISM: Homo sapiens

<400> SEQUENCE: 33

Asp Trp Pro Glu Gly Tyr Tyr Asn Gly Met Asp Val
1               5                   10

<210> SEQ ID NO 34
<211> LENGTH: 20
<212> TYPE: PRT
<213> ORGANISM: Homo sapiens

<400> SEQUENCE: 34

Gly Gly Gly Thr Val Val Arg Gly Ile Ile His Tyr Tyr Tyr Tyr Tyr
1               5                   10                  15

Gly Met Asp Val
            20

<210> SEQ ID NO 35
<211> LENGTH: 121
<212> TYPE: PRT
<213> ORGANISM: Homo sapiens

<400> SEQUENCE: 35

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Phe Glu Gly Ser Ile Lys Tyr Tyr Ala Asp Ser Val
        50                  55                  60

Lys Gly Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Arg Glu
                85                  90                  95

Gly Ala Gly Ser Ser Leu Tyr Tyr Tyr Tyr Gly Met Asp Val Trp Gly
            100                 105                 110

Gln Gly Thr Thr Val Thr Val Ser Ser
        115                 120

<210> SEQ ID NO 36
<211> LENGTH: 120
<212> TYPE: PRT
<213> ORGANISM: Homo sapiens

<400> SEQUENCE: 36

Gln Glu Gln Leu Val Glu Ser Gly Gly Asn Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asp Lys Tyr Tyr Ala Asp Ser Val
        50                  55                  60

Lys Asp Arg Phe Thr Val Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Asn Ile Ala Val Ala Asp Val Ala Phe Asp Leu Trp Gly Gln
            100                 105                 110

Gly Thr Met Val Thr Val Ser Ser
        115                 120

<210> SEQ ID NO 37
<211> LENGTH: 121
<212> TYPE: PRT
<213> ORGANISM: Homo sapiens

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Cys
            20                  25                  30

Gly Met His Trp Val Arg Gln Ala Pro Gly Lys Gly Leu Glu Trp Val
        35                  40                  45

Ala Leu Ile Gly Tyr Asp Gly Ile Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Phe Tyr Cys
                85                  90                  95

Ala Arg Asp Trp Pro Glu Gly Tyr Tyr Asn Gly Met Asp Val Trp Gly
            100                 105                 110

Gln Gly Thr Thr Val Thr Val Ser Ser
        115                 120

<210> SEQ ID NO 38
<211> LENGTH: 123
<212> TYPE: PRT
<213> ORGANISM: Homo sapiens

<400> SEQUENCE: 38

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Pro Ser Tyr
            20                  25                  30

Trp Ile Gly Trp Val Arg Gln Met Pro Gly Lys Gly Leu Glu Trp Met
        35                  40                  45

Gly Val Ile Ser Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Cys Ser Gly Gly Ser Cys Tyr Pro Phe Phe Gln Tyr
            100                 105                 110

Trp Gly Gln Gly Thr Leu Val Thr Val Ser Ser
        115                 120

<210> SEQ ID NO 39
<211> LENGTH: 124
<212> TYPE: PRT
<213> ORGANISM: Homo sapiens

<400> SEQUENCE: 39

Gln Met Gln Leu Val Glu Ser Gly Gly Gly Val Val Gln Pro Gly Arg

-continued

```
                1               5                  10                 15
        Ser Leu Arg Leu Ser Cys Thr Ala Ser Gly Phe Thr Phe Ser Asn Asn
                        20                  25                  30

Gly Met His Trp Val Arg Gln Ala Pro Gly Lys Gly Leu Glu Trp Val
                        35                  40                  45

Ala Val Ile Trp Phe Asp Gly Met Asn Lys Phe Tyr Val Asp Ser Val
                        50                  55                  60

Lys Gly Arg Phe Thr Ile Ser Arg Asp Asn Ser Lys Asn Thr Leu Tyr
         65                  70                  75                  80

Leu Glu Met Asn Ser Leu Arg Ala Glu Asp Thr Ala Ile Tyr Tyr Cys
                        85                  90                  95

Ala Arg Glu Gly Asp Gly Ser Gly Ile Tyr Tyr Tyr Gly Met Asp
                        100                 105                 110

Val Trp Gly Gln Gly Thr Thr Val Thr Val Ser Ser
                        115                 120
```

<210> SEQ ID NO 40
<211> LENGTH: 124
<212> TYPE: PRT
<213> ORGANISM: Homo sapiens

<400> SEQUENCE: 40

```
        Gln Val Gln Leu Val Glu Ser Gly Gly Gly Val Val Gln Pro Gly Arg
         1               5                  10                 15

Ser Leu Arg Leu Ser Cys Thr Ala Ser Gly Phe Thr Phe Ser Thr Tyr
                        20                  25                  30

Gly Met His Trp Val Arg Gln Ala Pro Gly Lys Gly Leu Glu Trp Val
                        35                  40                  45

Ala Ile Ile Trp Phe Asp Gly Ser Asn Glu Asp Tyr Ala Ala Ser Val
                        50                  55                  60

Lys Gly Arg Phe Thr Ile Ser Arg Asp Asn Ser Lys Asn Thr Leu Tyr
         65                  70                  75                  80

Leu Gln Met Asn Ser Leu Arg Ala Glu Asp Thr Ala Val Tyr Tyr Cys
                        85                  90                  95

Ala Arg Glu Gly Asp Gly Ser Ser Leu Tyr Tyr Tyr Gly Met Asp
                        100                 105                 110

Val Trp Gly Gln Gly Thr Thr Val Thr Val Ser Ser
                        115                 120
```

<210> SEQ ID NO 41
<211> LENGTH: 246
<212> TYPE: PRT
<213> ORGANISM: Homo sapiens

<400> SEQUENCE: 41

```
        Gln Val Gln Leu Val Glu Ser Gly Gly Gly Val Val Gln Pro Gly Arg
         1               5                  10                 15

Ser Leu Arg Leu Ser Cys Thr Ala Ser Gly Phe Thr Phe Ser Thr Tyr
                        20                  25                  30

Gly Met His Trp Val Arg Gln Ala Pro Gly Lys Gly Leu Glu Trp Val
                        35                  40                  45

Ala Ile Ile Trp Phe Asp Gly Ser Asn Glu Asp Tyr Ala Ala Ser Val
                        50                  55                  60

Lys Gly Arg Phe Thr Ile Ser Arg Asp Asn Ser Lys Asn Thr Leu Tyr
         65                  70                  75                  80

Leu Gln Met Asn Ser Leu Arg Ala Glu Asp Thr Ala Val Tyr Tyr Cys
                        85                  90                  95
```

Ala Arg Glu Gly Asp Gly Ser Ser Leu Tyr Tyr Tyr Gly Met Asp
            100                 105                 110

Val Trp Gly Gln Gly Thr Thr Val Thr Val Ser Ser Gln Val Gln Leu
    115                 120                 125

Val Glu Ser Gly Gly Gly Val Val Gln Pro Gly Arg Ser Leu Arg Leu
130                 135                 140

Ser Cys Ala Ala Ser Gly Phe Thr Phe Ser Asn Ser Ala Met His Trp
145                 150                 155                 160

Val Arg Gln Ala Pro Gly Lys Gly Leu Glu Trp Val Ala Leu Ile Pro
            165                 170                 175

Phe Asp Gly Tyr Asn Lys Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
            195                 200                 205

Ser Leu Arg Ala Glu Asp Thr Ala Val Tyr Tyr Cys Ala Arg Glu Gly
            210                 215                 220

Gly Tyr Thr Gly Tyr Asp Gly Gly Phe Asp Tyr Trp Gly Gln Gly Ile
225                 230                 235                 240

Leu Val Thr Val Ser Ser
            245

<210> SEQ ID NO 42
<211> LENGTH: 123
<212> TYPE: PRT
<213> ORGANISM: Homo sapiens

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ser
            20                  25                  30

Gly Met His Trp Val Arg Gln Ala Pro Gly Lys Gly Leu Glu Trp Val
        35                  40                  45

Ala Val Ile Asp Tyr Asp Gly Ile Ile Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Thr Glu Arg Gly Thr His Tyr Tyr Gly Ser Gly Ser Phe Asp Tyr
            100                 105                 110

Trp Gly Gln Gly Thr Leu Val Thr Val Ser Ser
        115                 120

<210> SEQ ID NO 43
<211> LENGTH: 120
<212> TYPE: PRT
<213> ORGANISM: Homo sapiens

<400> SEQUENCE: 43

Gln Val Gln Leu Val Asp Ser Gly Gly Gly Val Val Gln Pro Gly Arg
1               5                   10                  15

Ser Leu Arg Leu Ser Cys Ala Ala Ser Gly Phe Thr Phe Asn Thr Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ile Lys His Tyr Ala Asp Ser Val
         50                  55                  60

Lys Gly Arg Phe Thr Ile Thr Arg Asp Asn Ser Lys Asn Met Val His
 65                  70                  75                  80

Leu Gln Met Asn Ser Leu Arg Ala Glu Asp Thr Ala Val Tyr Tyr Cys
                 85                  90                  95

Ala Arg Asp Ser Ser Ser Trp Tyr Val Tyr Phe Asp Tyr Trp Gly Gln
                100                 105                 110

Gly Thr Leu Val Thr Val Ser Ser
            115                 120

<210> SEQ ID NO 44
<211> LENGTH: 121
<212> TYPE: PRT
<213> ORGANISM: Homo sapiens

<400> SEQUENCE: 44

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Asn Cys
                 20                  25                  30

Gly Met His Trp Val Arg Gln Ala Pro Gly Lys Gly Leu Glu Trp Val
                 35                  40                  45

Ala Leu Ile Gly Phe Asp Gly Ile Asn Glu Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Pro Glu Gly Tyr Tyr Asn Gly Met Asp Val Trp Gly
                100                 105                 110

Gln Gly Thr Thr Val Thr Val Ser Ser
            115                 120

<210> SEQ ID NO 45
<211> LENGTH: 121
<212> TYPE: PRT
<213> ORGANISM: Homo sapiens

<400> SEQUENCE: 45

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Asn Ser
                 20                  25                  30

Gly Met His Trp Val Arg Gln Ala Pro Gly Lys Gly Leu Glu Trp Val
                 35                  40                  45

Ala Leu Ile Gly Phe Asp Gly Ile Asn Glu Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Pro Glu Gly Tyr Tyr Asn Gly Met Asp Val Trp Gly
                100                 105                 110

Gln Gly Thr Thr Val Thr Val Ser Ser
            115                 120
```

<210> SEQ ID NO 46
<211> LENGTH: 130
<212> TYPE: PRT
<213> ORGANISM: Homo sapiens

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Ile Ser Gly Gly Ser Val Ser Ser Gly
            20                  25                  30

Asp Tyr Tyr Trp Ser Trp Ile Arg Gln Pro Pro Gly Lys Gly Leu Glu
        35                  40                  45

Trp Ile Gly Asn Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Gly Thr Val Arg Gly Ile Ile His Tyr Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 47
<211> LENGTH: 117
<212> TYPE: PRT
<213> ORGANISM: Homo sapiens

<400> SEQUENCE: 47

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Tyr Tyr Gly Met Asp Val Trp Gly Gln Gly Thr Thr
            100                 105                 110

Val Thr Val Ser Ser
        115

<210> SEQ ID NO 48
<211> LENGTH: 103
<212> TYPE: PRT
<213> ORGANISM: Homo sapiens

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Thr Val Ser Ser
            100
```

<210> SEQ ID NO 49
<211> LENGTH: 98
<212> TYPE: PRT
<213> ORGANISM: Homo sapiens

<400> SEQUENCE: 49

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg
```

<210> SEQ ID NO 50
<211> LENGTH: 99
<212> TYPE: PRT
<213> ORGANISM: Homo sapiens

<400> SEQUENCE: 50

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg
```

<210> SEQ ID NO 51
<211> LENGTH: 12
<212> TYPE: PRT
<213> ORGANISM: Homo sapiens

<400> SEQUENCE: 51

Arg Ala Ser Gln Ser Val Ser Ser Gly His Leu Ala

```
<210> SEQ ID NO 52
<211> LENGTH: 11
<212> TYPE: PRT
<213> ORGANISM: Homo sapiens

<400> SEQUENCE: 52

Arg Ala Ser Gln Ser Val Ser Ser Tyr Leu Ala
 1               5                  10

<210> SEQ ID NO 53
<211> LENGTH: 12
<212> TYPE: PRT
<213> ORGANISM: Homo sapiens

<400> SEQUENCE: 53

Arg Ala Ser Gln Ser Val Ser Ser Ser Tyr Leu Ala
 1               5                  10

<210> SEQ ID NO 54
<211> LENGTH: 11
<212> TYPE: PRT
<213> ORGANISM: Homo sapiens

<400> SEQUENCE: 54

Arg Ala Ser Gln Gly Ile Ser Ser Ala Leu Ala
 1               5                  10

<210> SEQ ID NO 55
<211> LENGTH: 12
<212> TYPE: PRT
<213> ORGANISM: Homo sapiens

<400> SEQUENCE: 55

Arg Ala Ser Gln Ser Val Ser Ser Ser Tyr Leu Ala
 1               5                  10

<210> SEQ ID NO 56
<211> LENGTH: 12
<212> TYPE: PRT
<213> ORGANISM: Homo sapiens

<400> SEQUENCE: 56

Arg Ala Ser Gln Ser Ile Ser Ser Gly Tyr Leu Ala
 1               5                  10

<210> SEQ ID NO 57
<211> LENGTH: 11
<212> TYPE: PRT
<213> ORGANISM: Homo sapiens

<400> SEQUENCE: 57

Arg Ala Ser Gln Ser Val Ser Ser Tyr Leu Ala
 1               5                  10

<210> SEQ ID NO 58
<211> LENGTH: 11
<212> TYPE: PRT
<213> ORGANISM: Homo sapiens

<400> SEQUENCE: 58

Arg Ala Ser Gln Gly Ile Ser Ser Trp Leu Ala
 1               5                  10
```

```
<210> SEQ ID NO 59
<211> LENGTH: 11
<212> TYPE: PRT
<213> ORGANISM: Homo sapiens

<400> SEQUENCE: 59

Arg Ala Ser Gln Ser Val Ser Ser Tyr Val Ala
 1               5                  10

<210> SEQ ID NO 60
<211> LENGTH: 12
<212> TYPE: PRT
<213> ORGANISM: Homo sapiens

<400> SEQUENCE: 60

Arg Ala Ser Gln Ser Val Ser Ser Ser Tyr Leu Ala
 1               5                  10

<210> SEQ ID NO 61
<211> LENGTH: 12
<212> TYPE: PRT
<213> ORGANISM: Homo sapiens

<400> SEQUENCE: 61

Arg Ala Ser Gln Ser Val Ser Ser Ser Tyr Leu Ala
 1               5                  10

<210> SEQ ID NO 62
<211> LENGTH: 7
<212> TYPE: PRT
<213> ORGANISM: Homo sapiens

<400> SEQUENCE: 62

Gly Ala Ser Ser Arg Ala Thr
 1               5

<210> SEQ ID NO 63
<211> LENGTH: 7
<212> TYPE: PRT
<213> ORGANISM: Homo sapiens

<400> SEQUENCE: 63

Asp Ala Ser Asn Arg Ala Thr
 1               5

<210> SEQ ID NO 64
<211> LENGTH: 7
<212> TYPE: PRT
<213> ORGANISM: Homo sapiens

<400> SEQUENCE: 64

Gly Ala Ser Ser Arg Ala Thr
 1               5

<210> SEQ ID NO 65
<211> LENGTH: 7
<212> TYPE: PRT
<213> ORGANISM: Homo sapiens

<400> SEQUENCE: 65

Asp Ala Ser Ser Leu Glu Ser
 1               5

<210> SEQ ID NO 66
<211> LENGTH: 7
<212> TYPE: PRT
```

```
<213> ORGANISM: Homo sapiens

<400> SEQUENCE: 66

Gly Ala Ser Ser Arg Ala Thr
 1               5

<210> SEQ ID NO 67
<211> LENGTH: 7
<212> TYPE: PRT
<213> ORGANISM: Homo sapiens

<400> SEQUENCE: 67

Gly Ala Ser Ser Arg Ala Thr
 1               5

<210> SEQ ID NO 68
<211> LENGTH: 7
<212> TYPE: PRT
<213> ORGANISM: Homo sapiens

<400> SEQUENCE: 68

Asp Ala Ser Asn Arg Ala Thr
 1               5

<210> SEQ ID NO 69
<211> LENGTH: 7
<212> TYPE: PRT
<213> ORGANISM: Homo sapiens

<400> SEQUENCE: 69

Ala Ala Ser Ser Leu Gln Ser
 1               5

<210> SEQ ID NO 70
<211> LENGTH: 7
<212> TYPE: PRT
<213> ORGANISM: Homo sapiens

<400> SEQUENCE: 70

Asp Ala Ser Asn Arg Ala Thr
 1               5

<210> SEQ ID NO 71
<211> LENGTH: 7
<212> TYPE: PRT
<213> ORGANISM: Homo sapiens

<400> SEQUENCE: 71

Gly Ala Ser Ser Arg Ala Thr
 1               5

<210> SEQ ID NO 72
<211> LENGTH: 7
<212> TYPE: PRT
<213> ORGANISM: Homo sapiens

<400> SEQUENCE: 72

Gly Ala Ser Ser Arg Ala Thr
 1               5

<210> SEQ ID NO 73
<211> LENGTH: 9
<212> TYPE: PRT
<213> ORGANISM: Homo sapiens

<400> SEQUENCE: 73
```

```
Gln Gln Tyr Gly Ser Ser Pro Tyr Thr
1               5

<210> SEQ ID NO 74
<211> LENGTH: 10
<212> TYPE: PRT
<213> ORGANISM: Homo sapiens

<400> SEQUENCE: 74

Gln Gln Arg Ser Asn Trp Pro Pro Leu Thr
1               5                   10

<210> SEQ ID NO 75
<211> LENGTH: 10
<212> TYPE: PRT
<213> ORGANISM: Homo sapiens

<400> SEQUENCE: 75

Gln Gln Tyr Gly Ser Ser Pro Pro Phe Thr
1               5                   10

<210> SEQ ID NO 76
<211> LENGTH: 9
<212> TYPE: PRT
<213> ORGANISM: Homo sapiens

<400> SEQUENCE: 76

Gln Gln Phe Asp Ser Phe Pro His Thr
1               5

<210> SEQ ID NO 77
<211> LENGTH: 10
<212> TYPE: PRT
<213> ORGANISM: Homo sapiens

<400> SEQUENCE: 77

Gln Gln Tyr Gly Ser Ser Pro Ile Phe Thr
1               5                   10

<210> SEQ ID NO 78
<211> LENGTH: 8
<212> TYPE: PRT
<213> ORGANISM: Homo sapiens

<400> SEQUENCE: 78

Gln Gln Tyr Gly Ser Ser Pro Thr
1               5

<210> SEQ ID NO 79
<211> LENGTH: 10
<212> TYPE: PRT
<213> ORGANISM: Homo sapiens

<400> SEQUENCE: 79

Gln Gln Arg Ser Asn Trp Pro Pro Tyr Thr
1               5                   10

<210> SEQ ID NO 80
<211> LENGTH: 9
<212> TYPE: PRT
<213> ORGANISM: Homo sapiens

<400> SEQUENCE: 80

Gln Gln Tyr Asn Ser Tyr Pro Pro Thr
1               5
```

<210> SEQ ID NO 81
<211> LENGTH: 10
<212> TYPE: PRT
<213> ORGANISM: Homo sapiens

<400> SEQUENCE: 81

Gln Gln Arg Ser Asn Ser Pro Pro Trp Thr
1               5                   10

<210> SEQ ID NO 82
<211> LENGTH: 10
<212> TYPE: PRT
<213> ORGANISM: Homo sapiens

<400> SEQUENCE: 82

Gln Gln Tyr Gly Ser Ser Pro Pro Phe Thr
1               5                   10

<210> SEQ ID NO 83
<211> LENGTH: 10
<212> TYPE: PRT
<213> ORGANISM: Homo sapiens

<400> SEQUENCE: 83

Gln Gln Tyr Gly Ser Ser Pro Glu Tyr Thr
1               5                   10

<210> SEQ ID NO 84
<211> LENGTH: 108
<212> TYPE: PRT
<213> ORGANISM: Homo sapiens

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
                20                  25                  30

His Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Gly Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
                100                 105

<210> SEQ ID NO 85
<211> LENGTH: 108
<212> TYPE: PRT
<213> ORGANISM: Homo sapiens

<400> SEQUENCE: 85

Glu Ile Val Leu Thr Gln Ser Pro Ala Ile Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

-continued

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105

<210> SEQ ID NO 86
<211> LENGTH: 109
<212> TYPE: PRT
<213> ORGANISM: Homo sapiens

<400> SEQUENCE: 86

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                85                  90                  95

Pro Phe Thr Phe Gly Pro Gly Thr Lys Val Asp Ile Lys
            100                 105

<210> SEQ ID NO 87
<211> LENGTH: 107
<212> TYPE: PRT
<213> ORGANISM: Homo sapiens

<400> SEQUENCE: 87

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asp Ser Phe Pro His
                85                  90                  95

Thr Phe Gly Gly Gly Thr Lys Val Glu Ile Lys
            100                 105

<210> SEQ ID NO 88
<211> LENGTH: 109
<212> TYPE: PRT
<213> ORGANISM: Homo sapiens

<400> SEQUENCE: 88

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Phe Thr Phe Gly Pro Gly Thr Lys Val Asp Ile Lys
                100                 105

<210> SEQ ID NO 89
<211> LENGTH: 107
<212> TYPE: PRT
<213> ORGANISM: Homo sapiens

<400> SEQUENCE: 89

Glu Val Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Gly
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gly Gly Thr Lys Val Glu Ile Lys
                100                 105

<210> SEQ ID NO 90
<211> LENGTH: 108
<212> TYPE: PRT
<213> ORGANISM: Homo sapiens

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys
                100                 105

<210> SEQ ID NO 91
<211> LENGTH: 107

```
<212> TYPE: PRT
<213> ORGANISM: Homo sapiens

<400> SEQUENCE: 91

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 92
<211> LENGTH: 108
<212> TYPE: PRT
<213> ORGANISM: Homo sapiens

<400> SEQUENCE: 92

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Val Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln Arg Ser Asn Ser Pro Pro
                85                  90                  95

Trp Thr Phe Gly Gln Gly Thr Lys Val Glu Ile Lys
            100                 105

<210> SEQ ID NO 93
<211> LENGTH: 109
<212> TYPE: PRT
<213> ORGANISM: Homo sapiens

<400> SEQUENCE: 93

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

```
Pro Phe Thr Phe Gly Pro Gly Thr Lys Val Asp Ile Lys
            100                 105
```

<210> SEQ ID NO 94
<211> LENGTH: 109
<212> TYPE: PRT
<213> ORGANISM: Homo sapiens

<400> SEQUENCE: 94

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Glu Tyr Thr Phe Gly Gln Gly Thr Lys Leu Glu Ile Lys
            100                 105
```

<210> SEQ ID NO 95
<211> LENGTH: 96
<212> TYPE: PRT
<213> ORGANISM: Homo sapiens

<400> SEQUENCE: 95

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95
```

<210> SEQ ID NO 96
<211> LENGTH: 95
<212> TYPE: PRT
<213> ORGANISM: Homo sapiens

<400> SEQUENCE: 96

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro
                    85                  90                  95

<210> SEQ ID NO 97
<211> LENGTH: 95
<212> TYPE: PRT
<213> ORGANISM: Homo sapiens

<400> SEQUENCE: 97

Ala Ile Gln Leu Thr Gln Ser Pro Ser Leu Ser Ala Ser Val Gly
 1               5                  10                  15

Asp Arg Val Thr Ile Thr Cys Arg Ala Ser Gln Gly Ile Ser Ala
                20                  25                  30

Leu Ala Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                    85                  90                  95

<210> SEQ ID NO 98
<211> LENGTH: 95
<212> TYPE: PRT
<213> ORGANISM: Homo sapiens

<400> SEQUENCE: 98

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                    85                  90                  95

<210> SEQ ID NO 99
<211> LENGTH: 372
<212> TYPE: DNA
<213> ORGANISM: Homo sapiens

<400> SEQUENCE: 99
caggtgcagt tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagtt atatggtttg aaggaagtat taaatactat     180
gcagactccg tgaagggccg attcaccatc tccagagaca attccaagaa tacgctgtat     240
ctgcaaatga acagcctgag agccgaggac acggctgtgt attattgtgc gagagagggt     300
gcggggagtt ctctctacta ctactacggt atggacgtct ggggccaagg gaccacggtc     360
accgtctcct ca                                                         372
```

```
<210> SEQ ID NO 100
<211> LENGTH: 360
<212> TYPE: DNA
<213> ORGANISM: Homo sapiens

<400> SEQUENCE: 100
caggagcagc tggtggagtc tgggggaaac gtggtccagc ctggaggtc cctgagactc      60 tcctgtgcag cgtctggatt cacctttagt acttatggca tgcactgggt ccgccaggct    120
ccaggcaagg ggctggagtg ggtggcagtt atatggtatg atggaagtga taaatactat    180
gcagactccg tgaaggaccg attcacggtc tccaaagaca attccaagaa cacgctgtat    240
ctgcaaatga acagcctgag agccgaggac acggctgtgt attactgtgc gagaaatata    300
gcagtggctg acgttgcttt tgatctctgg ggccagggga caatggtcac cgtctcttca    360

<210> SEQ ID NO 101
<211> LENGTH: 363
<212> TYPE: DNA
<213> ORGANISM: Homo sapiens

<400> SEQUENCE: 101
caggtgcagc tggtggagtc tgggggaggc gtggtccagc ctggaggtc cctgagactc      60 tcctgtgcag cgtctggatt cacccttcagt aactgtggca tgcactgggt ccgccaggct   120
ccaggcaagg ggctggagtg ggtggcactt ataggggtatg atggaattaa tgaatactat    180
gcagactccg tgaagggccg attcaccatc tccagagaca attccaagaa cacgctgtat    240
ctgcaaatga acagcctgag agccgaggac acggctgtgt tttactgtgc gagagactgg    300
cctgagggct actacaacgg catggacgtc tggggccaag gaccacggt caccgtctcc    360 tca                                                                  363

<210> SEQ ID NO 102
<211> LENGTH: 369
<212> TYPE: DNA
<213> ORGANISM: Homo sapiens

<400> SEQUENCE: 102
gaggtgcagc tggtgcagtc tggagcagag gtgaaaaagc ccggggagtc tctgaagatc     60
tcctgtaagg gttctggata caactttccc agctactgga tcggctgggt gcgccagatg    120
cccgggaaag gcctggagtg gatggggtc atctctcctg gtgactctga taccagatac     180
agcccgtcct tccaaggcca agtcaccatc tcagccgaca gtccatcag caccgcctac    240 ctgcagtgga gcagcctgaa ggcctcggac accgccatgt attactgtgc gagaggatat    300
tgtagtggtg gtagctgcta cccattcttc cagtactggg gccagggcac cctggtcacc   360
gtctcctcc                                                            369

<210> SEQ ID NO 103
<211> LENGTH: 372
<212> TYPE: DNA
<213> ORGANISM: Homo sapiens

<400> SEQUENCE: 103
caaatgcagc tggtggagtc tgggggaggc gtggtccagc ctggaggtc cctgagactc      60 tcctgtacag cgtctggatt cacccttcagt aacaatggca tgcactgggt ccgccaggct   120
ccaggcaagg ggctggagtg ggtggcagtt atatggtttg atggaatgaa taaattctat    180
gtagactccg tgaagggccg attcaccatc tccagagaca attccaagaa cacgctgtat    240
ctggaaatga acagcctgag agccgaggac acggctatat attactgtgc gagagaaggg    300
```

```
gatggttcgg ggatttatta ctactacggt atggacgtct ggggccaagg gaccacggtc      360
accgtctcct ca                                                          372

<210> SEQ ID NO 104
<211> LENGTH: 372
<212> TYPE: DNA
<213> ORGANISM: Homo sapiens

<400> SEQUENCE: 104
caggtgcagc tggtggagtc tgggggaggc gtggtccagc ctgggaggtc cctgagactc       60
tcctgtacag cgtctggatt caccttcagt acctatggca tgcactgggt ccgccaggct      120
ccaggcaagg ggctggagtg ggtggcaatt atatggttcg atggaagtaa tgaagattat      180
gcagcctccg tgaagggccg attcaccatc tccagagaca attccaagaa cacgctgtat      240
ctgcaaatga acagcctgag agccgaggac acggctgtgt attactgtgc gagagagggg      300
gatgggagct ccttatacta ctactacggt atggacgtct ggggccaagg gaccacggtc      360
accgtctcct ca                                                          372

<210> SEQ ID NO 105
<211> LENGTH: 366
<212> TYPE: DNA
<213> ORGANISM: Homo sapiens

<400> SEQUENCE: 105
caggtgcagc tggtggagtc tgggggaggc gtggtccagc ctgggaggtc cctgagactc       60
tcctgtgcag cctctggatt caccttcagt aactctgcta tgcactgggt ccgccaggct      120
ccaggcaagg ggctggagtg ggtggcactt ataccatttg atggatacaa taaatactac      180
gcagactccg tgaagggccg attcaccatc tccagagaca attccaagaa cacgctgtat      240
ctgcaaatga acagcctgag agctgaggac acggctgtgt attactgcgc gagagaaggt      300
ggatatactg gctacgatgg gggatttgac tattggggcc agggaatcct ggtcaccgtc      360
tcctca                                                                 366

<210> SEQ ID NO 106
<211> LENGTH: 369
<212> TYPE: DNA
<213> ORGANISM: Homo sapiens

<400> SEQUENCE: 106
caggtgcaac tggtggagtc tgggggaggc gtggtccagc ctgggaggtc cctgagactc       60
tcctgtgcag cgtctggatt caccttcagt aactctggca tgcactgggt ccgccaggct      120
ccaggcaagg ggctggagtg ggtggcagtt atagactatg atggaattat tcaatactat      180
gccgactccg tgaagggccg attcaccatc tccagagaca attccaagaa cacgctgtat      240
ctgcaaataa acagcctgag agccgaggac acggctgtgt attactgtgc gacagagagg      300
ggcacgcatt actatggttc ggggagtttt gactactggg gccagggaac cctggtcacc      360
gtctcctca                                                              369

<210> SEQ ID NO 107
<211> LENGTH: 360
<212> TYPE: DNA
<213> ORGANISM: Homo sapiens

<400> SEQUENCE: 107
caggtgcaac tggtggactc tgggggaggc gtggtccagc ctgggaggtc cctgagactc       60
```

```
tcctgtgcag cctctggatt caccttcaat acctatggca tgcactgggt ccgccaggct      120
ccaggcaagg ggctggagtg ggtggcagtt atatcatatg atggaatcat taaacactac      180
gccgactccg tgaagggccg attcaccata accagagaca attccaagaa catggtgcat      240
ctgcaaatga acagcctgag agctgaggac acggctgtgt attactgtgc gagagatagc      300
agcagctggt acgtctactt tgactactgg ggccagggaa ccctggtcac cgtctcctca      360
```

<210> SEQ ID NO 108
<211> LENGTH: 363
<212> TYPE: DNA
<213> ORGANISM: Homo sapiens

<400> SEQUENCE: 108

```
caggtgcagc tggtggagtc tgggggaggc gtggtccagc ctgggaggtc cctgagactc      60
tcctgtgcag cgtctggatt caccttcagt aactgtggca tgcactgggt ccgccaggct     120
ccaggcaagg ggctggagtg ggtggcactt atagggtttg atggaattaa tgaatactat     180
gcagactccg tgaagggccg attcaccatc tccagagaca attccaagaa cacgctgtat     240
ctgcaaatga acagcctgag agccgaggac acggctgtgt attattgtgc gagagactgg     300
cctgagggct actacaacgg catggacgtc tggggccaag gaccacggt caccgtctcc      360 tca                                                                  363
```

<210> SEQ ID NO 109
<211> LENGTH: 390
<212> TYPE: DNA
<213> ORGANISM: Homo sapiens

<400> SEQUENCE: 109

```
caggtgcagc tgcaggagtc gggcccagga ctggtgaagc cttcggagac cctgtccctc      60
acctgcacta tctctggtgg ctccgtcagc agtggtgatt actactggag ctggatccgg     120
cagcccccag ggaagggact ggagtggatt gggaacatct attacagtgg gagcaccaac     180
tacaacccct ccctcaagag tcgagtcacc atatcggtag acacgtccaa gaaccagttc     240
tccctgaagc tgagctctgt gaccgctgcg gacacggccg tgtattactg tgcgagaggg     300
gggggtactg tggttcgggg aattatccat tactactact actacggtat ggacgtctgg     360
ggccaaggga ccacggtcac cgtctcctca                                     390
```

<210> SEQ ID NO 110
<211> LENGTH: 324
<212> TYPE: DNA
<213> ORGANISM: Homo sapiens

<400> SEQUENCE: 110

```
gaaattgtgt tgacgcagtc tccaggcacc ctgtctttgt ctccagggga aagagccacc      60
ctctcctgca gggccagtca gagtgttagc agcggacact tagcctggta ccagcagaaa     120
cctggccagg ctcccaggct cctcatctat ggtgcatcca gcagggccac tggcatccca     180
ggcaggttca gtggcagtgg gtctgggaca gacttcactc tcaccatcag cagactggag     240
cctgaagatt ttgcagtgta ttactgtcag cagtatggta gctcaccgta cacttttggc     300
caggggacca agctggagat caaa                                           324
```

<210> SEQ ID NO 111
<211> LENGTH: 324
<212> TYPE: DNA
<213> ORGANISM: Homo sapiens

<400> SEQUENCE: 111
gaaattgtgt tgacacagtc tccagccatc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctggagcct   240
gaagattttg cagtttatta ctgtcagcag cgtagcaact ggcctccact cactttcggc   300
ggagggacca aggtggagat caaa                                          324

<210> SEQ ID NO 112
<211> LENGTH: 324
<212> TYPE: DNA
<213> ORGANISM: Homo sapiens

<400> SEQUENCE: 112
gaaattgtgt tgacacagtc tccagccatc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctggagcct   240
gaagattttg cagtttatta ctgtcagcag cgtagcaact ggcctccact cactttcggc   300
ggagggacca aggtggagat caaa                                          324

<210> SEQ ID NO 113
<211> LENGTH: 321
<212> TYPE: DNA
<213> ORGANISM: Homo sapiens

<400> SEQUENCE: 113
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttgatagtt tccctcacac tttcggcgga   300
gggaccaagg tggagatcaa a                                             321

<210> SEQ ID NO 114
<211> LENGTH: 327
<212> TYPE: DNA
<213> ORGANISM: Homo sapiens

<400> SEQUENCE: 114
gaaattgtgt tgacgcagtc tccaggcacc ctgtctttgt ctccagggga aagagccacc    60
ctctcctgca gggccagtca gagtgttagc agcagctatt tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacctat attcactttc   300
ggccctggga ccaaagtgga tatcaaa                                       327

<210> SEQ ID NO 115
<211> LENGTH: 321
<212> TYPE: DNA
<213> ORGANISM: Homo sapiens

<400> SEQUENCE: 115

```
gaagttgtgt tgacgcagtc tccaggcacc ctgtctttgt ctccagggga aagagccacc      60
ctctcctgca gggccagtca gagtattagc agcggctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacccac tttcggcgga     300
gggaccaagg tggagatcaa a                                                321
```

<210> SEQ ID NO 116
<211> LENGTH: 324
<212> TYPE: DNA
<213> ORGANISM: Homo sapiens

<400> SEQUENCE: 116

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgta cacttttggc     300
caggggacca agctggagat caaa                                             324
```

<210> SEQ ID NO 117
<211> LENGTH: 321
<212> TYPE: DNA
<213> ORGANISM: Homo sapiens

<400> SEQUENCE: 117

```
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt accctcccac tttcggcgga     300
gggaccaagg tggagatcaa a                                                321
```

<210> SEQ ID NO 118
<211> LENGTH: 324
<212> TYPE: DNA
<213> ORGANISM: Homo sapiens

<400> SEQUENCE: 118

```
gaaattgtgt tgacacagtc tccagccacc ctgtctttgt ctccagggga aagagccacc      60
ctctcctgca gggccagtca gagtgttagc agctacgtag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg caatttatta ctgtcagcag cgtagcaact cgcctccgtg gacgttcggc     300
caagggacca aggtggaaat caaa                                             324
```

<210> SEQ ID NO 119
<211> LENGTH: 327
<212> TYPE: DNA
<213> ORGANISM: Homo sapiens

<400> SEQUENCE: 119

| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcacctcc attcactttc | 300 |
| ggccctggga ccaaagtgga tatcaaa | 327 |

<210> SEQ ID NO 120
<211> LENGTH: 654
<212> TYPE: DNA
<213> ORGANISM: Homo sapiens

<400> SEQUENCE: 120

| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcacctcc attcactttc | 300 |
| ggccctggga ccaaagtgga tatcaagaa attgtgttga cgcagtctcc aggcaccctg | 360 |
| tctttgtctc caggggaaag agccaccctc tcctgcaggg ccagtcagag tgttagcagc | 420 |
| agctacttag cctggtacca gcagaaacct ggccaggctc ccaggctcct catctatggt | 480 |
| gcatccagca gggccactgg catcccagac aggttcagtg gcagtgggtc tgggacagac | 540 |
| ttcactctca ccatcagcag actggagcct gaagattttg cagtgtatta ctgtcagcag | 600 |
| tatggtagct caccggagta cacttttggc caggggacca agctggagat caaa | 654 |

<210> SEQ ID NO 121
<211> LENGTH: 98
<212> TYPE: PRT
<213> ORGANISM: Homo sapiens

<400> SEQUENCE: 121

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Met Ser Lys Arg
                85                  90                  95

Ser Pro

<210> SEQ ID NO 122
<211> LENGTH: 368
<212> TYPE: PRT
<213> ORGANISM: Homo sapiens

<400> SEQUENCE: 122

Met Val Leu Glu Val Ser Asp His Gln Val Leu Asn Asp Ala Glu Val
1               5                   10                  15

Ala Ala Leu Leu Glu Asn Phe Ser Ser Tyr Asp Tyr Gly Glu Asn
            20                  25                  30

Glu Ser Asp Ser Cys Cys Thr Ser Pro Pro Cys Pro Gln Asp Phe Ser
        35                  40                  45

Leu Asn Phe Asp Arg Ala Phe Leu Pro Ala Leu Tyr Ser Leu Leu Phe
        50                  55                  60

Leu Leu Gly Leu Leu Gly Asn Gly Ala Val Ala Ala Val Leu Leu Ser
65                  70                  75                  80

Arg Arg Thr Ala Leu Ser Ser Thr Asp Thr Phe Leu Leu His Leu Ala
                85                  90                  95

Val Ala Asp Thr Leu Leu Val Leu Thr Leu Pro Leu Trp Ala Val Asp
                100                 105                 110

Ala Ala Val Gln Trp Val Phe Gly Ser Gly Leu Cys Lys Val Ala Gly
        115                 120                 125

Ala Leu Phe Asn Ile Asn Phe Tyr Ala Gly Ala Leu Leu Leu Ala Cys
        130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
        180                 185                 190

His His Asp Glu Arg Leu Asn Ala Thr His Cys Gln Tyr Asn Phe Pro
        195                 200                 205

Gln Val Gly Arg Thr Ala Leu Arg Val Leu Gln Leu Val Ala Gly Phe
        210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Val Ala Phe Ala Leu Cys Trp Thr Pro Tyr His
                260                 265                 270

Leu Val Val Leu Val Asp Ile Leu Met Asp Leu Gly Ala Leu Ala Arg
        275                 280                 285

Asn Cys Gly Arg Glu Ser Arg Val Asp Val Ala Lys Ser Val Thr Ser
        290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
        340                 345                 350

Arg Asp Ser Ser Trp Ser Glu Thr Ser Glu Ala Ser Tyr Ser Gly Leu
        355                 360                 365

<210> SEQ ID NO 123
<211> LENGTH: 98
<212> TYPE: PRT
<213> ORGANISM: Macaca mulatta

<400> SEQUENCE: 123

Met Asn Gln Thr Ala Ile Leu Ile Cys Cys Leu Val Phe Leu Thr Leu
1               5                   10                  15

```
Ser Gly Ile Gln Gly Ile Pro Leu Ser Arg Thr Val Arg Cys Thr Cys
            20                  25                  30

Ile Ser Ile Ser Asn Gln Pro Val Asn Pro Arg Ser Leu Glu Lys Leu
            35                  40                  45

Glu Ile Ile Pro Pro Ser Gln Phe Cys Pro His Val Glu Ile Ile Ala
        50                  55                  60

Thr Met Lys Lys Lys Gly Glu Lys Arg Cys Leu Asn Pro Glu Ser Lys
 65                  70                  75                  80

Ala Ile Lys Asn Leu Leu Lys Ala Val Ser Lys Glu Arg Ser Lys Arg
                85                  90                  95

Ser Pro

<210> SEQ ID NO 124
<211> LENGTH: 98
<212> TYPE: PRT
<213> ORGANISM: Mus musculus

<400> SEQUENCE: 124

Met Asn Pro Ser Ala Ala Val Ile Phe Cys Leu Ile Leu Leu Gly Leu
 1               5                  10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
            35                  40                  45

Glu Ile Ile Pro Ala Ser Leu Ser Cys Pro Arg Val Glu Ile Ile Ala
        50                  55                  60

Thr Met Lys Lys Asn Asp Glu Gln Arg Cys Leu Asn Pro Glu Ser Lys
 65                  70                  75                  80

Thr Ile Lys Asn Leu Met Lys Ala Phe Ser Gln Lys Arg Ser Lys Arg
                85                  90                  95

Ala Pro

<210> SEQ ID NO 125
<211> LENGTH: 125
<212> TYPE: PRT
<213> ORGANISM: Homo sapiens

<400> SEQUENCE: 125

Met Lys Lys Ser Gly Val Leu Phe Leu Leu Gly Ile Ile Leu Leu Val
 1               5                  10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
            35                  40                  45

Leu Lys Gln Phe Ala Pro Ser Pro Ser Cys Glu Lys Ile Glu Ile Ile
        50                  55                  60

Ala Thr Leu Lys Asn Gly Val Gln Thr Cys Leu Asn Pro Asp Ser Ala
 65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Val Leu Lys
            100                 105                 110

Val Arg Lys Ser Gln Arg Ser Arg Gln Lys Lys Thr Thr
            115                 120                 125

<210> SEQ ID NO 126
```

-continued

```
<211> LENGTH: 94
<212> TYPE: PRT
<213> ORGANISM: Homo sapiens

<400> SEQUENCE: 126

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90
```